(12) United States Patent
Silvestrini et al.

(10) Patent No.: US 9,585,789 B2
(45) Date of Patent: Mar. 7, 2017

(54) OCULAR IMPLANT WITH HYDROGEL EXPANSION CAPABILITIES

(75) Inventors: Tom Silvestrini, Alamo, CA (US); Eugene De Juan, Jr., San Francisco, CA (US); Dan Rosenman, San Francisco, CA (US)

(73) Assignee: Novartis AG, Basel (CH)

( * ) Notice: Subject to any disclaimer, the term of this patent is extended or adjusted under 35 U.S.C. 154(b) by 662 days.

(21) Appl. No.: 13/365,175

(22) Filed: Feb. 2, 2012

(65) Prior Publication Data

US 2012/0220917 A1 Aug. 30, 2012

Related U.S. Application Data

(63) Continuation of application No. 12/175,294, filed on Jul. 17, 2008, now Pat. No. 8,672,870.

(60) Provisional application No. 60/950,315, filed on Jul. 17, 2007.

(51) Int. Cl.
*A61F 9/007* (2006.01)

(52) U.S. Cl.
CPC .. *A61F 9/00781* (2013.01); *A61F 2210/0061* (2013.01); *A61F 2250/0087* (2013.01)

(58) Field of Classification Search
CPC .................................................. A61F 9/00781
USPC .................. 604/8, 9, 294; 606/4–6
See application file for complete search history.

(56) References Cited

U.S. PATENT DOCUMENTS

| 3,767,759 A | 10/1973 | Wichterle |
|---|---|---|
| 3,788,327 A | 1/1974 | Donowitz et al. |
| 3,915,172 A | 10/1975 | Wichterle et al. |
| 4,037,604 A | 7/1977 | Newkirk |
| 4,402,681 A | 9/1983 | Haas et al. |
| 4,457,757 A | 7/1984 | Molteno |
| 4,521,210 A | 6/1985 | Wong |
| 4,554,918 A | 11/1985 | White |
| 4,604,087 A | 8/1986 | Joseph |
| 4,634,418 A | 1/1987 | Binder |
| 4,722,724 A | 2/1988 | Schocket |
| 4,750,901 A | 6/1988 | Molteno |
| 4,782,819 A | 11/1988 | Adair |
| 4,787,885 A | 11/1988 | Binder |
| 4,826,478 A | 5/1989 | Schocket |

(Continued)

FOREIGN PATENT DOCUMENTS

| EP | 0228185 | 7/1987 |
|---|---|---|
| EP | 1173124 | 1/2002 |

(Continued)

OTHER PUBLICATIONS

Barsky et al. "Evaluation of absorbable gelatin film (Gelfilm) in cyclodialysis clefts" Arch. Ophth. 60(6): 1044-1052,1958.

(Continued)

*Primary Examiner* — Philip R Wiest
(74) *Attorney, Agent, or Firm* — Fred C. Hernandez; Mintz Levin Cohn Ferris Glovsky and Popeo, P.C.

(57) ABSTRACT

An ocular implant includes an elongate member having an internal lumen forming a flow pathway that provides a fluid pathway between the anterior chamber and the suprachoroidal space of the eye. The implant includes a hydrogel member attached to the elongate member, wherein the hydrogel member is adapted to expand upon implantation of the elongate member in the eye. An attachment attaches the hydrogel member to the elongate member.

11 Claims, 52 Drawing Sheets

(56) References Cited

U.S. PATENT DOCUMENTS

| | | |
|---|---|---|
| 4,846,172 A | 7/1989 | Berlin |
| 4,863,457 A | 9/1989 | Lee |
| 4,886,488 A | 12/1989 | White |
| 4,900,300 A | 2/1990 | Lee |
| 4,946,436 A | 8/1990 | Smith |
| 4,968,296 A | 11/1990 | Ritch et al. |
| 5,041,081 A | 8/1991 | Odrich |
| 5,071,408 A | 12/1991 | Ahmed |
| 5,073,163 A | 12/1991 | Lippman |
| 5,092,837 A | 3/1992 | Ritch et al. |
| 5,127,901 A | 7/1992 | Odrich |
| 5,171,213 A | 12/1992 | Price, Jr. |
| 5,178,604 A | 1/1993 | Baerveldt et al. |
| 5,180,362 A | 1/1993 | Worst |
| 5,300,020 A | 4/1994 | L'Esperance, Jr. |
| 5,338,291 A | 8/1994 | Speckman et al. |
| 5,342,370 A | 8/1994 | Simon et al. |
| 5,346,464 A | 9/1994 | Camras |
| 5,370,607 A | 12/1994 | Memmen |
| 5,372,577 A | 12/1994 | Ungerleider |
| 5,397,300 A | 3/1995 | Baerveldt et al. |
| 5,433,701 A | 7/1995 | Rubinstein |
| 5,443,505 A | 8/1995 | Wong et al. |
| 5,454,746 A | 10/1995 | Guegan et al. |
| 5,476,445 A | 12/1995 | Baerveldt et al. |
| 5,536,274 A | 7/1996 | Neuss |
| 5,556,427 A | 9/1996 | Durette |
| 5,558,629 A | 9/1996 | Baerveldt et al. |
| 5,558,630 A | 9/1996 | Fisher |
| 5,601,094 A | 2/1997 | Reiss |
| 5,626,558 A | 5/1997 | Suson |
| 5,626,559 A | 5/1997 | Solomon |
| 5,651,782 A | 7/1997 | Simon et al. |
| 5,676,944 A | 10/1997 | Alvarado et al. |
| 5,702,414 A | 12/1997 | Richter et al. |
| 5,704,907 A | 1/1998 | Nordquist et al. |
| 5,713,844 A | 2/1998 | Peyman |
| 5,741,292 A | 4/1998 | Mendius |
| 5,743,868 A | 4/1998 | Brown et al. |
| 5,752,928 A | 5/1998 | de Roulhac et al. |
| 5,807,302 A | 9/1998 | Wandel |
| 5,868,697 A | 2/1999 | Richter et al. |
| 5,882,327 A | 3/1999 | Jacob |
| 5,893,837 A | 4/1999 | Eagles et al. |
| 5,968,058 A | 10/1999 | Richter et al. |
| 6,007,510 A | 12/1999 | Nigam |
| 6,007,511 A | 12/1999 | Prywes |
| 6,019,786 A | 2/2000 | Thompson |
| 6,050,970 A | 4/2000 | Baerveldt |
| 6,077,299 A | 6/2000 | Adelberg et al. |
| 6,102,045 A | 8/2000 | Nordquist et al. |
| 6,142,969 A | 11/2000 | Nigam |
| 6,186,974 B1 | 2/2001 | Allan et al. |
| 6,203,513 B1 | 3/2001 | Yaron et al. |
| 6,221,078 B1 | 4/2001 | Bylsma |
| 6,251,090 B1 | 6/2001 | Avery et al. |
| 6,261,256 B1 | 7/2001 | Ahmed |
| 6,264,668 B1 | 7/2001 | Prywes |
| 6,331,313 B1 | 12/2001 | Wong et al. |
| 6,375,642 B1 | 4/2002 | Grieshaber et al. |
| 6,383,219 B1 | 5/2002 | Telandro et al. |
| 6,450,984 B1 | 9/2002 | Lynch et al. |
| 6,464,724 B1 | 10/2002 | Lynch et al. |
| 6,468,283 B1 | 10/2002 | Richter et al. |
| 6,471,666 B1 | 10/2002 | Odrich |
| 6,471,777 B1 | 10/2002 | Kobayashi et al. |
| 6,508,779 B1 | 1/2003 | Suson |
| 6,510,600 B2 | 1/2003 | Yaron et al. |
| 6,524,275 B1 | 2/2003 | Lynch et al. |
| 6,533,768 B1 | 3/2003 | Hill |
| 6,537,568 B2 | 3/2003 | Olejnik et al. |
| 6,544,208 B2 | 4/2003 | Ethier et al. |
| 6,544,249 B1 | 4/2003 | Yu et al. |
| 6,558,342 B1 | 5/2003 | Yaron et al. |
| 6,589,203 B1 | 7/2003 | Mitrev |
| 6,595,945 B2 | 7/2003 | Brown |
| 6,626,858 B2 | 9/2003 | Lynch et al. |
| 6,638,239 B1 | 10/2003 | Bergheim et al. |
| 6,648,283 B2 | 11/2003 | Chase et al. |
| 6,666,841 B2 | 12/2003 | Gharib et al. |
| 6,676,607 B2 | 1/2004 | De Juan, Jr. et al. |
| 6,699,210 B2 | 3/2004 | Williams et al. |
| 6,699,211 B2 | 3/2004 | Savage |
| 6,719,750 B2 | 4/2004 | Varner et al. |
| 6,726,664 B2 | 4/2004 | Yaron et al. |
| 6,730,056 B1 | 5/2004 | Ghaem et al. |
| 6,736,791 B1 | 5/2004 | Tu et al. |
| 6,741,666 B1 | 5/2004 | Henry et al. |
| 6,780,164 B2 | 8/2004 | Bergheim et al. |
| 6,783,544 B2 | 8/2004 | Lynch et al. |
| 6,827,699 B2 | 12/2004 | Lynch et al. |
| 6,827,700 B2 | 12/2004 | Lynch et al. |
| 6,881,197 B1 | 4/2005 | Nigam |
| 6,881,198 B2 | 4/2005 | Brown |
| 6,939,298 B2 | 9/2005 | Brown et al. |
| 6,955,656 B2 | 10/2005 | Bergheim et al. |
| 6,962,573 B1 | 11/2005 | Wilcox |
| 6,966,888 B2 | 11/2005 | Cullen et al. |
| 6,969,384 B2 | 11/2005 | De Juan, Jr. et al. |
| 6,981,958 B1 | 1/2006 | Gharib et al. |
| 6,989,007 B2 | 1/2006 | Shadduck |
| 7,041,077 B2 | 5/2006 | Shields |
| 7,090,681 B2 | 8/2006 | Weber et al. |
| 7,094,225 B2 | 8/2006 | Tu et al. |
| 7,135,009 B2 | 11/2006 | Tu et al. |
| 7,160,264 B2 | 1/2007 | Lisk, Jr. et al. |
| 7,163,543 B2 | 1/2007 | Smedley et al. |
| 7,186,232 B1 | 3/2007 | Smedley et al. |
| 7,192,412 B1 | 3/2007 | Zhou et al. |
| 7,195,774 B2 | 3/2007 | Carvalho et al. |
| 7,207,965 B2 | 4/2007 | Simon |
| 7,220,238 B2 | 5/2007 | Lynch et al. |
| 7,273,475 B2 | 9/2007 | Tu et al. |
| 7,291,125 B2 | 11/2007 | Coroneo |
| 7,297,130 B2 | 11/2007 | Bergheim et al. |
| 7,331,984 B2 | 2/2008 | Tu et al. |
| 7,431,709 B2 | 10/2008 | Pinchuk et al. |
| 7,431,710 B2 | 10/2008 | Tu et al. |
| 7,488,303 B1 | 2/2009 | Haffner et al. |
| 7,563,241 B2 | 7/2009 | Tu et al. |
| 7,857,782 B2 | 12/2010 | Tu et al. |
| 8,506,515 B2 * | 8/2013 | Burns ................. A61F 9/00781 604/8 |
| 2002/0013546 A1 | 1/2002 | Grieshaber et al. |
| 2002/0013572 A1 | 1/2002 | Berlin |
| 2002/0072673 A1 | 6/2002 | Yamamoto et al. |
| 2002/0111608 A1 | 8/2002 | Baerveldt et al. |
| 2002/0128613 A1 | 9/2002 | Nakayama |
| 2002/0133168 A1 | 9/2002 | Smedley et al. |
| 2002/0143284 A1 | 10/2002 | Tu et al. |
| 2002/0156413 A1 | 10/2002 | Williams et al. |
| 2002/0165478 A1 | 11/2002 | Gharib et al. |
| 2002/0177856 A1 | 11/2002 | Richter et al. |
| 2002/0193725 A1 | 12/2002 | Odrich |
| 2003/0055372 A1 | 3/2003 | Lynch et al. |
| 2003/0060752 A1 | 3/2003 | Bergheim et al. |
| 2003/0097151 A1 | 5/2003 | Smedley et al. |
| 2003/0097171 A1 | 5/2003 | Elliott |
| 2003/0135149 A1 | 7/2003 | Cullen et al. |
| 2003/0181848 A1 | 9/2003 | Bergheim et al. |
| 2003/0187384 A1 | 10/2003 | Bergheim et al. |
| 2003/0208163 A1 | 11/2003 | Yaron et al. |
| 2003/0229303 A1 * | 12/2003 | Haffner et al. ................. 604/8 |
| 2003/0236483 A1 | 12/2003 | Ren |
| 2003/0236484 A1 | 12/2003 | Lynch et al. |
| 2004/0015140 A1 | 1/2004 | Shields |
| 2004/0024345 A1 | 2/2004 | Gharib et al. |
| 2004/0088048 A1 | 5/2004 | Richter et al. |
| 2004/0092856 A1 | 5/2004 | Dahan |
| 2004/0102729 A1 | 5/2004 | Haffner et al. |
| 2004/0102829 A1 | 5/2004 | Bonner et al. |
| 2004/0111050 A1 | 6/2004 | Smedley et al. |
| 2004/0127843 A1 | 7/2004 | Tu et al. |
| 2004/0147870 A1 | 7/2004 | Burns et al. |

(56) References Cited

U.S. PATENT DOCUMENTS

| | | |
|---|---|---|
| 2004/0148022 A1 | 7/2004 | Eggleston |
| 2004/0193095 A1 | 9/2004 | Shadduck |
| 2004/0193262 A1 | 9/2004 | Shadduck |
| 2004/0210181 A1 | 10/2004 | Vass et al. |
| 2004/0210185 A1 | 10/2004 | Tu et al. |
| 2004/0216749 A1 | 11/2004 | Tu |
| 2004/0225250 A1 | 11/2004 | Yablonski |
| 2004/0236343 A1 | 11/2004 | Taylor et al. |
| 2004/0249333 A1 | 12/2004 | Bergheim et al. |
| 2004/0254517 A1 | 12/2004 | Quiroz-Mercado et al. |
| 2004/0254519 A1 | 12/2004 | Tu et al. |
| 2004/0254520 A1 | 12/2004 | Porteous et al. |
| 2004/0254521 A1 | 12/2004 | Simon |
| 2004/0260228 A1 | 12/2004 | Lynch et al. |
| 2005/0008673 A1 | 1/2005 | Snyder et al. |
| 2005/0049578 A1 | 3/2005 | Tu et al. |
| 2005/0090806 A1 | 4/2005 | Lynch et al. |
| 2005/0090807 A1 | 4/2005 | Lynch et al. |
| 2005/0107734 A1 | 5/2005 | Coroneo |
| 2005/0119601 A9 | 6/2005 | Lynch et al. |
| 2005/0119636 A1 | 6/2005 | Haffner et al. |
| 2005/0119737 A1 | 6/2005 | Bene et al. |
| 2005/0125003 A1 | 6/2005 | Pinchuk et al. |
| 2005/0143817 A1 | 6/2005 | Hunter et al. |
| 2005/0149080 A1 | 7/2005 | Hunter et al. |
| 2005/0171507 A1 | 8/2005 | Christian et al. |
| 2005/0175663 A1 | 8/2005 | Hunter et al. |
| 2005/0181011 A1 | 8/2005 | Hunter et al. |
| 2005/0181977 A1 | 8/2005 | Hunter et al. |
| 2005/0182350 A1 | 8/2005 | Nigam |
| 2005/0191331 A1 | 9/2005 | Hunter et al. |
| 2005/0192527 A1 | 9/2005 | Gharib et al. |
| 2005/0197613 A1 | 9/2005 | Sniegowski et al. |
| 2005/0209549 A1 | 9/2005 | Bergheim et al. |
| 2005/0209550 A1 | 9/2005 | Bergheim et al. |
| 2005/0232972 A1 | 10/2005 | Odrich |
| 2005/0244462 A1 | 11/2005 | Farooq |
| 2005/0250788 A1 | 11/2005 | Tu et al. |
| 2005/0266047 A1 | 12/2005 | Tu et al. |
| 2005/0267397 A1 | 12/2005 | Bhalla |
| 2005/0267398 A1 | 12/2005 | Protopsaltis et al. |
| 2005/0271704 A1 | 12/2005 | Tu et al. |
| 2005/0273033 A1 | 12/2005 | Grahn et al. |
| 2005/0277864 A1 | 12/2005 | Haffner et al. |
| 2005/0283108 A1 | 12/2005 | Savage |
| 2005/0287188 A1 | 12/2005 | Anderson et al. |
| 2005/0288617 A1 | 12/2005 | Yaron et al. |
| 2005/0288619 A1 | 12/2005 | Gharib et al. |
| 2006/0020248 A1 | 1/2006 | Prescott |
| 2006/0032507 A1 | 2/2006 | Tu |
| 2006/0036207 A1 | 2/2006 | Koonmen et al. |
| 2006/0069340 A1 | 3/2006 | Simon |
| 2006/0074375 A1 | 4/2006 | Bergheim et al. |
| 2006/0084907 A1 | 4/2006 | Bergheim et al. |
| 2006/0116626 A1 | 6/2006 | Smedley et al. |
| 2006/0155238 A1 | 7/2006 | Shields |
| 2006/0155300 A1 | 7/2006 | Stamper et al. |
| 2006/0173397 A1 | 8/2006 | Tu et al. |
| 2006/0195055 A1 | 8/2006 | Bergheim et al. |
| 2006/0195056 A1 | 8/2006 | Bergheim et al. |
| 2006/0200113 A1 | 9/2006 | Haffner et al. |
| 2006/0235367 A1 | 10/2006 | Takashima et al. |
| 2006/0241580 A1 | 10/2006 | Mittelstein et al. |
| 2006/0241749 A1 | 10/2006 | Tu et al. |
| 2007/0010827 A1 | 1/2007 | Tu et al. |
| 2007/0088242 A1 | 4/2007 | Coroneo |
| 2007/0088424 A1 | 4/2007 | Greenberg et al. |
| 2007/0088432 A1 | 4/2007 | Solovay et al. |
| 2007/0106235 A1 | 5/2007 | Coroneo |
| 2007/0106236 A1 | 5/2007 | Coroneo |
| 2007/0112292 A1 | 5/2007 | Tu et al. |
| 2007/0118147 A1 | 5/2007 | Smedley et al. |
| 2007/0149915 A1 | 6/2007 | Yablonski |
| 2007/0191863 A1 | 8/2007 | De Juan et al. |
| 2007/0233037 A1 | 10/2007 | Gifford, et al. |
| 2007/0276315 A1 | 11/2007 | Haffner et al. |
| 2007/0276316 A1 | 11/2007 | Haffner et al. |
| 2007/0282244 A1 | 12/2007 | Tu et al. |
| 2007/0282245 A1 | 12/2007 | Tu et al. |
| 2007/0293807 A1 | 12/2007 | Lynch et al. |
| 2008/0015488 A1 | 1/2008 | Tu et al. |
| 2008/0045878 A1 | 2/2008 | Bergheim et al. |
| 2008/0058704 A1 | 3/2008 | Hee et al. |
| 2008/0147021 A1 | 6/2008 | Jani |
| 2008/0195027 A1 | 8/2008 | Coroneo |
| 2008/0200860 A1 | 8/2008 | Tu et al. |
| 2008/0228127 A1 | 9/2008 | Burns et al. |
| 2008/0234624 A2 | 9/2008 | Bergheim et al. |
| 2009/0036819 A1 | 2/2009 | Tu et al. |
| 2009/0118702 A1* | 5/2009 | Lazar .......................... 604/521 |
| 2010/0010416 A1 | 1/2010 | Juan, Jr. et al. |
| 2010/0137981 A1 | 6/2010 | Silvestrini et al. |
| 2010/0152641 A1 | 6/2010 | Yablonski |
| 2010/0274259 A1 | 10/2010 | Yaron et al. |
| 2011/0028883 A1 | 2/2011 | Juan, Jr. et al. |
| 2011/0098629 A1 | 4/2011 | Juan, Jr. et al. |
| 2011/0105990 A1 | 5/2011 | Silvestrini |
| 2011/0112546 A1 | 5/2011 | Juan, Jr. et al. |

FOREIGN PATENT DOCUMENTS

| | | |
|---|---|---|
| EP | 1173125 | 1/2002 |
| EP | 1173126 | 1/2002 |
| EP | 1184010 | 3/2002 |
| EP | 1278492 | 1/2003 |
| EP | 1292256 | 3/2003 |
| EP | 1310222 | 5/2003 |
| EP | 1418868 | 5/2004 |
| EP | 1473004 | 11/2004 |
| EP | 1477146 | 11/2004 |
| EP | 1545655 | 6/2005 |
| EP | 1977724 | 10/2008 |
| EP | 2027837 | 2/2009 |
| GB | 2101891 | 1/1983 |
| JP | 62-044250 A | 2/1987 |
| JP | 2003-520077 A | 7/2003 |
| JP | 2005-512607 A | 5/2005 |
| JP | 2007-501066 A | 1/2007 |
| JP | 2009-532132 A | 9/2009 |
| RU | 2018289 C1 | 8/1994 |
| RU | 2056818 C1 | 3/1996 |
| RU | 2074686 C1 | 3/1997 |
| RU | 2074687 C1 | 3/1997 |
| RU | 2157678 C1 | 10/2000 |
| WO | WO 89/00869 | 2/1989 |
| WO | WO 91/12046 | 8/1991 |
| WO | WO 92/19294 | 11/1992 |
| WO | WO 94/09721 | 5/1994 |
| WO | WO 94/09837 | 5/1994 |
| WO | WO 94/13234 | 6/1994 |
| WO | WO 95/08310 | 3/1995 |
| WO | WO 96/20742 | 7/1996 |
| WO | WO 96/36377 | 11/1996 |
| WO | WO 98/23237 | 6/1998 |
| WO | WO 98/30181 | 7/1998 |
| WO | WO 99/26567 | 6/1999 |
| WO | WO 00/06223 | 2/2000 |
| WO | WO 00/64389 | 11/2000 |
| WO | WO 00/64511 | 11/2000 |
| WO | WO 01/78656 | 10/2001 |
| WO | WO 02/36052 | 5/2002 |
| WO | WO 02/070045 | 9/2002 |
| WO | WO 02/074052 | 9/2002 |
| WO | WO 02/080811 | 10/2002 |
| WO | WO 02/080829 | 10/2002 |
| WO | WO 02/087418 | 11/2002 |
| WO | WO 02/087479 | 11/2002 |
| WO | WO 02/089699 | 11/2002 |
| WO | WO 02/102274 | 12/2002 |
| WO | WO 03/015659 | 2/2003 |
| WO | WO 03/015667 | 2/2003 |
| WO | WO 03/041622 | 5/2003 |
| WO | WO 03/073968 | 9/2003 |
| WO | WO 03/099175 | 12/2003 |

(56) References Cited

FOREIGN PATENT DOCUMENTS

| | | |
|---|---|---|
| WO | WO 2004/026347 | 4/2004 |
| WO | WO 2004/043231 | 5/2004 |
| WO | WO 2004/056294 | 7/2004 |
| WO | WO 2004/060219 | 7/2004 |
| WO | WO 2004/062469 | 7/2004 |
| WO | WO 2004/066871 | 8/2004 |
| WO | WO 2004/110391 | 12/2004 |
| WO | WO 2005/016418 | 2/2005 |
| WO | WO 2005/046782 | 5/2005 |
| WO | WO 2005/055873 | 6/2005 |
| WO | WO 2005/105197 | 11/2005 |
| WO | WO 2005/107664 | 11/2005 |
| WO | WO 2005/107845 | 11/2005 |
| WO | WO-2005/117780 A2 | 12/2005 |
| WO | WO 2006/012421 | 2/2006 |
| WO | WO-2006/014434 A2 | 2/2006 |
| WO | WO 2006/036715 | 4/2006 |
| WO | WO 2006/099738 | 9/2006 |
| WO | WO 2007/087061 | 8/2007 |
| WO | WO 2007/115259 | 10/2007 |
| WO | WO 2007/130393 | 11/2007 |
| WO | WO 2008/061043 | 5/2008 |
| WO | WO 2009/012406 | 1/2009 |
| WO | WO 2009/158524 | 12/2009 |
| WO | WO 2013/059678 | 10/2012 |

OTHER PUBLICATIONS

Bick, M. "Use of Tantalum for Ocular Drainage," Arch Ophthal. Oct. 1949; 42(4): 373-88.
Bietti, G., "The present state of the use of plastics in eye surgery" Acta Ophthalmol (Copenh) 1955; 33(4):337-70.
Brown et al., "Internal Sclerectomy for Glaucoma Filtering Surgery with an Automated Trephine," Archives of Ophthalmology, Jan. 1987, vol. 105: 133-136.
Burchfield JC, Kass MA, Wax MB. Primary valve malfunction of the Krupin eye valve with disk. J Glaucoma. Jun. 1997;6(3):152-6.
Chiou et al. "Ultrasound biomicroscopy of eyes undergoing deep sclerectomy with collagen implant" Br J Ophthalmol 80 (1996), pp. 541-544.
Chylack LT, Bellows AR. Molecular sieving in suprachoroidal fluid formation in man. Invest Ophthalmol Vis Sci 17: 420, 1978.
Classen et al. "A histopathologic and immunohistorchemical analysis of the filtration bleb after unsuccessful glaucoma seton implantation" Am. J. Ophthalmol. 122:205-12 (1996).
Cohen et al. "First day post-operative review following uncomplicated phacoemulsification" Eye 12(4):634-6 (1998).
Collaborative Normal-Tension Study Group. Comparison of glaucomatous progression between untreated patients with normal-tension glaucoma and patients with therapeutically reduced intraocular pressures. Am J Ophthalmol 1998;126:487-497.
Congdon N, O'Colmain B, Klaver CC, et al. Causes and prevalence of visual impairment among adults in the United States. Arch Ophthalmol 2004;122:477-85.
Demailly et al. "Non-penetrating deep sclerectomy (NPDS) with or without collagen device (CD) in primary open-angle glaucoma: middle-term retrospective study" International Ophthalmology 20: 131-140, 1997.
Derwent English abstract for EP 1184010, published Mar. 6, 2002 entitled: "Drainage unit for an eye, consists of a hollow line, a distribution member, and a pressure relief valve which only allows water to leave the eye chamber above a certain pressure," Accession Nbr. 12409716 [351].
Dinakaran et al., "Is the first post-operative day review necessary following uncomplicated phacoemulsification surgery?" Eye, 14(3A):364-6 (2000).
Draeger "Chirurgische Mal nahmen bei kongenitalem Glaukom" (Surgical Interventions in Congenital Glaucoma) Klin Monatsbl Augenheilkd 1993; 202(5): 425-427 [Article in German with English summary included].

Einmahl et al. "Evaluation of a novel biomaterial in the suprachoroidal space of the rabbit eye" Invest Ophthalmol Vis Sci. 43:1533-1539 (2002).
Ellis, RA "A Reduction of Intraocular Pressure Using Plastics in Surgery" Am J Ophth. 50; 1960, 733-742.
Emi et al. "Hydrostatic pressure of the suprachoroidal space" Invest. Ophthal. Visual Sci. 30(2):233-238 (1989).
Fanous MM, Cohn RA. Propionibacterium endophthalmitis following Molteno tube repositioning. J Glaucoma. Aug. 1997;6(4):201-2.
Friedman DS, Wolfs RC, O'Colmain BJ, et al. Prevalence of open-angle glaucoma among adults in the United States. Arch Ophthalmol 2004;122:532-8.
Fuchs, E., "Detachment of the choroid inadvertently during cataract surgery" von Graefes Arch Ophthalmol, 51:199-224 (1900) [Article in German with English summary].
Gills, "Cyclodialysis Implants in Human Eyes" Am J Ophth 61:1966,841-846.
Gills, J., "Cyclodialysis implants" South Med J. 1967 60(7):692-5.
Gills, J., et al., "Action of cyclodialysis utilizing an implant studied by manometry in a human eye" Exptl Eye Res 1967; 6:75-78.
Goldberg "Management of Uncontrolled Glaucoma With the Molteno System" Australian and New Zealand Journal of Ophthalmology 1987; 15: 97-107.
Gordon MO, Kass. MA, for the Ocular Hypertension Treatment Study Group. The Ocular Hypertension Treatment Study. Design and baseline description of the participants. Arch Ophthalmol 1999:573-83.
Grant, W.M., MD, Further Studies on Facility of Flow Through the Trabecular Meshwork, A.M.A. Archives of Ophthalmololgy, Oct. 1958, vol. 60, pp. 523-533.
Gross et al., "Surgical therapy of chronic glaucoma in aphakia and pseudophakia" Ophthalmology, 95:1195-201 (1988).
Harper SL, Foster CS. Intraocular lens explantation in uveitis. Int Ophthalmol Clin. 2000 Winter; 40(1):107-16.
Harrington "Cataract and glaucoma. Management of the coexistent conditions and a description of a new operation combining lens extraction with reverse cyclodialysis." Am J Ophthalmol. May 1966;61(5 Pt 2):1134-40.
Heijl A, Leske MC, Bengtsson B, et al for the Early Manifest Glaucoma Trial Group. Reduction of intraocular pressure and glaucoma progression. Results from the Early Manifest Glaucoma Trial. Arch Ophthalmol 2002;120:1268-79.
Heine, I., "Cyclodialysis, a new glaucoma operation" Dtsch Med Wochenschr, 31:824-826 (1905) [Article in German with English summary included].
Hildebrand et al. "Efficacy of anterior chamber decompression in controlling early intraocular pressure spikes after uneventful phacoemulsification" J. Catact Refract Surg., 29:1087-92 (2003).
Hoskins, et al., "Aqueous Humor Outflow", Becker-Shaffer's Diagnosis and Therapy of the Glaucomas, 6th Edition, Chapter 4, pp. 41-66, 1989.
Howorth, DJ, "Feasibility study for a micromachined glaucoma drainage device" Cranfield University School of industrial and manufacturing science MSc Thesis Academic Year 2001-2002 Sep. 13, 2002.
Hylton, C. et al., "Update on prostaglandin analogs", Curr Opin Ophthalmol, 14:65-9 (2003).
Javitt JC, Chiang YP. Preparing for managed competition. Utilization of ambulatory eye care visits to ophthalmologists. Arch Ophthalmol 1993;111:1034-5.
Jay JL, Allan D. The benefit of early trabeculectomy versus conventional management in primary open-angle glaucoma relative to severity of disease. Eye 1989; 3:528-35.
Jordan JF, Dietlein TS, Dinslage S, Luke C, Konen W, Krieglstein GK. Cyclodialysis ab interno as a surgical approach to intractable glaucoma. Graefes Arch Clin Exp Ophthalmol. Aug. 2007;245(8):1071-6.
Jordan, J. et al., "A Novel Approach to Suprachoroidal Drainage for the Surgical Treatment of Intractable Glaucoma," J. Glaucoma 2006; 15:200-205.
Karlen, M. et al., "Deep sclerectomy with collagen implant: medium term results," Br. J. Ophthalmol, Jan. 1999, 83(1):6-11.

(56) References Cited

OTHER PUBLICATIONS

Kass MA, Heuer DK, Higginbotham EJ, et al for the Ocular Hypertension Treatment Study Group. The Ocular HypertensionTreatment Study. A randomized trial determines that topical ocular hypotensive medication delays or prevents the onset of primary open-angle glaucoma. Arch Ophthalmol 2002;120:701-13.
Klemm et al. "Die Ultraschallbiomikroskopie als Kriterium der FunktionsprUfung des suprachorioidalen Spaltes nach kammerwinkelchirurgischen Eingriffen (Ultrasound Biomicroscopic Imaging for Assessment of the Suprachoroidal Cleft after Angle Surgery)" Klinische Monatsblatter fur Augenheilkunde 1997; 210: 74-77.
Klemm et al., "Experimental use of space-retaining substances with extended duration: functional and morphological results," Graefes Arch Clin Exp Ophthalmol Sep. 1995; 233(9):592-7.
Kozlov, et al., "Nonpenetrating deep sclerectomy with collagen," Ophthalmosurgery 3:44-46 (1990) [Article in Russian with English translation included].
Krejci L. "Microdrainage of anterior chamber of eye glaucoma operation using hydron capillary drain. " Acta Univ Carol Med Monogr. 1974;(61):1-90.
Krejci, L., "Cyclodialysis with hydroxymethyl methacrylate capillary strip (HCS). Animal experiments with a new approach in glaucoma drainage surgery," Ophthalmologica 1972; 164(2):113-21.
Kupfer"Studies on intraocular pressure. I. A technique for polyethylene tube implantation into the anterior chamber of the rabbit." Arch Ophthalmol. Apr. 1961;65:565-70.
La Rocca "Gonioplasty in GlaucomaA Preliminary Report" Br J Ophth 46:1962, 404-415.
Law et al., "Retinal Complications After Aqueous Shunt Surgical Procedures for Glaucoma" Arch Ophthal.; Dec. 1996; vol. 114:1473-1480.
Lee et al., "Magnetic resonance imaging of the aqueous flow in eyes implanted with thetrabeculo-suprachoroidal glaucoma seton," Invest. Ophthalmol. Vis. Sci. 33:948 (1992).
Lee KY. Trabeculo-suprachoroidal shunt for treating recalcitrant and secondary glaucoma. Presented at the American Academy of Ophthalmology Annual Meeting, Anaheim, CA, 1991.
Leske MC, Heijl A, Hussein M, et al for the Early Manifest Glaucoma Trial Group. Factors for glaucoma progression and the effect of treatment. The Early Manifest Glaucoma Trial. Arch Ophthalmol Jan. 2003;121:48-56.
Lichter PR, Musch DC, Gillespie BW, et al and the CIGTS Study Group. Interim clinical outcomes in the Collaborative Initial Glaucoma Treatment Study comparing initial treatment randomized to medications or surgery. Ophthalmology 2001;108:1943-53.
Losche, W., "Proposals for improvement of cyclodialysis," Klin Monatsblatter Augenheilkd Augenarztl Fortbild 1952, 121(6):715-6 [Article in German with English translation included].
Marx et al., "Use of the Ganciclovir Implant in the Treatment of Recurrent Cytomegalovirus Retinitis" Arch Ophthal.; Jul. 1996; vol. 114:815-820.
McPherson "Combined Trabeculotomy and Cataract Extraction as a Single Operation" Tr. Am. Ophth. Soc., vol. LXXIV, 1976; 251-260.
Migdal C, Gregory W, Hitchings R. Long term functional outcome after early surgery compared with laser and medicine in open-angle glaucoma. Ophthalmology 1994;101:1651-7.
Miglior S, Pfeiffer N, Zeyen T et al for the European Glaucoma Prevention Study Group. Results of the European Glaucoma Prevention Study. Ophthalmology 2005;112:366-75.
Miglior S, Zeyen T, Pfeiffer N, et al for the European Glaucoma Prevention Study Group. The European Glaucoma Prevention Study design and baseline description of the participants. Ophthalmology 2002;109:1612-21.
Miki, MD et al., "Intraocular Cannula for Continuous, Chronic Drug DeliveryHistopathic Observations and Function" Arch Ophthal.; May 1985; vol. 103:712-717.

Molteno et al. "Long tube implants in the management of glaucoma" South African Medical Journal, Jun. 26, 1976;50(27):1062-6.
Molteno et al. "The Vicryl tie technique for inserting a draining implant in the treatment of secondary glaucoma." Australian and New Zealand Journal of Ophthalmology 1986; 14: 343-354.
Moses RA "Detachment of ciliary body-anatomical and physical considerations" Investigative Ophthalmology & Visual Science, Assoc. For Research in Vision and Ophthalmology, US, vol. 4, No. 5, Oct. 1, 1965.
Nesterov, AP, et al., "Surgical stimulation of the uveoscleral outflow: Experimental studies on enucleated human eyes," Acta Opthalmol (Copenh) Jun.; 57(3):409-17 (1979).
Nguyen et al., "Complications of Baerveldt Glaucoma Drainage Implants" Arch Ophthal.; May 1998; vol. 116:571-575.
Noecker RJ. Clinical Evaluation of a Novel Gold Micro-Shunt for Reduction of 10 P in Refractory Glaucomas. American Glaucoma Society Annual Meeting, San Francisco, CA,2007.http://vvww.glaucomaweb.org/associations/5224/files/AGS%20AM07% 20Prgrm%20FIN AL.pdf. Accessed Nov. 1, 2008).
O'Brien et al. "Cyclodialysis" Arch Ophthal. 1949;42(5):606-619.
Olsen, Timothy W., et al., Cannulation of the Suprachoroidal Space: A Novel Drug Delivery Methodology to the Posterior Segment, American Journal of Ophthalmology, vol. 142, No. 5, Nov. 2006, pp. 777-787.e2.
Ozdamar, A, et al., "Suprachoroidal seton implantation in refractory glaucoma: a novel surgical technique," J. Glaucoma Aug. 2003; 12(4):354-9.
Pinnas, G., et al., "Cyclodialysis with teflon tube implants" Am J. Ophthalmol Nov. 1969; 68(5):879-883.
Portney GL, "Silicone elastomer implantation cyclodialysis." Arch Ophthalmol 1973; 89: 10-12.
Pruett et al., "The Fishmouth Phenomenon—II. Wedge Scleral Buckling" Arch Ophthal.; Oct. 1977; vol. 95:1782-1787.
Qadeer "Acrylic Gonio-Subconjunctival Plates in Glaucoma Surgery" Br J Ophthalmol. Jun. 1954; 38(6): 353-356.
Quigley HA, Vitale S. Models of open-angle glaucoma prevalence and incidence in the United States. Invest Ophthalmol Vis Sci 1997; 38:83-91.
Richards et al. "Artificial Drainage Tubes for Glaucoma" Am J Ophth 60:1965,405-408.
Ritch, et al., "Uveoscleral Outflow", The Glaucomas. St. Louis: Mosby, 1996; pp. 337-343.
Rohen, Johannes W., Anatomy of the Aqueous Outflow Channels, Glaucoma, vol. 1, Chapter 14, pp. 277-296, Edited by J.E. Cairns, Grune & Stratton, Harcourt Brace Jovanovich Publishers, 1986.
Rosenberg, L. et al. "Implants in glaucoma surgery," Chapter 88, the Glaucomas, Ritch et al. Eds. 2nd Ed. Mosby St. Louis 1986; p. 1783-1807.
Row, H., "Operation to Control Glaucoma," (1934) Arch. Ophthal 12, 325.
Rowan, Patrick J., MD, Combined Cyclodialysis and Cataract Surgery, Ophthalmic Surgery and Lasers, Dec. 1998, vol. 29, No. 12, pp. 962-968 (9 pages).
Sampimon "A New Approach to Filtering Glaucoma Surgery" Ophthalmologica (Basel) 151: 1966, 637-644.
Schappert S. Office visits for glaucoma: United States, 1991-92. Advance data from vital and health statistics. vol. 262. Hyattsville, MD: National Center for Health Statistics, 1995.
Shaffer RN, Weiss DI. Concerning cyclodialysis and hypotony. Arch Ophthalmol 68: 25, 1962.
SOLX Clinical Literature Handout; Industry Show Feb. 2006; "The SOLX Gold Micro-shunt (GMS) treatment".
Sommer A, Tielsch JM, Katz J, et al. Racial differences in the cause-specific prevalence of blindness in east Baltimore. N Engl J Med 1991;325:1412-7.
Sourdille et al. "Reticulated hyaluronic acid implant in non-perforating trabecular surgery." J Cataract Refract Surg 25: 332-339. (1999).
Srinivasan, R. et al., "Microbial contamination of the anterior chamber during phacoemulsification," J. Cataract Refract Surg. 28:2173-6 (2002).

(56) References Cited

OTHER PUBLICATIONS

Suguro K, Toris CB, Pederson JE. Uveoscleral outflow following cyclodialysis in the monkey eye using a fluorescent tracer. Invest Ophthalmol Vis Sci 1985: 26, 810.

The Advanced Glaucoma Intervention Study (AGIS): 7. The relationship between control of intraocular pressure and visual field deterioration. The AGIS Investigators. Am J Ophthalmol 2000;130:429-40.

The Advanced Glaucoma Intervention Study (AGIS); 13. Comparison of treatment outcomes within race: 10-year results. Ophthalmology 2004;111:651-64.

The Glaucoma Laser Trial (GLT) and Glaucoma Laser Trial Follow-up Study: 7. Results. Am J Ophthahnol 1995;120:718-31.

The Glaucoma Laser Trial (GLT). 2. Results of argon laser trabeculoplasty versus topical medicines. The Glaucoma Laser Trial Research Group. Ophthalmology 1990;97:1403-13.

Thiagalingam S, Tarongoy P, Hamrah P, Lobo AM, Nagao K, Barsam C, Bellows R, Pineda R. Complications of cosmetic iris implants. J Cataract Refract Surg. Jul. 2008;34(7):1222-4.

Tielsch JM, Sommer A, Katz J, et al. Racial variations in the prevalence of primary open-angle glaucoma. The Baltimore Eye Survey. JAMA 1991;266:369-74.

Toris, et al., "Aqueous humor dynamics in the aging human eye" Am J. Ophthalmol., 127:407-12 (1999).

Toris CB. Extravascular albumin concentration of the uvea. Invest Ophthalmol Vis Sci 1990; 31:43.

Toris et al. "Effect of intraocular pressure on uveoscleral outflow following cyclodialysis in the monkey eye." Investigative Ophthalmology & Visual Science. 26 (1985) 1745-1749.

Trigler L, Proia AD, Freedman SF. Fibrovascular ingrowth as a cause of Ahmed glaucoma valve failure in children. Am J Ophthalmol. Feb. 2006;141(2):388-9.

Troncosco, Manuel U., "Cyclodialysis with insertion of metal implant in treatment of glaucoma, Preliminary Report," Arch. Ophth. 23:270, 1940.

Troncoso, Manuel U., Tantalum implants for inducing hypotony, Am Journal of Ophthalmology, vol. 32(4):499-508 (1949).

Veen et al. "The gonioseton, a surgical treatment for chronic glaucoma" Documenta Ophthalmologica vol. 75, Nos. 3-4, 365-375. (1990).

Vossmerbaeumer U, Ditzen K, Jonas JB. Removal of an intracorneal hydrogel implant for hyperopia after LASIK. J Refract Surg. Jan. 2007;23(1):102-4.

Wagner, Justin A., et al., Characterization of Uveoscleral Outflow in Enucleated Porcine Eyes Perfused under Constant Pressure, Invest Ophthalmol Vis Sci., Published in edited form in Sep. 2004, vol. 45, Issue 9, pp. 3203-3206.

Wamsley S, Moster MR, Rai S, Alvim HS, Fontanarosa J. Results of the use of the Ex-PRESS miniature glaucoma implant in technically challenging, advanced glaucoma cases: a clinical pilot study. Am J Ophthalmol. Dec. 2004; 138(6): 1049-51.

Yablonski, M., "Some thoughts on the pressure dependence of uveoscleral flow," Journal of Glaucoma, 12(1):90-92 (2003).

Yablonski, M., "Trabeculectomy with Internal Tube Shunt: a novel glaucoma surgery," J. Glaucoma 14:91-97 (2005).

Zhou, J. et al., "A trabecular bypass flow hypothesis," J Glaucoma. 14(1):74-83 (2005).

U.S. Appl. No. 10/579,330, filed Aug. 8, 2006, Publ. No. 2007-0088242.
U.S. Appl. No. 11/615,810, filed Dec. 22, 2006, Publ. No. 2007-0191863.
U.S. Appl. No. 11/624,168, filed Jan. 17, 2007, Publ. No. 2007-0233037.
U.S. Appl. No. 12/175,294, filed Jul. 17, 2008, Publ. No. 2009-0182421.
U.S. Appl. No. 12/492,051, filed Jun. 25, 2009, Publ. No. 2010-0137981.
U.S. Appl. No. 12/561,680, filed Sep. 17, 2009, Publ. No. 2010-0010416.
U.S. Appl. No. 12/694,691, filed Jan. 27, 2010, Publ. No. 2010-0274258.
U.S. Appl. No. 12/711,201, filed Feb. 23, 2010, Publ. No. 2010-0152641.
U.S. Appl. No. 12/753,494, filed Apr. 2, 2010, Publ. No. 2010-0280317.
U.S. Appl. No. 12/846,201, filed Jul. 29, 2010, Publ. No. 2011-0112546.
U.S. Appl. No. 12/852,407, filed Aug. 6, 2010, Publ. No. 2011-0118835.
U.S. Appl. No. 12/898,593, filed Oct. 5, 2010, Publ. No. 2011-0028883.
U.S. Appl. No. 12/898,630, filed Oct. 5, 2010, Publ. No. 2011-0028983.
U.S. Appl. No. 12/905,003, filed Oct. 14, 2010, Publ. No. 2011-0028884.
U.S. Appl. No. 12/939,033, filed Nov. 3, 2010, Publ. No. 2011-0105990.
U.S. Appl. No. 12/970,482, filed Dec. 16, 2010, Publ. No. 2011-0098629.
U.S. Appl. No. 12/970,567, filed Dec. 16, 2010, Publ. No. 2011-0087148.
U.S. Appl. No. 12/972,176, filed Dec. 17, 2010, Publ. No. 2011-0087149.
U.S. Appl. No. 12/972,261, filed Dec. 17, 2010, Publ. No. 2011-0087150.
U.S. Appl. No. 12/972,325, filed Dec. 17, 2010, Publ. No. 2011-0087151.
U.S. Appl. No. 12/973,853, filed Dec. 20, 2010, Publ. No. 2011-0238075.
U.S. Appl. No. 13/157,221, filed Jun. 9, 2011, Publ. No. 2012-0035524.
U.S. Appl. No. 13/216,086, filed Jun. 9, 2011, Publ. No. 2012-0035525.
U.S. Appl. No. 13/216,086, filed Aug. 23, 2011, Publ. No. 2011-0306915.
U.S. Appl. No. 61/550,337, filed Oct. 21, 2011.
U.S. Appl. No. 61/635,471, filed Apr. 19, 2012.
U.S. Appl. No. 61/635,686, filed Apr. 19, 2012.
U.S. Appl. No. 61/637,122, filed Apr. 23, 2012.
U.S. Appl. No. 61/637,789, filed Apr. 24, 2012.
U.S. Appl. No. 13/157,180, filed Jun. 9, 2011, Publ. No. 2012-0035524.
U.S. Appl. No. 13/656,326, filed Oct. 19, 2012, Publ. No. 2013-0103145.
U.S. Appl. No. 13/721,941, filed Dec. 20, 2012, Publ. No. 2013-0110125.

\* cited by examiner

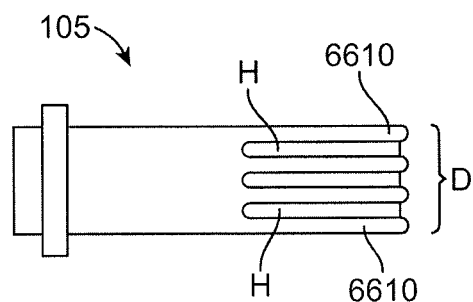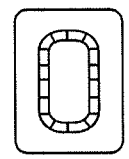
FIG. 66A   FIG. 66B
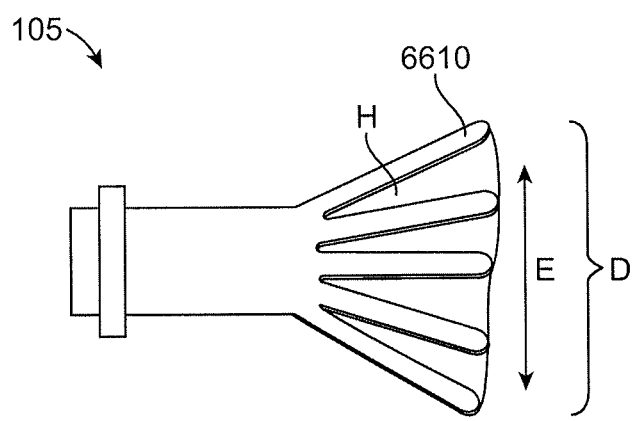
FIG. 67

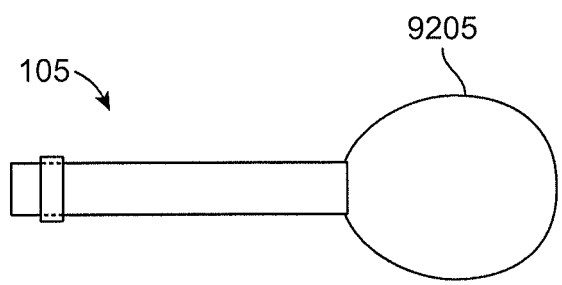 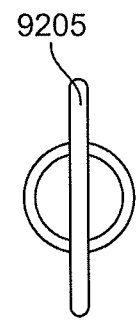
FIG. 92A                FIG. 92B
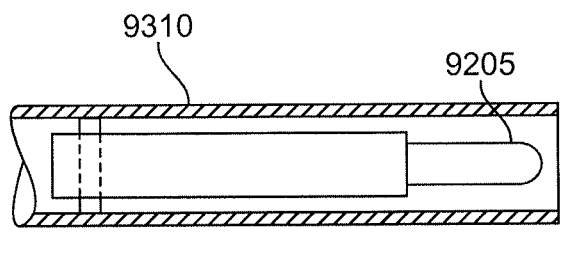 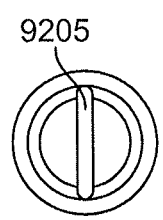
FIG. 93A                FIG. 93B

OCULAR IMPLANT WITH HYDROGEL EXPANSION CAPABILITIES

REFERENCE TO PRIORITY DOCUMENT

This application is a continuation of U.S. application Ser. No. 12/175,294 now U.S. Pat. No. 8,672,870, filed Jul. 17, 2008, which claims priority of U.S. Provisional Patent Application Ser. No. 60/950,315, filed Jul. 17, 2007. The disclosures of the patent applications are hereby incorporated by reference in their entirety.

BACKGROUND

This disclosure relates generally to methods and devices for use in treating glaucoma. The mechanisms that cause glaucoma are not completely known. It is known that glaucoma results in abnormally high pressure in the eye, which leads to optic nerve damage. Over time, the increased pressure can cause damage to the optic nerve, which can lead to blindness. Treatment strategies have focused on keeping the intraocular pressure down in order to preserve as much vision as possible over the remainder of the patient's life.

Past treatment has included the use of drugs that lower intraocular pressure through various mechanisms. The glaucoma drug market is an approximate two billion dollar market. The large market is mostly due to the fact that there are not any effective surgical alternatives that are long lasting and complication-free. Unfortunately, drug treatments need much improvement, as they can cause adverse side effects and often fail to adequately control intraocular pressure. Moreover, patients are often lackadaisical in following proper drug treatment regimens, resulting in a lack of compliance and further symptom progression.

With respect to surgical procedures, one way to treat glaucoma is to implant a drainage device in the eye. The drainage device functions to drain aqueous humour from the anterior chamber and thereby reduce the intraocular pressure. The drainage device is typically implanted using an invasive surgical procedure. Pursuant to one such procedure, a flap is surgically formed in the sclera. The flap is folded back to form a small cavity and the drainage device is inserted into the eye through the flap. Such a procedure can be quite traumatic as the implants are large and can result in various adverse events such as infections and scarring, leading to the need to re-operate.

The following references describe various devices and procedures for treating glaucoma: U.S. Pat. No. 6,827,700 to Lynch, U.S. Pat. No. 6,666,841 to Bergheim, U.S. Pat. No. 6,508,779 to Suson, U.S. Pat. No. 6,544,208 to Ethier, U.S. Pat. No. 5,601,094 to Reiss, U.S. Pat. No. 6,102,045 to Nordquist, United States Patent Application 2002/0156413 to Williams, 2002/0143284 to Tu, 2003/0236483 to Ren, 2002/0193725 to Odrich, 2002/0165478 to Gharib, 2002/0133168 to Smedley, 2005/0107734, 2004/0260228 to Lynch, 2004/0102729 to Haffner, 2004/0015140 to Shields, 2004/0254521 to Simon, and 2004/0225250 to Yablonski. The aforementioned references are all incorporated herein by reference in their entireties.

Current devices and procedures for treating glaucoma have disadvantages and only moderate success rates. The procedures are very traumatic to the eye and also require highly accurate surgical skills, such as to properly place the drainage device in a proper location. In addition, the devices that drain fluid from the anterior chamber to a subconjunctival bleb beneath a scleral flap are prone to infection, and can occlude and cease working. This can require re-operation to remove the device and place another one, or can result in further surgeries. In view of the foregoing, there is a need for improved devices and methods for the treatment of glaucoma.

SUMMARY

Disclosed are devices and methods for treatment of eye disease such as glaucoma. An implant is placed in the eye wherein the implant provides a fluid pathway for the flow or drainage of aqueous humour from the anterior chamber to the suprachoroidal space. The implant is implanted in the eye using a delivery system that uses a minimally invasive procedure, as described below. By guiding fluid directly into the supraciliary or suprachoroidal space rather than to the surface of the eye, complications commonly encountered with conventional glaucoma surgery should be avoided. Implanting aqueous fluid flow directly into the supraciliary or suprachoroidal space should minimize scarring since the angle region is populated with a single line of non-proliferating trabecular cells. Implanting aqueous flow directly into the supraciliary or suprachoroidal space should minimize hypotony and also potentially eliminate complications such as endophthalmitis and leaks since an external filtering bleb is not the goal of surgery. The device described herein is designed to enhance aqueous flow through the normal outflow system of the eye with minimal to no complications. Any of the procedures and device described herein can be performed in conjunction with other therapeutic procedures, such as laser iridotomy, laser iridoplasty, and goniosynechialysis (a cyclodialysis procedure).

In one aspect, there is disclosed an ocular implant, comprising: an elongate member having an internal lumen forming a flow pathway, at least one inflow port communicating with the flow pathway, and at least one outflow port communicating with the flow pathway. The elongate member is adapted to be positioned in the eye such that at least one inflow port communicates with the anterior chamber, at least one outflow port communicates with the suprachoroidal space to provide a fluid pathway between the anterior chamber and the suprachoroidal space when the elongate member is implanted in the eye. The implant further comprises a hydrogel member attached to the elongate member, wherein the hydrogel member is adapted to expand upon implantation of the elongate member in the eye, and an attachment that attaches the hydrogel member to the elongate member.

In another aspect, there is disclosed a method of implanting an ocular device into the eye, comprising: providing an implant having an internal fluid passageway, wherein the implant is at least partially manufactured of an expandable material; inserting the implant into the eye such that a first portion of the fluid passageway communicates with the anterior chamber and a second portion of the fluid passageway communicates with the suprachoroidal space to provide a fluid passageway between the suprachoroidal space and the anterior chamber; and causing the expandable material to expand such that the expandable material seals a fluid passageway adjacent the implant.

In another aspect, there is disclosed a method of implanting an ocular device into the eye, comprising: providing an implant having an internal fluid passageway, wherein the implant includes an actuation member at least partially manufactured of an expandable material; inserting the implant into the eye such that a first portion of the fluid passageway communicates with the anterior chamber and a second portion of the fluid passageway communicates with the suprachoroidal space to provide a fluid passageway between the suprachoroidal space and the anterior chamber; and causing the expandable material to expand such that the actuation member causes a movable portion of the implant to move from a first position to a second position.

In another aspect, there is disclosed method of implanting an ocular device into the eye, comprising: providing an implant having an internal fluid passageway, wherein the implant includes an actuation member at least partially manufactured of an expandable material; inserting the implant into the eye such that a first portion of the fluid passageway communicates with the anterior chamber and a second portion of the fluid passageway communicates with the suprachoroidal space to provide a fluid passageway between the suprachoroidal space and the anterior chamber; and causing the expandable material to expand such that the actuation member causes eye tissue to move from a first position to a second position In another aspect, there is disclosed method of implanting an ocular device into the eye, comprising: providing an implant having an internal fluid passageway, wherein the implant includes an actuation member at least partially manufactured of an expandable material; inserting the implant into the eye such that a first portion of the fluid passageway communicates with the anterior chamber and a second portion of the fluid passageway communicates with the suprachoroidal space to provide a fluid passageway between the suprachoroidal space and the anterior chamber; and causing the expandable material to expand such that a partially enclosed volume is formed within the suprachoroidal space.

Other features and advantages should be apparent from the following description of various embodiments, which illustrate, by way of example, the principles of the invention.

BRIEF DESCRIPTION OF THE DRAWINGS

FIG. 66A shows a side view of an implant prior to expansion.

FIG. 66B shows a front view of the implant of FIG. 66A prior to expansion.

FIG. 67 shows a side view of the implant of FIG. 66A with an anchoring members in the expanded state.

FIGS. 92A-93B show an embodiment of an implant having an expansion member comprised of an expandable wire.

DETAILED DESCRIPTION

Figure 1:
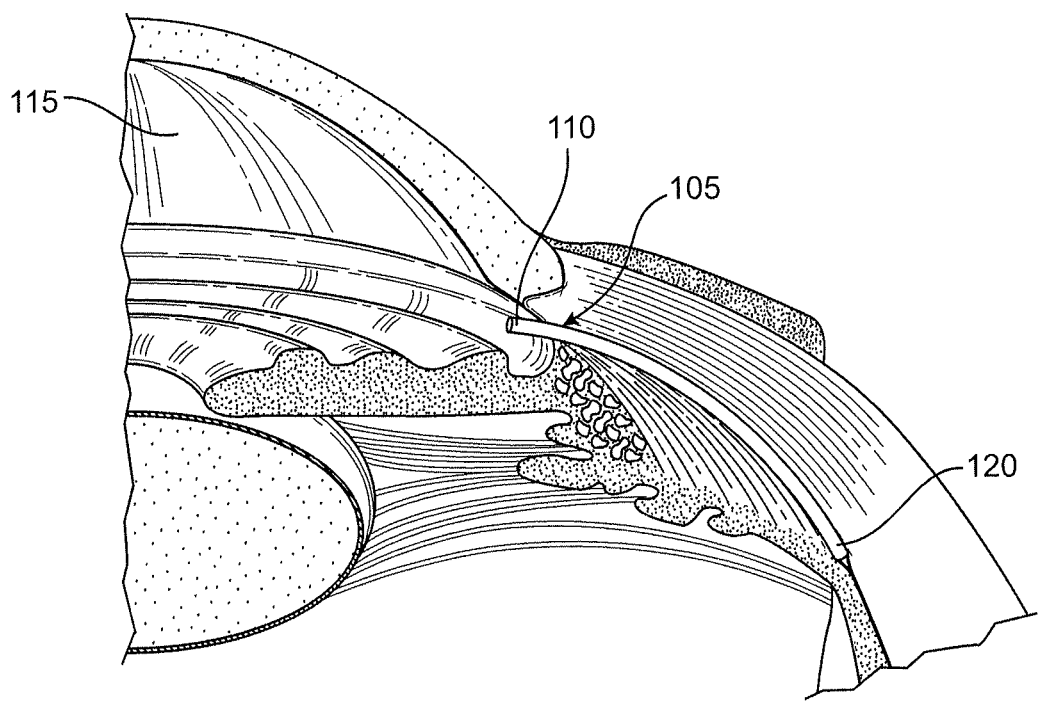
FIG. 1 is a cross-sectional, perspective view of a portion of the eye showing the anterior and posterior chambers of the eye.

FIG. 1 is a cross-sectional, perspective view of a portion of the eye showing the anterior and posterior chambers of the eye. An implant 105 is positioned inside the eye such that a proximal end 110 is located in the anterior chamber 115 and a distal end 120 is located in the suprachoroidal space (sometimes referred to as the perichoroidal space). The implant 105 is illustrated in FIG. 1 as an elongate element having one or more internal lumens through which aqueous humour can flow from the anterior chamber 115 into the suprachoroidal space. Embodiments of the implant 105 with various structural configurations are described in detail below.

Exemplary Eye Anatomy

Figure 2:
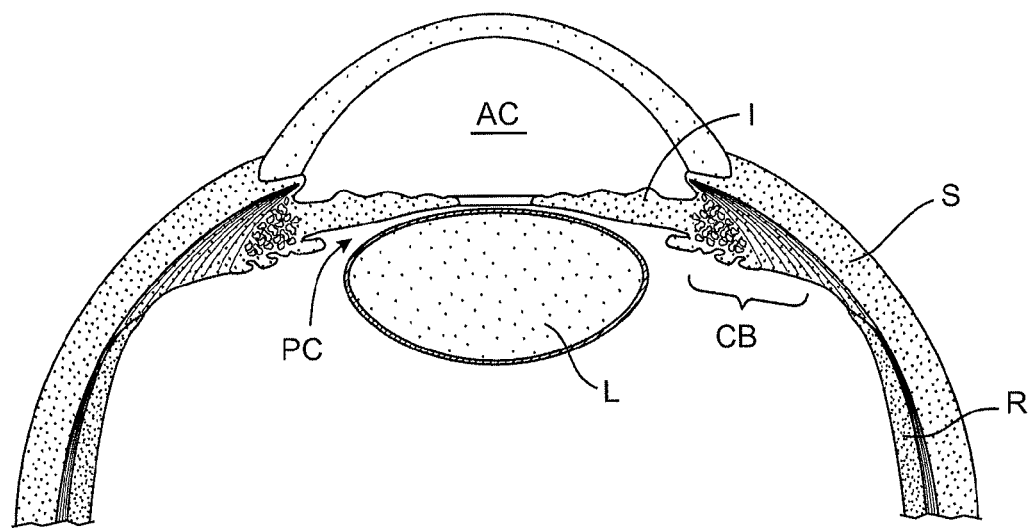
FIG. 2 is a cross-sectional view of a human eye.

FIG. 2 is a cross-sectional view of a human eye. The eye is generally spherical and is covered on the outside by the sclera S. The retina R lines the inside posterior half of the eye. The retina registers the light and sends signals to the brain via the optic nerve. The bulk of the eye is filled and supported by the vitreous body, a clear, jelly-like substance.

The elastic lens L is located near the front of the eye. The lens L provides adjustment of focus and is suspended within a capsular bag from the ciliary body CB, which contains the muscles that change the focal length of the lens. A volume in front of the lens L is divided into two by the iris I, which controls the aperture of the lens and the amount of light striking the retina. The pupil is a hole in the center of the iris I through which light passes. The volume between the iris I and the lens L is the posterior chamber PC. The volume between the iris I and the cornea is the anterior chamber AC. Both chambers are filled with a clear liquid known as aqueous humour.

The ciliary body CB continuously forms aqueous humour in the posterior chamber PC by secretion from the blood vessels. The aqueous humour flows around the lens L and iris I into the anterior chamber and exits the eye through the trabecular meshwork, a sieve-like structure situated at the corner of the iris I and the wall of the eye (the corner is known as the iridocorneal angle). Some of the aqueous humour filters through the trabecular meshwork into Schlemm's canal, a small channel that drains into the ocular veins. A smaller portion rejoins the venous circulation after passing through the ciliary body and eventually through the sclera (the uveoscleral route).

Glaucoma is a disease wherein the aqueous humor builds up within the eye. In a healthy eye, the ciliary processes secrete aqueous humor, which then passes through the angle between the cornea and the iris. Glaucoma appears to be the result of clogging in the trabecular meshwork. The clogging can be caused by the exfoliation of cells or other debris. When the aqueous humor does not drain properly from the clogged meshwork, it builds up and causes increased pressure in the eye, particularly on the blood vessels that lead to the optic nerve. The high pressure on the blood vessels can result in death of retinal ganglion cells and eventual blindness.

Closed angle (acute) glaucoma can occur in people who were born with a narrow angle between the iris and the cornea (the anterior chamber angle). This is more common in people who are farsighted (they see objects in the distance better than those which are close up). The iris can slip forward and suddenly close off the exit of aqueous humor, and a sudden increase in pressure within the eye follows.

Open angle (chronic) glaucoma is by far the most common type of glaucoma. In open angle glaucoma, the iris does not block the drainage angle as it does in acute glaucoma. Instead, the fluid outlet channels within the wall of the eye gradually narrow with time. The disease usually affects both eyes, and over a period of years the consistently elevated pressure slowly damages the optic nerve.

Implant and Delivery System

Figure 3A:
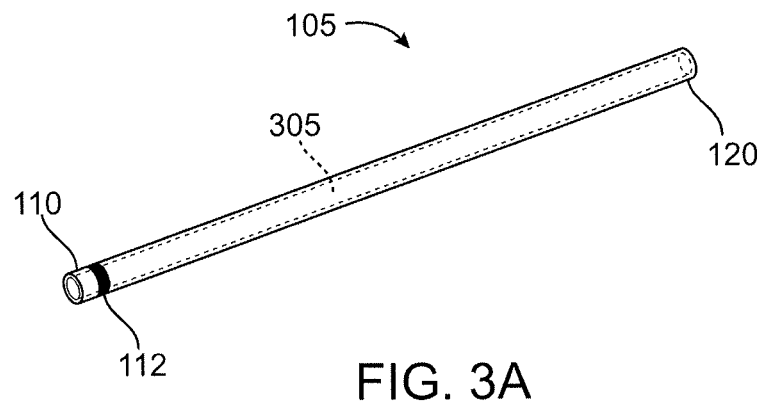
FIG. 3A shows a first embodiment of an eye implant.

FIG. 3A shows a first embodiment of the implant 105. As mentioned, the implant 105 is an elongate member having a proximal end 110, a distal end 120, and a structure that permits fluid (such as aqueous humour) to flow along the length of the implant such as through the implant or around the implant. In the embodiment of FIG. 3A, the elongate member includes at least one internal lumen 305 having at least one opening for ingress of fluid (such as aqueous humor) and at least one opening for egress of fluid. In the embodiment of FIG. 3A, the implant includes a single opening in the proximal end 110 and a single opening in the distal end 120 that both communicate with the internal lumen 305. However, the implant 105 can include various arrangements of openings that communicate with the lumen(s), as described below.

The internal lumen 305 serves as a passageway for the flow of aqueous humour through the implant 105 directly from the anterior chamber to the suprachoroidal space. In addition, the internal lumen 305 can be used to mount the implant 105 onto a delivery system, as described below. The internal lumen 305 can also be used as a pathway for flowing irrigation fluid into the eye generally for flushing or to maintain pressure in the anterior chamber, or using the fluid to hydraulically create a dissection plane into or within the suprachoroidal space. In the embodiment of FIG. 3A, the implant 105 has a substantially uniform diameter along its entire length, although the diameter of the implant can vary along its length, as described below. Moreover, although the implant 105 is shown as having a circular cross-sectional shape, the implant can have various cross-sectional shapes (such as an oval or rectangular shape) and can vary in cross-sectional shape moving along its length. The cross-sectional shape can be selected to facilitate easy insertion into the eye.

The implant 105 can include one or more features that aid in properly positioning the implant 105 in the eye. For example, the implant can have one or more visual, tomographic, echogenic, or radiopaque markers 112 that can be used to aid in placement using any of the devices referenced above tuned to its applicable marker system. In using the markers to properly place the implant, the implant is inserted in the suprachoroidal space, until the marker is aligned with a relevant anatomic structure, for example, visually identifying a marker on the anterior chamber portion of the implant that aligns with the trabecular meshwork, or scleral spur (including below the scleral spur), such that an appropriate length of the implant remains in the anterior chamber. Under ultrasound, an echogenic marker can signal the placement of the device within the suprachoroidal space. Any marker can be placed anywhere on the device to provide sensory feedback to the user on real-time placement, confirmation of placement or during patient follow up. Other structural features are described below.

Figure 4:
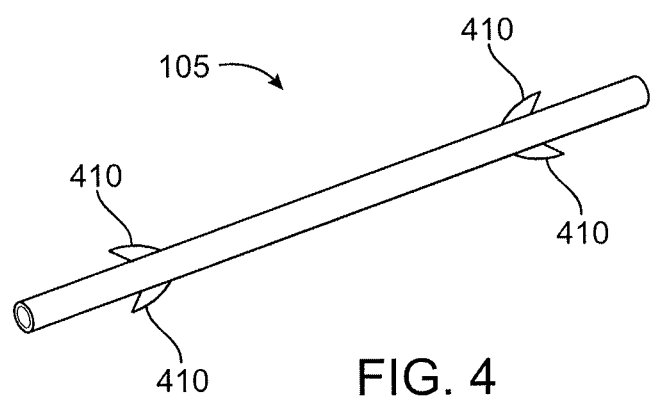
FIG. 4 shows the implant including one or more retention structures.

The implant 105 can also include structural features that aid in anchoring or retaining the implanted implant 105 in the eye. For example, as shown in FIG. 4, the implant 105 can include one or more retaining or retention structures 410, such as protrusions, wings, tines, or prongs, that lodge into anatomy to retain the implant in place. The retention structures 410 can be deformable or stiff. The retention structures 410 can be made of various biocompatible materials. For example, the retention structures 410 can be made from thin 0.001" thick polyimide, which is flexible, thin 0.003" silicone elastomer which is also flexible, or stainless steel or Nitinol. Alternatively, the retention structures 410 could be rings of polyimide. It should be appreciated that other materials can be used to make the retention structures 410. The shape of retention structures 410 can vary. For example, FIG. 4 shows the retention structures 410 as barb-shaped with pointed edges of the barbs pointing in opposite directions. In other embodiments, the retention structures 410 can be rectangular, triangular, round, combinations thereof, or other shapes. Additional embodiments of retention structures 410 are described below.

Other anchoring or retaining features can be employed with the implant 105. For example, one or more hairs, such as human hairs, or synthetic hairs made from polymers, elastomers or metals can be attached to the implant. The hairs can be glued or thermally bonded to the implant. The hairs, if they are polyimide, can be attached to the implant by dipping and polymerized by heat and pressure if the dipping material is polyimide. The hairs can be crimped to the implant by rings. Alternatively, the implant can have through-hole features that the hairs can be threaded through and tied or knotted. The hairs can be overmolded onto the implant body. The hairs are positioned relative to the implant such that at least a portion of the hair extends outwardly from the implant for anchoring within or against the tissue of the eye. Various anchoring and retaining features are described herein and it should be appreciated that the features can be implemented in any of the implant embodiments described herein.

The retaining features, such as wings or collars, can be manufactured by various methods. In one embodiment, the retaining features can be inherent in the raw material from which the implant is constructed. The implant can be machined or laser ablated from a unitary rod or block of stock of material with the material subtracted or removed, leaving the retaining features behind.

Alternatively, the retaining features can be manufactured as separate parts and assembled onto the implant. They can be joined to the implant by a friction fit or attached with biocompatible adhesives. They can fit into grooves, holes or detents in the body of the implant to lock them together. If the retaining features are constructed from hairs or sutures, they can be threaded or tied onto the implant. Alternatively, the retaining features can be overmolded onto the implant via an injection molding process. Alternatively, the entire implant and retention features can be injection molded in one step. Alternatively, the retaining features can be formed into the implant with a post-processing step such as flaring or thermoforming parts of the implant.

The implant 105 can be made of various materials, including, for example, polyimide, Nitinol, platinum, stainless steel, molybdenum, or any other suitable polymer, metal, metal alloy, or ceramic biocompatible material or combinations thereof. Other materials of manufacture or materials with which the implant can be coated or manufactured entirely include Silicone, PTFE, ePTFE, differential fluoropolymer, FEP, FEP laminated into nodes of ePTFE, silver coatings (such as via a CVD process), gold, prolene/polyolefins, polypropylene, poly(methyl methacrylate) (PMMA), acrylic, PolyEthylene Terephthalate (PET), Polyethylene (PE), PLLA, and parylene. The implant 105 can be reinforced with polymer, Nitinol, or stainless steel braid or coiling or can be a co-extruded or laminated tube with one or more materials that provide acceptable flexibility and hoop strength for adequate lumen support and drainage through the lumen. The implant can alternately be manufactured of nylon (polyamide), PEEK, polysulfone, polyamideimides (PAI), polyether block amides (Pebax), polyurethanes, thermoplastic elastomers (Kraton, etc), and liquid crystal polymers.

Any of the embodiments of the implant 105 described herein can be coated on its inner or outer surface with one or more drugs or other materials, wherein the drug or material maintains the patency of the lumen or encourages in-growth of tissue to assist with retention of the implant within the eye or to prevent leakage around the implant. The drug can also be used for disease treatment. The implant can also be coated on its inner or outer surface with a therapeutic agent, such as a steroid, an antibiotic, an anti-inflammatory agent, an anticoagulant, an antiglaucomatous agent, an anti proliferative, or any combination thereof. The drug or therapeutic agent can be applied in a number of ways as is known in the art. Also the drug can be embedded in another polymer (nonabsorbable or bioabsorbable) that is coated on the implant.

The implant can also be manufacture of, coated or layered with a material that expands outward once the implant has been placed in the eye. The expanded material fills any voids that are positioned around the implant. Such materials include, for example, hydrogels, foams, lyophilized collagen, or any material that gels, swells, or otherwise expands upon contact with body fluids.

The implant can also be covered or coated with a material (such as polyester, ePTFE (also known as GORETEX®), PTFE that provides a surface to promote healing of the implant into the surrounding tissue. In order to maintain a low profile, well-known sputtering techniques can be employed to coat the implant. Such a low profile coating would accomplish a possible goal of preventing migration while still allowing easy removal if desired.

Figure 3B:
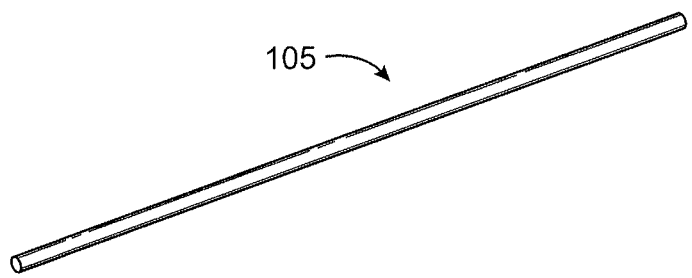
FIG. 3B shows an implant formed of an elongate wick member through which fluid can flow.

In another embodiment shown in FIG. 3B that can be useful in some glaucoma cases depending on how much flow is desired, the implant 105 is formed of an elongate wick member through which fluid can flow. The wick member can be formed of a single strand of material or can be formed of a plurality of strands that are interconnected, such as in a twisted, braided, or woven fashion, and through or along which fluid can flow. The wick member(s) do not necessarily include internal lumens, as flow through the wick member can occur via capillary action. In the case of a solid polymer wick, certain surface detents can provide flow lumens between the central body member and the tissue of the suprachoroidal space.

Figure 3C:
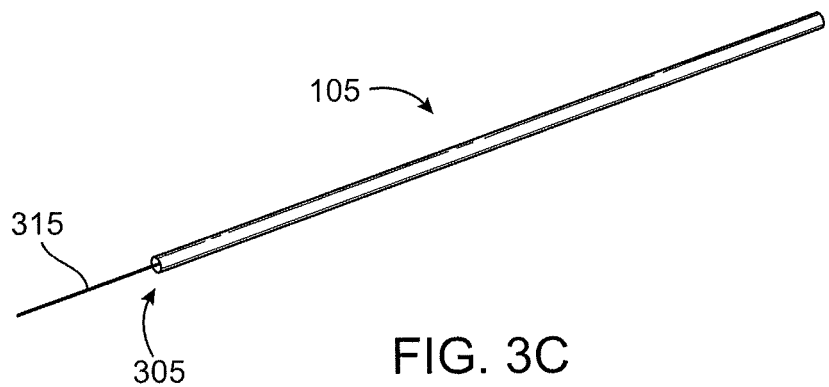
FIG. 3C shows an implant that combines a tube and a wicked member.

The features of the implants shown in FIGS. 3A and 3B can be combined as shown in FIG. 3C. Indeed, any of the structural or method features described herein can be combined with any other structural or method features. Thus, the implant 105 can include one or more wick members 315 in fluid communication with an internal lumen 305 (or external lumen) of an elongate member. The flow of aqueous humour occurs both through the internal lumen 305 and through or along the wick member 315.

In an exemplary embodiment, the implant has a length in the range of 0.1" to 0.75" and an inner diameter for a flow path in the range of 0.002" to 0.015". In an embodiment, the inner diameter is 0.012", 0.010", or 0.008". A wicking implant can have a diameter in the range of 0.002" to 0.025". In the event that multiple implants are used, and for example each implant is 0.1", the fully implanted device can create a length of 0.2" to 1.0", although the length can be outside this range. An embodiment of the implant is 0.250" long, 0.012" in inner diameter, and 0.015" in outer diameter. One embodiment of the implant is 0.300" long.

The implant 105 has a column strength sufficient to permit the implant 105 to be inserted into suprachoroidal space such that the distal tip of the implant 105 tunnels through the eye tissue (such as the ciliary body) without structural collapse or structural degradation of the implant 105. In addition, the surface of the inner lumen 305 is sufficiently smooth relative to the delivery device (described in detail below) to permit the implant 105 to slide off of the delivery device during the delivery process. In an embodiment, the column strength is sufficient to permit the implant to tunnel through the eye tissue into the suprachoroidal space without any structural support from an additional structure such as a delivery device.

The implant 105 can be configured to transition between a first state of reduced size and a second state of expanded size and vice-versa. For example, the implant 105 can be in a first state wherein the implant 105 has a reduced radial size and/or overall length in order to facilitate fitting the implant through a small portal during delivery. The implant can then transition to a second state of increased radial size and/or overall length. The implant can also change cross sectional shape along the length. The transition in shape can occur during delivery of the implant while the implant is moving through the eye to a delivery location. Alternately, the implant can begin to change shape after the implant is in the desired location in the eye.

The transition between the first and second states can be implemented in various manners. For example, the implant can be manufactured of a material such as Nitinol that deforms in response to temperature variations or a release of a constraining element. Thus, the implant can be self-expanding or self-restricting at various locations along the length. In another embodiment or in combination with a self-expanding implant, the implant can be expanded manually, such as through use of an expansion balloon or by passing the implant along a pre-shaped device, such as a reverse-tapered delivery trocar that increases in diameter. In addition, the implant can be positioned inside a sheath during delivery wherein the sheath maintains the implant in the first state of reduced size. Upon delivery, the sheath can be removed to permit the implant to expand in size, such as in a manner described herein.

Figure 5:
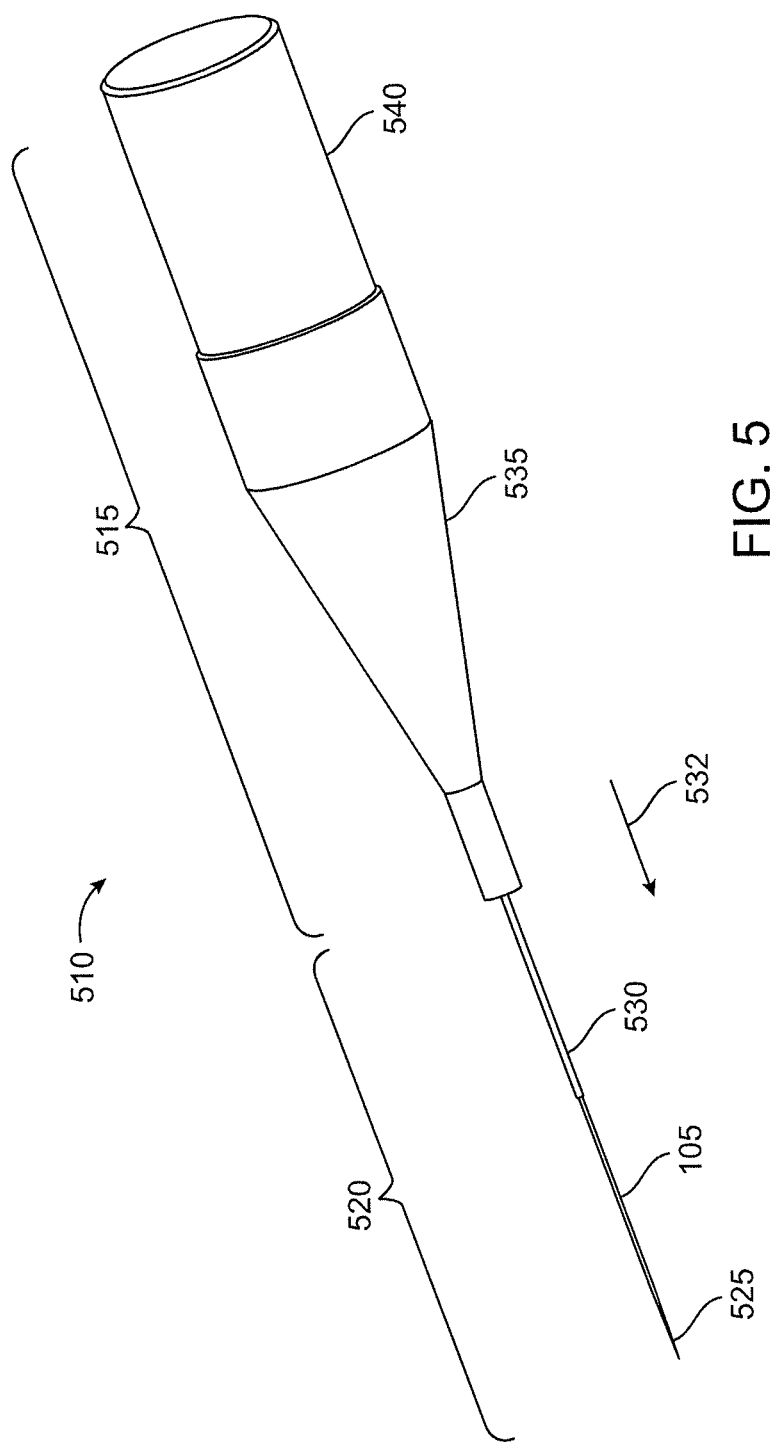
FIG. 5 shows an exemplary embodiment of a delivery system that can be used to deliver the implant into the eye.

FIG. 5 shows an exemplary delivery system 510 that can be used to deliver the implant 105 into the eye pursuant to methods described in detail below. The delivery system 510 includes a handle component 515 that controls an implant placement mechanism, and a delivery component 520 that removably couples to the implant 105 for delivery of the implant 105 into the eye. The delivery component 520 includes an elongate applier 525. In one embodiment, the applier 525 has a sharpened distal tip. The applier 525 is sized to fit through the lumen in the implant 105 such that the implant 105 can be mounted on the applier 525. The applier 525 can have a cross-sectional shape that complements the cross-sectional shape of the internal lumen of the implant 105 to facilitate mounting of the implant onto the applier 525. It should be appreciated the applier 525 does not have to employ a sharpened distal tip. The applier 525 can have an atraumatic or blunt distal tip such that it serves as a component for coupling to the implant, or performing blunt dissection, rather than as a cutting component.

The delivery component 520 also includes an implant deployment or advancing structure 530 positioned on a proximal end of the applier 525. The advancing structure 530 can be an elongated tube that is positioned over the applier 525. The delivery system 510 can be actuated to achieve relative, sliding movement between the advancing structure 530 and the applier 525. For example, the advancing structure 520 can be moved in the distal direction (as represented by the arrow 532), while the applier 525 remains stationary to push or otherwise advance the implant 105 along the applier 525 for delivery of the implant 105 into the eye. In an alternate embodiment, the applier 525 withdraws distally into the advancing structure 530 to remove the implant 105 from the applier 525, as described below with reference to FIG. 6B. In yet another embodiment, both the advancing structure 530 and the applier 525 move relative to one another to remove the implant 105.

In an embodiment, the applier 525 can have a length sufficient to receive a plurality of implants in an end-to-end series arrangement on the applier 525. In this manner, multiple implants 105 can be loaded onto the applier 525 and delivered one at a time such that the implants collectively form an elongated lumen of sufficient length for adequate drainage. This permits relatively short length implants that can be collectively used in various eye sizes. In addition, multiple implants can be placed in multiple separate locations within one eye.

The applier 525 or any portion of the delivery component 520 can have an internal lumen that extends along its length for receipt of a guidewire that can be used during delivery of the implant 105. The internal lumen in the delivery component 520 can also be used for the flow of fluid in order to irrigate the eye. The internal lumen can be sufficiently large to receive the implant 105 such that the implant 105 is mounted inside the applier 525, rather than over the applier 525, during delivery.

The handle component 515 of the delivery system 510 can be actuated to control delivery of the implant 105. In this regard, the handle component 515 includes an applier control 540 that can be actuated to cause the applier 525 to extend in length in the distal direction or to retract in the opposite direction (proximal direction). The handle component 515 also includes an implant advancing actuator 535 that can be actuated to selectively move the advancing structure 530 along the applier 525 in the proximal or distal direction. In this manner, the advancing structure 530 can be used to push the implant 105 in the distal direction and off of the applier 525 during delivery, or else to hold the implant 105 in a fixed location in the eye while the applier 525 is withdrawn.

The handle component 515 can be adapted such that it can be actuated using only a single hand. In addition, the delivery system 510 can include an actuation member that is separate from the handle 515 such that the operator can use a foot to actuate the delivery system 510. For example, a foot pedal or hydraulics can be coupled to or incorporated within the delivery system 510 to save the use of the physician's hand at the worksite. Thus, the physician simply positions a cannula or delivery system with his or her hands and uses the foot pedal to advance the implant. PCT Publication No. WO06012421, which is incorporated herein by reference in its entirety, describes an exemplary hydraulic assist for an ablation catheter with a steerable tip.

In another embodiment, some of the functions of the applier 525 and the implant 105 are combined. That is, the distal tip of the implant 105 can have a pointed or other type of shape (such as a beveled or blunted shape) on the distal end that facilitates penetration of the implant 105 through tissue. Exemplary methods for delivering the implant 105 into the eye are described in detail below.

As mentioned, the applier 525 can be equipped with one or more mechanisms that cause expansion of the implant 105. For example, the applier 525 can include an expandable structure, such as an inflatable sheath, that is mounted over a solid core of the applier 525. The inflatable sheath is positioned at least partially within the internal lumen of the implant 105 when the implant 105 is mounted on the applier 525. During delivery of the implant 105, the inflatable sheath is expanded when the implant 105 is positioned in the appropriate location in the eye to expand the implant 105 and cause the implant 105 to lodge in the location. The sheath is then deflated or otherwise reduced in size to permit the applier 525 to be withdrawn from the implant 105. Exemplary methods are described below.

Figure 6A:
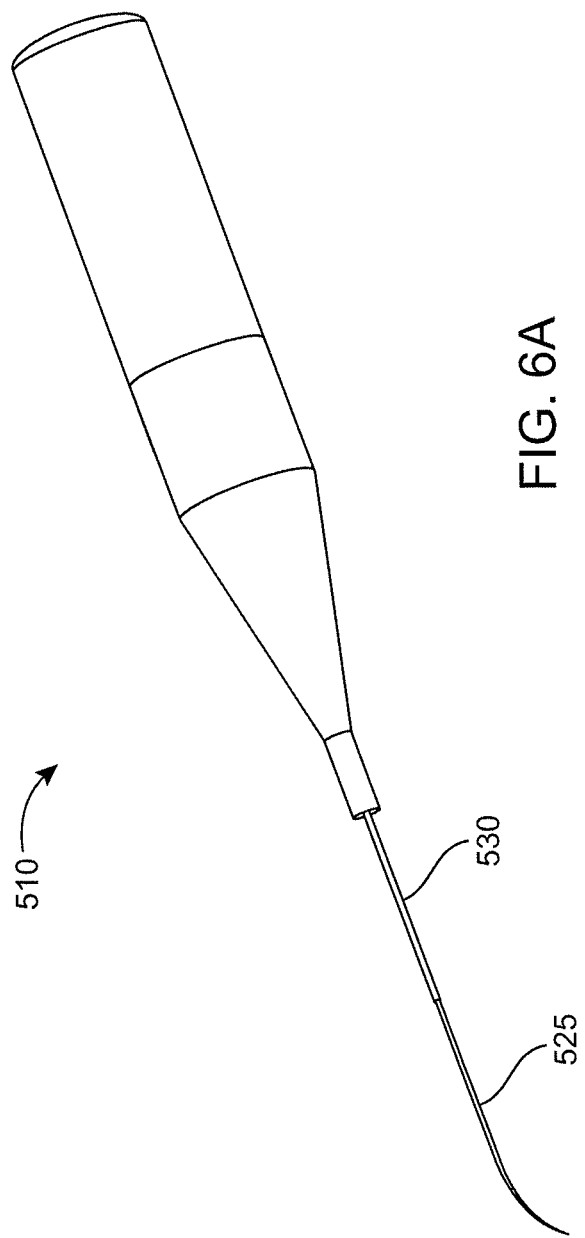
FIG. 6A shows another embodiment of a delivery system.

The applier 525 can be made of various materials, including, for example, stainless steel and Nitinol. The applier 525 can be straight (as shown in FIG. 5) or the applier 525 can be curved along all or a portion of its length (as shown in FIG. 6A) in order to facilitate proper placement through the cornea. In this regard, the curvature of the applier 525 can vary. For example, the applier 525 can have a radius of curvature of 3 mm to 50 mm and the curve can cover from 0 degrees to 180 degrees. In one embodiment, the applier 525 has a radius of curvature that corresponds to or complements the radius of curvature of a region of the eye, such as the suprachoroidal space. For example, the radius of curvature can be around 12 mm. Moreover, the radius of curvature can vary moving along the length of the applier 525. There can also be means to vary the radius of curvature of portions of the applier 525 during placement.

The applier can also have a structure that enables or facilitates use of the applier 525. For example, the distal tip of the applier 525 can have a shape that facilitates blunt dissection of targeted tissue such as to facilitate dissection into the suprachoroidal space. In this regard, the distal tip of the applier 525 can have a flat, shovel, spade, etc. shape, for example.

Figure 6B:
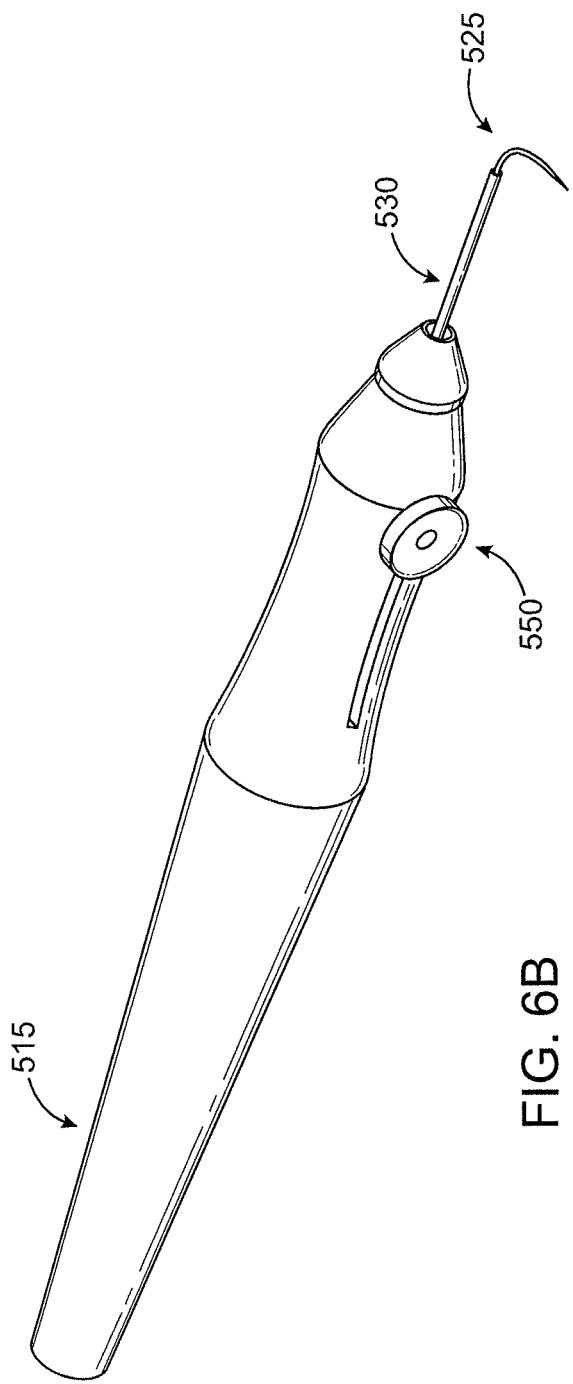
FIG. 6B shows another embodiment of a delivery system.
Figure 6C:
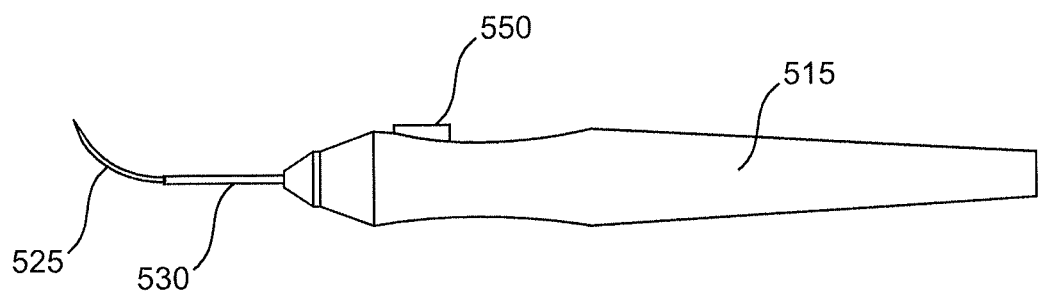
FIGS. 6C and 6D show the delivery system of FIG. 6B during actuation.
Figure 6D:
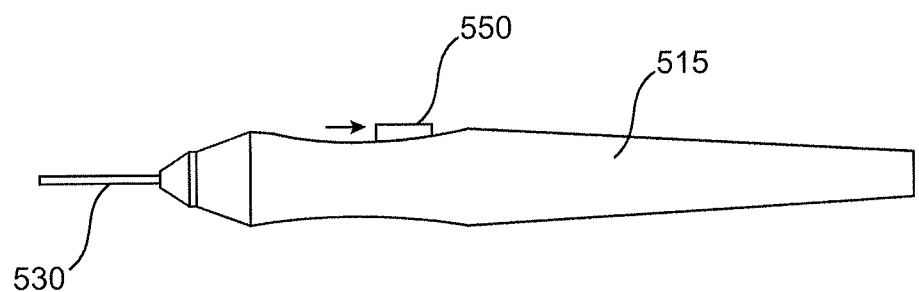

FIG. 6B shows another embodiment of the delivery device 510. The handle component 515 includes an actuator comprised of a knob 550 that can slide relative to the handle component 515. The knob 550 serves as an actuator that controls relative, sliding movement between the advancing member 530 and the applier 525. For example, with reference to FIGS. 6C and 6D, the advancing member 530 can be fixed relative to the handle component 515. In a first state shown in FIG. 6C, the applier 525 is extended outwardly relative to the advancing member 530. Movement of the knob 550, such as in the proximal direction, causes the applier 525 to slide proximally into the advancing element 530 as shown in FIG. 6D.

Figure 6E:
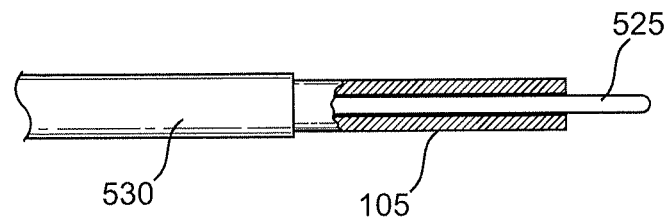
FIGS. 6E-6G show a distal region of the delivery system during various stages of actuation.
Figure 6F:
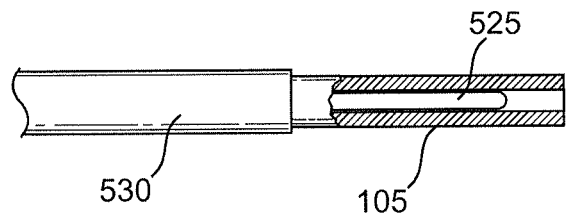
Figure 6G:
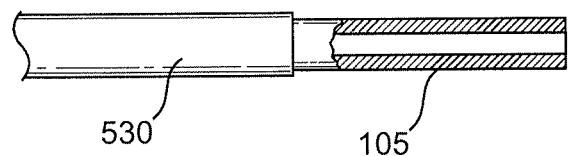

This is described in more detail with reference to FIG. 6E, which shows the implant 105 mounted on the applier 525 distal of the advancing structure 530. When the knob 550 is actuated, the applier 525 slides in the proximal direction and into the advancing structure 530, as shown in FIG. 6F. The proximal edge of the implant 105 abuts the distal edge of the advancing structure 530 to prevent the implant 105 from sliding in the proximal direction. Thus, the applier 525 gradually withdraws from the implant 105. As shown in FIG. 6G, the applier 525 can be fully withdrawn into the advancing structure 530 such that the implant 105 is released from the applier 525.

Figure 6H:
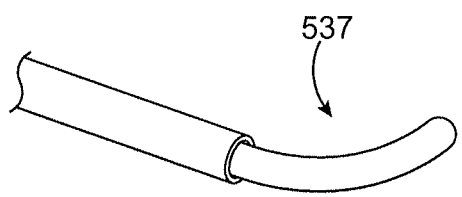
FIG. 6H shows an enlarged view of an exemplary distal region of an applier of the delivery system.

FIG. 6H shows an enlarged view of an exemplary distal region 537 of the applier 525. The distal region 537 of the applier 525 can be shaped to facilitate an approach into the suprachoroidal space. In this regard, as mentioned above, the distal region 537 can have a curved contour that compliments the curved contour of the dissection plane, such as the suprachoroidal space.

At least a portion of the applier 525 can be flexible. For example, the distal region 537 of the applier 525 can be flexible such that it conforms to the shape of the implant 105 when the implant 105 is mounted on the distal region 537. The distal region 537 can also conform to the shape of the advancing element 530 when the applier 525 is withdrawn into the advancing element 530. In an embodiment, the stiffness of the applier varies along the length of the applier.

Various other embodiments of the implant 105 are now described. The reference numeral 105 is used to refer to all embodiments of the implant and it should be appreciated that features in the various embodiments can be combined with other embodiments. As mentioned, the implant 105 can include various types of structures and mechanisms for retaining or otherwise anchoring the position of the implant 105 in the eye. For example, the implant 105 can be equipped with a structure (such as a mesh structure or spray coating) that facilitates endothelial growth of tissue around the implant for permanent placement of the implant.

Figure 7:
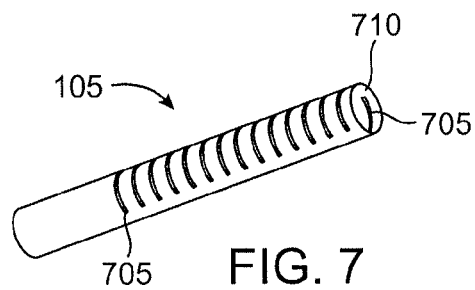
FIG. 7 shows an enlarged view of an end region of the implant.

FIG. 7 shows an enlarged view of an end region, such as the distal end region, of the implant 105. The end region includes retaining structures comprised of one or more fenestrations, slits or slots 705 located on the implant 105. The slots 705 are shown arranged in a series along the end region of the implant 105, although it should be appreciated that the spatial configuration, size, and angle of the slots 705 can vary. The implant 105 shown in FIG. 7 has a distal wall 710 that at least partially encloses the distal end of the internal lumen. The distal wall 710 can have a slot 705 for fluid flow into and out of the lumen. Alternately, the distal wall 710 can be absent such that an opening is present for the flow of fluid. The slots can operate to allow fluid flow in addition to the central lumen of the implant 105.

The slots 705 form edges that interface with surrounding tissue to prevent the implant 105 from becoming dislodged once implanted in the eye. The slots 705 form holes that communicate with the internal lumen of the implant 105 for inflow and outflow of aqueous humour relative to the lumen. The proximal end of the implant can also be equipped with an arrangement of slots 705.

Figure 8:
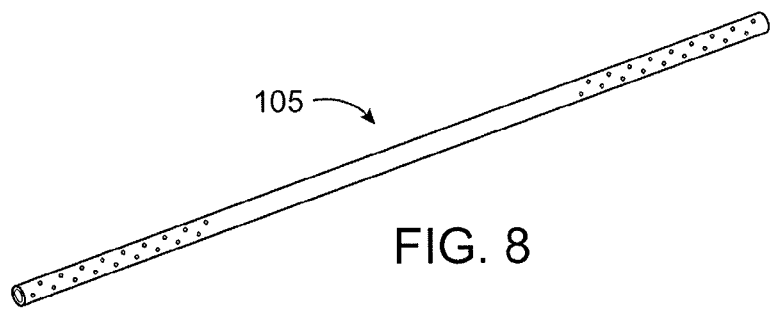
FIG. 8 shows another embodiment of the implant wherein a plurality of holes are located on the side walls of the implant.

FIG. 8 shows another embodiment of the implant 105 wherein a plurality of holes are located on the side walls of the implant 105 and interspersed along the length of the implant 105. The holes facilitate the flow of fluid into and out of the internal lumen of the implant 105. The implant 105 can be configured such that it initially does not have any holes. After the implant 105 is placed in the eye, one or more holes can be formed in the implant, such as by applying a laser (e.g., a YAG laser) to the implant 105 or using other means to form the holes.

Each of the holes can communicate with a separate flow path that extends through the implant 105. That is, the implant 105 can include a plurality of internal lumens wherein each internal lumen communicates with one or more of the holes in side wall of the implant.

Figure 9A:
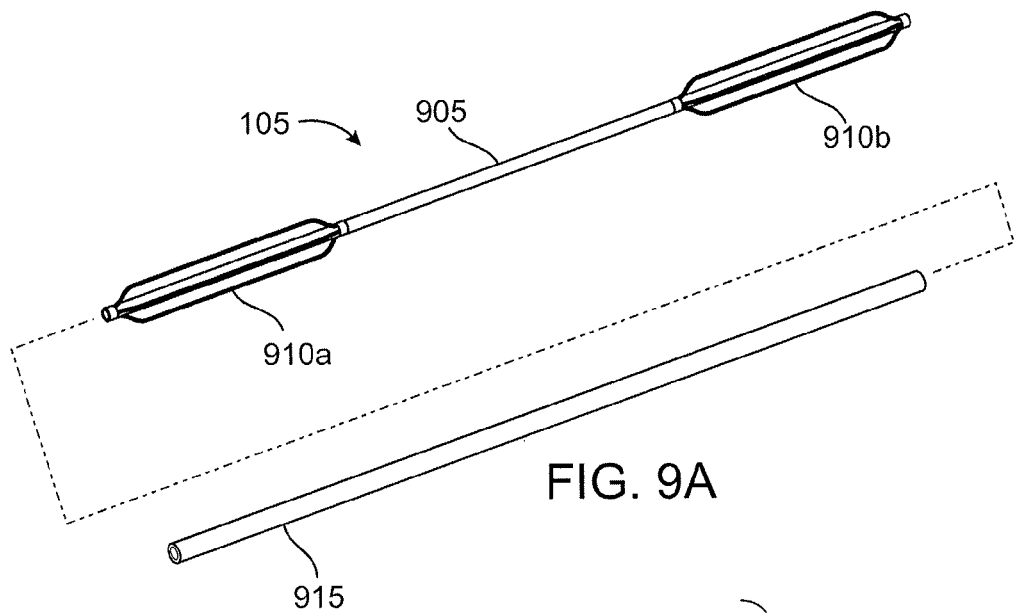
FIG. 9A shows another embodiment of the implant that includes an elongate portion of fixed size and one or more expansion members.

FIG. 9A shows another embodiment of the implant 105 that includes an elongate portion 905 of fixed size and one or more expansion members 910. The elongate portion 905 includes an internal lumen and one or more openings for ingress and egress of fluid relative to the lumen. The expansion members 910 are configured to transition between a first state of reduced size and a second state of expanded or increased size. The structure of the expansion members 910 can vary. In the illustrated embodiment, each expansion member 910 is formed of a plurality of axially-extending rods or tines that are connected at opposed ends. The rods can deform outward along their length to expand the radial size of the expansion member 910. The expansion of the expansion members 910 can be implemented in various manners, such as by using an expansion balloon or by manufacturing the expansion members of a material such as Nitinol that deforms or expands in response to temperature variations or a retractable sheath 915 that allows expansion of an implant formed from a resilient material. The expansion members can also be biased outward such that they self-expand when unrestrained.

Figure 9B:
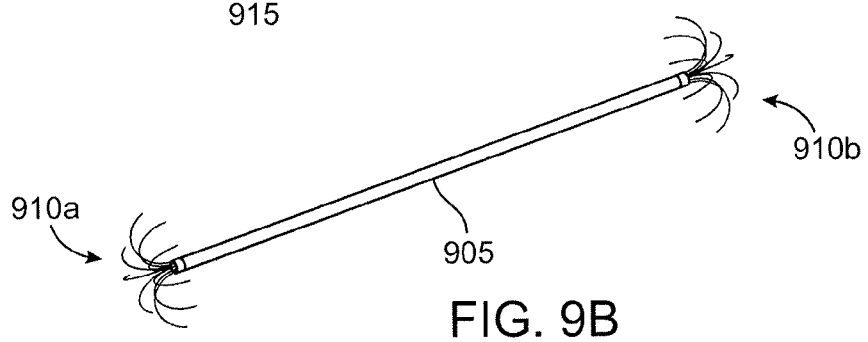
FIG. 9B shows an embodiment of the expansion members that are formed of splayed tines.

As shown in FIG. 9B, an embodiment of the expansion members 910 are formed of tines that are splayed or fanned outward. The tines are configured to hold tissue of the suprachoroidal space open. Either one or both of the expansion members 910 can include splayed tines. For example, the expansion member 910a can be as configured in FIG. 9A, while the expansion member 910b can be as configured in FIG. 9B (or vice-versa). Furthermore, the implant can include three or more expansion members.

The expansion members 910 can be biased toward the expanded state such that, when unopposed, the expansion members 910 automatically move toward the expanded state. In such a case, each of the expansion members 910 can be positioned within a sheath 915 during delivery, wherein the sheath 915 maintains the expansion members 910 in the reduced-size state. The sheath 915 is removed from the expansion members to permit the expansion members 910 to self-expand. The sheath 915 can have a strong hoop and tensile strength to hold the expansion members 910 in an unexpanded state until the implant 105 in a proper place in the eye. In one embodiment, the sheath 915 is manufactured of PolyEthylene Terephthalate (PET).

The embodiment of FIG. 9A includes a first expansion member 910a on a distal end of the implant 105 and a second expansion member 910b on a proximal end of the implant 105. It should be appreciated that the quantity and location of the expansion members 910 on the implant can vary. For example, the implant 105 can include only a single expansion member 910 on either the proximal end or the distal end, or could include one or more expansion members interspersed along the length of the portion 905. Expansion members can be configured in other geometries e.g. latticed, coiled or combinations of each.

Figure 10:
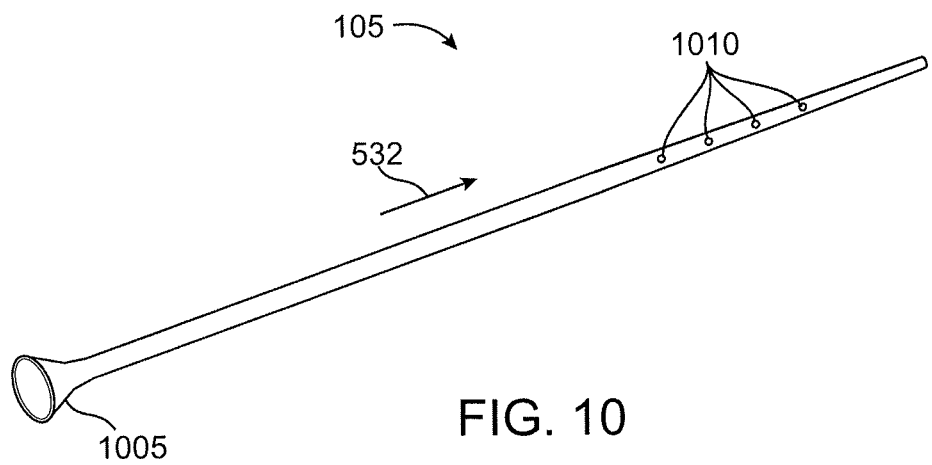
FIG. 10 shows another embodiment of the implant that includes a retaining member located on the proximal end of the implant.

FIG. 10 shows another embodiment of the implant 105 that includes a retaining member 1005 located on the proximal end of the implant 105. The retaining member 1005 has an enlarged size with respect to the remainder of the implant and has a shape that is configured to prevent the implant from moving further into the suprachoroidal space after being properly positioned. The enlarged shape of the retaining member 1005 can lodge against tissue to prevent movement of the implant 105 into or out of a predetermined location, such as the suprachoroidal space. The retaining member 1005 of FIG. 10 has a funnel or cone-like shape, although the retaining member 1005 can have various shapes and sizes that are configured to prevent the implant from moving further into the suprachoroidal space. For example, the retaining member 1005 can have a plate or flange-like shape.

The implant 105 of FIG. 10 is tapered moving along its length such that the diameter of the implant 105 gradually reduces moving in the distal direction. The distal direction is represented by the arrow 532 in FIG. 10. The tapered configuration can facilitate a smooth insertion into the eye. The taper can exist along the entire length of the implant or it can exist only along one or more regions, such as a distal region. Further, the implant can have a bulbous section at approximately its midpoint to create an additional means to anchor. The bulbous section can be an expandable member or balloon element. Implants with bulbous sections are described in detail below.

As mentioned, the implant 105 includes an internal lumen. The lumen can have a uniform diameter along the length of the implant or that can vary in diameter along the length of the implant. In this regard, the diameter of the internal lumen can taper in a manner that achieves a desired fluid flow rate through the implant. Thus, the diameter of the lumen can be varied to regulate fluid flow through the implant. Flow regulation can also be achieved by variation in size, quantity, and/or position of holes 1010 in the distal region of the implant 105, wherein the holes 1010 communicate with the internal lumen. Thus, the holes 1010 can have shapes, sizes, and quantities that are selected to achieve a desired intraocular pressure of the eye as a result of the flow of aqueous humour through the implant. In addition, the use of multiple holes permit fluid to flow, including the implant 105 even when one of the holes 1010 is blocked.

During delivery of the implant 105, the holes 1010 can be positioned so as to align with predetermined anatomical structures of the eye. For example, one or more holes 1010 can align with the suprachoroidal space to permit the flow of aqueous humour into the suprachoroidal space, while another set of holes 1010 aligns with structures proximal to the suprachoroidal space, such as structures in the ciliary body or the anterior chamber of the eye. The implant can have visual markers along its length to assist the user in positioning the desired portion of the implant within the anterior chamber. Further, the implant and delivery system can employ alignment marks, tabs, slots or other features that allow the user to know alignment of the implant with respect to the delivery device.

Figure 11:
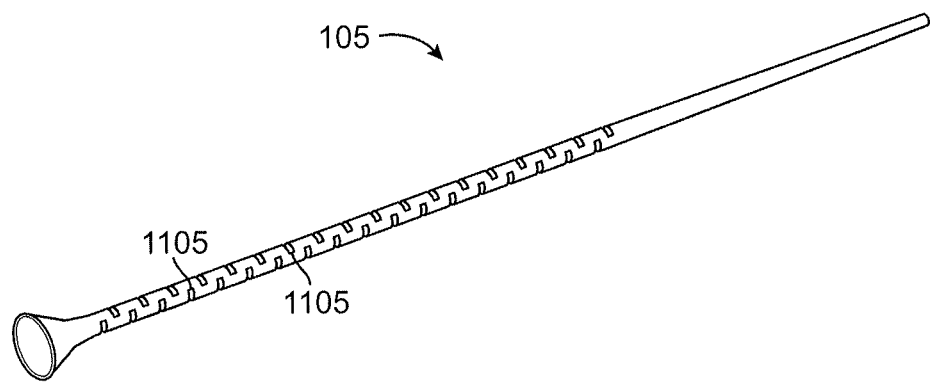
FIG. 11 shows an embodiment of the implant that includes one or more slots.

FIG. 11 shows an embodiment of the implant 105 that includes one or more slots 1105 that are positioned around the circumference of the implant. The slots 1105 provide variations in the implant structure that permit the implant to flex during delivery such as to enable proper placement of the implant 105 from the anterior chamber of the eye to the suprachoroidal space. The implant 105 can also be manufactured of a flexible material with or without slots 1105.

The implant 105 can have other features that provide flexibility to the implant. For example, the implant can be scored or laser cut for flexibility at various locations along the implant. The scores can be located at various positions along the length of the implant 105 to provide localized variation in the flexibility of the implant. For example, a distal region can have a plurality of scores to provide increased flexibility, while a proximal region includes a reduced number of scores that provide less flexibility than the distal region.

Figure 12:
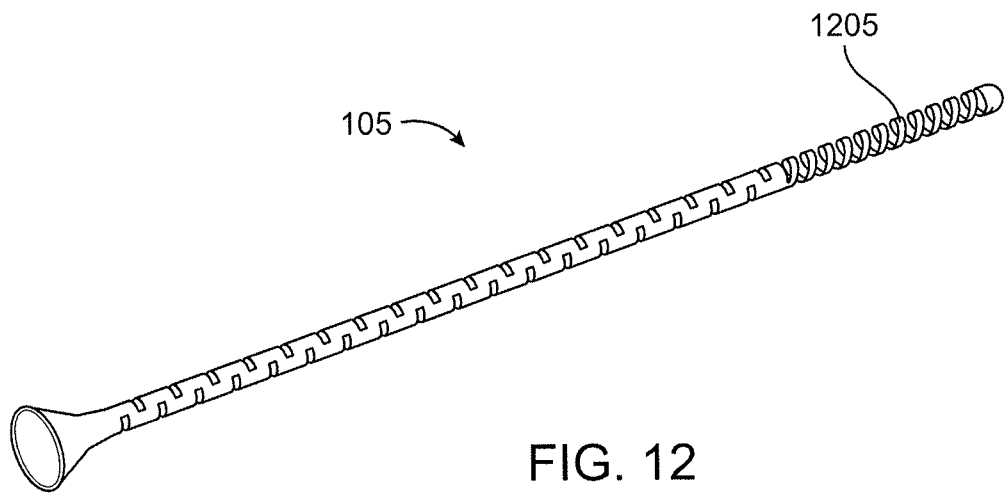
FIG. 12 shows an embodiment of the implant that includes a distal coil member.
Figure 13:
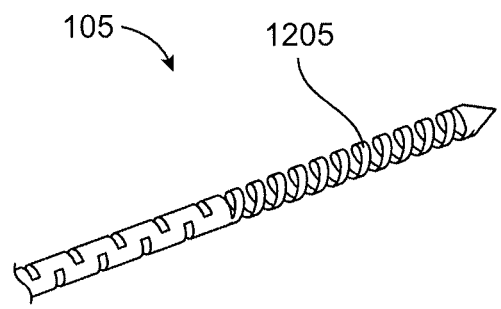
FIG. 13 shows a distal region of an embodiment of the implant that includes a distal coil member and a sharpened distal end.

FIG. 12 shows an embodiment of the implant 105 that includes a distal coil member 1205. The coiled configuration of the coil member 1205 provides increased flexibility to the distal region of the implant 105 to facilitate traction into the suprachoroidal space. Moreover, the coil member 1205 can facilitate fluid flow from the internal lumen into the suprachoroidal space. The coil member 1205 can permit a screwing motion to advance and/or secure the implant 105 in the eye. The distal tip of the implant 105 can have an atraumatic shape, such as a ball shape (as shown in FIG. 12). The distal tip can alternately have a sharpened tip and a shape with barbs that retains the implant in the eye, as shown in FIG. 13. Any of the features that are described herein as being on the distal tip could also be located on the proximal tip of the implant.

Exemplary Methods of Delivery and Implantation

An exemplary method of delivering and implanting the implant into the eye is now described. In general, the implant is implanted using the delivery system by accessing the scleral spur to create a low profile dissection in the tissue plane between the choroid and the sclera. The implant is then secured in the eye so that it provides communication between the anterior chamber and the suprachoroidal space. In an embodiment, a blunt tipped delivery instrument dissects the tissue boundary between the sclera and the ciliary body wherein the dissection entry point starts just below (posterior) the scleral spur. The combination of blunt tipped instrument and approach allows the procedure to be performed "blind" as the instrument tip follows the inner curve of the sclera to dissect the tissue and create a mini cyclodialysis channel to connect the anterior chamber to the suprachoroid. The delivery instrument is inserted through a small incision in the cornea and reached across the eye to the starting point of the dissection just below the scleral spur.

Figure 14:
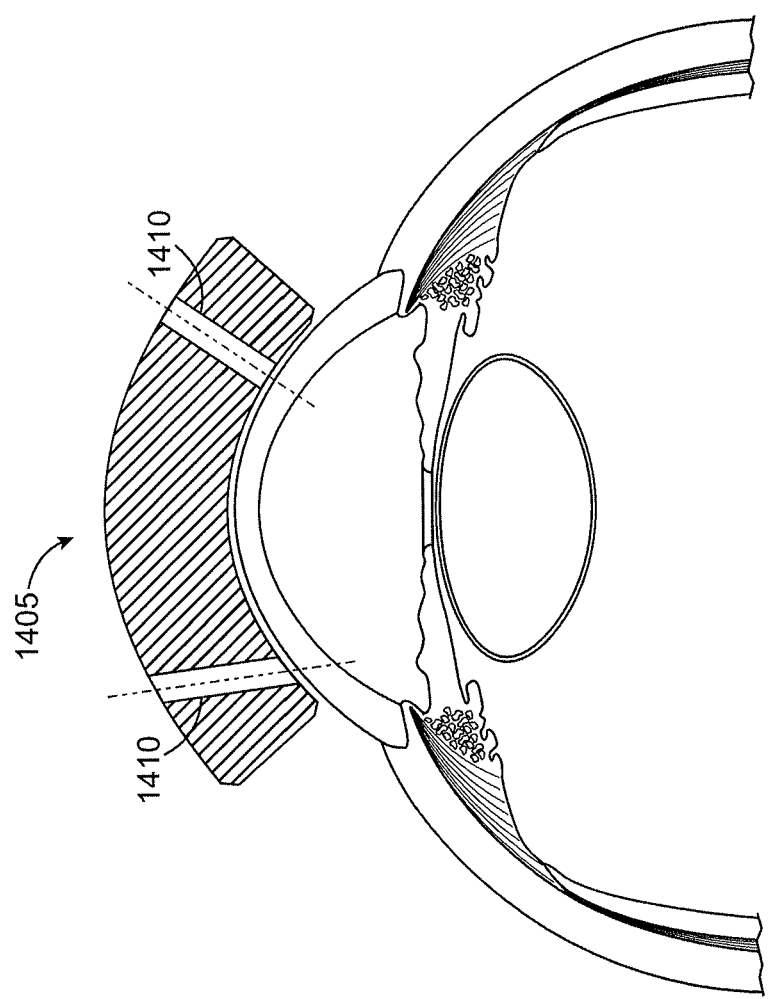
FIG. 14 shows a cross-sectional view of the eye and a viewing lens.

FIG. 14 shows a cross-sectional view of the eye. A viewing lens 1405 (such as a gonioscopy lens represented schematically in FIG. 14) is positioned adjacent the cornea. The viewing lens 1405 enables viewing of internal regions of the eye, such as the scleral spur and scleral junction, from a location in front of the eye. The viewing lens 1405 can optionally include one or more guide channels 1410 that are sized to receive the delivery portion 520 of the delivery device 510. It should be appreciated that the locations and orientations of the guide channels 1410 in FIG. 14 are merely exemplary and that the actual locations and orientations can vary depending on the angle and location where the implant 105 is to be delivered. An operator can use the viewing lens 1405 during delivery of the implant into the eye. The viewing lens 1405 can have a shape or cutout that permits the surgeon to use the viewing lens 1405 in a manner that does not cover or impede access to the corneal incision. Further, the viewing lens can act as a guide through which a delivery device 510 can be placed to predetermine the path of the device as it is inserted through the cornea.

An endoscope can also be used during delivery to aid in visualization. For example, a twenty-one to twenty-five gauge endoscope can be coupled to the implant during delivery such as by mounting the endoscope along the side of the implant or by mounting the endoscope coaxially within the implant. Ultrasonic guidance can be used as well using high resolution bio-microscopy, OCT and the like. Alternatively, a small endoscope can be inserted though another limbal incision in the eye to image the tissue during the procedure.

In an initial step, one or more implants 105 are mounted on the delivery device 510 for delivery into the eye. As mentioned, at least one implant 105 can be mounted over the applier 525 or can be mounted within the applier 525. The eye can be viewed through the viewing lens 1405 or other viewing means such as is described above, in order to ascertain the location where the implant 105 is to be delivered. At least one goal is to deliver the implant 105 in the eye so that it is positioned such that the internal lumen of the implant provides a fluid pathway between the anterior chamber and the suprachoroidal space. If a tube implant having an internal lumen is used, then the internal lumen is positioned such that at least one ingress to the lumen communicates with the anterior chamber and at least one egress communicates with the suprachoroidal space. If a wick implant is used, then the wick member can communicate with both the anterior chamber and the suprachoroidal space. As mentioned, the tube member and wick member can be combined. In such a case, the internal lumen can be open into the anterior chamber and be open at least partially into the suprachoroidal space, while the wick member extends further into the suprachoroidal space.

Figure 15A:
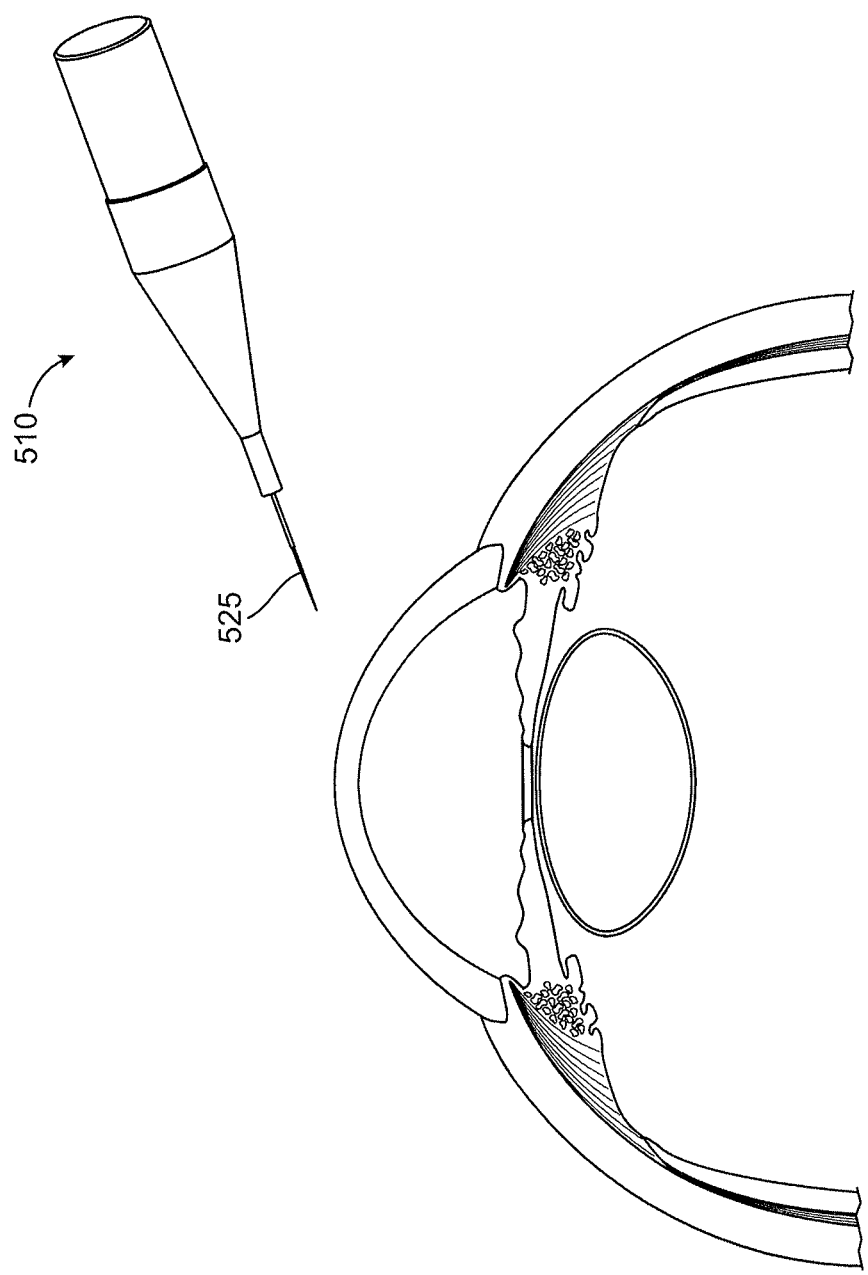
FIG. 15A shows the delivery system positioned for penetration into the eye.

With reference to FIG. 15A, the delivery device 510 is positioned such that the distal tip of the applier 525 or the implant 105 itself can penetrate through the cornea. In this regard, an incision is made through the eye, such as within the limbus of the cornea. In an embodiment, the incision is very close to the limbus, such as either at the level of the limbus or within 2 mm of the limbus in the clear cornea. The applier 525 can be used to make the incision or a separate cutting device can be used. For example, a knife-tipped device or diamond knife can be used to initially enter the cornea. A second device with a spatula tip can then be advanced over the knife tip wherein the plane of the spatula is positioned to coincide with the dissection plane. Thus, the spatula-shaped tip can be inserted into the suprachoroidal space with minimal trauma to the eye tissue.

The incision has a size that is sufficient to permit passage of the implant therethrough. In this regard, the incision can be sized to permit passage of only the implant without any additional devices, or be sized to permit passage of the implant in addition to additional devices, such as the delivery device or an imaging device. In an embodiment, the incision is about 1 mm in size. In another embodiment, the incision is no greater than about 2.85 mm in size. In another embodiment, the incision is no greater than about 2.85 mm and is greater than about 1.5 mm. It has been observed that an incision of up to 2.85 mm is a self-sealing incision. For clarity of illustration, the drawing is not to scale and the viewing lens 1405 is not shown in FIG. 15A, although the applier can be guided through one or more guide channels in the viewing lens. The applier 525 can approach the suprachoroidal space from the same side of the anterior chamber as the deployment location such that the applier does not have to be advanced across the iris. Alternately, the applier can approach the location from across the anterior chamber such that the applier is advanced across the iris and/or the anterior chamber. The applier 525 can approach the eye and the suprachoroidal space along a variety of pathways. Various pathways for approaching the eye and deploying the implant are described in detail below.

After insertion through the incision, the applier 525 is advanced through the cornea and the anterior chamber. The applier is advanced along a pathway that enables the implant to be delivered from the anterior chamber into the suprachoroidal space. In one embodiment, the applier travels along a pathway that is toward the scleral spur such that the applier crosses through the scleral spur or passes below the scleral spur on the way to the suprachoroidal space. The applier 525 can be pre-shaped, steerable, articulating, or shapeable in a manner that facilitates the applier approaching the suprachoroidal space along a proper angle or pathway.

As mentioned, a guidewire can also be used to guide the applier or the implant over the guidewire to the proper location in the eye. The guidewire can be looped at a distal end to assist in making suprachoroidal dissection. Once the implant is properly in place, the loop can be released. If the implant needs to be removed prior to releasing the loop, the guidewire loop can act as a retrieval mechanism. The loop can be larger than the distal lumen opening of the implant such that when the guidewire is pulled back, the loop pulls the implant along with it.

The guidewire can be left in place even after the applier is removed. This enables the user to repeatedly access the site via the guidewire without having to relocate the site in the eye. A cannula can be used to create an access pathway to the delivery site. The delivery tool can then be placed through the cannula. The cannula can remain fixed in place with the viewing lens, and the end of the delivery device can be articulated or steerable such that multiple implants can be placed from one access site. For example an infusion cannula from Dutch Ophthalmic Research Center (D.O.R.C.) can be used, in particular models that allow for continuous infusion and aspiration to maintain a sufficient working area within the anterior chamber.

Figure 15B:
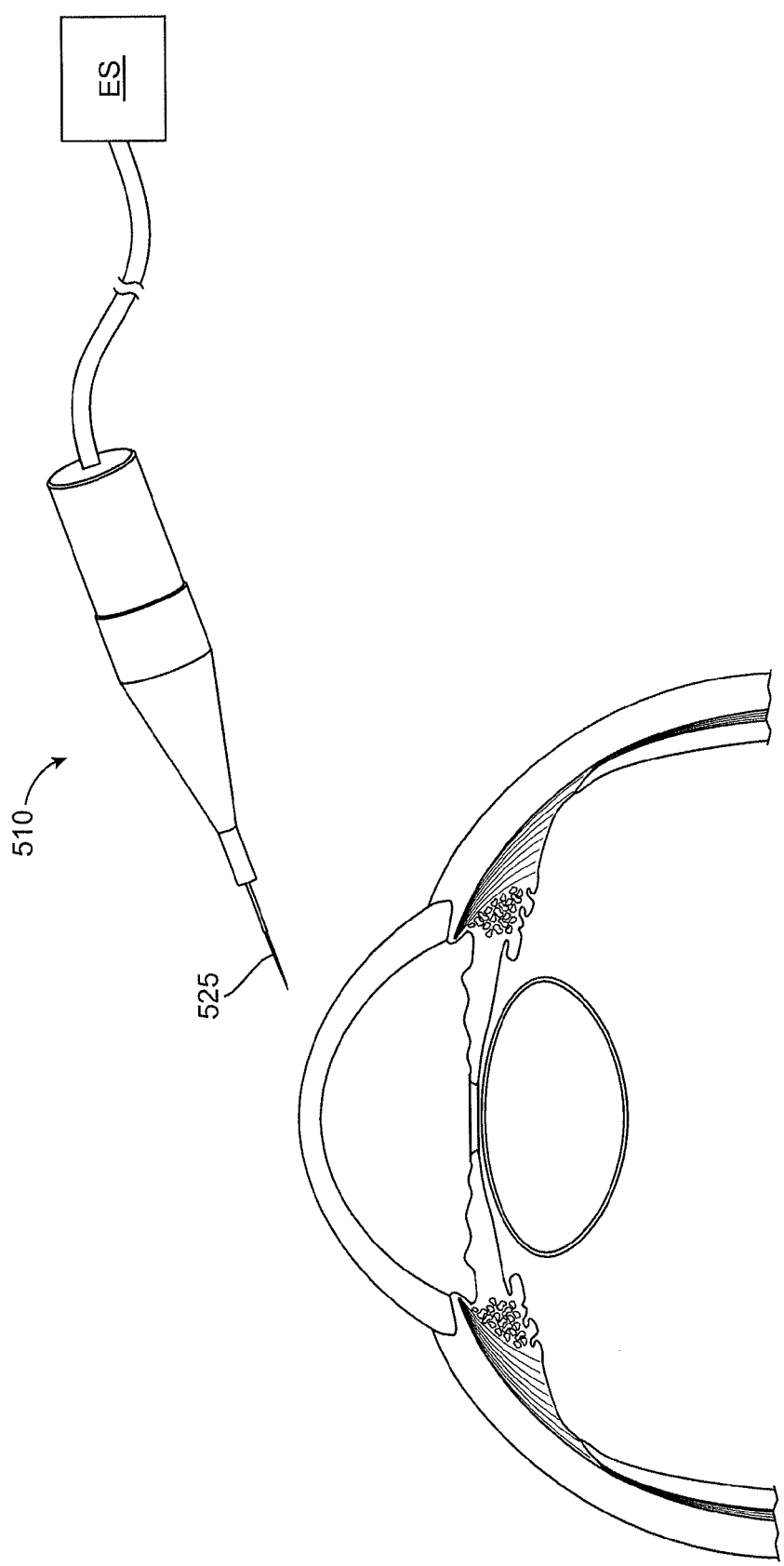
FIG. 15B shows an embodiment wherein the delivery system is connected to an energy source.

As discussed, the distal tip of the applier 525 can be sharp and can also be tapered to facilitate a smooth penetration through the cornea. The distal tip of the implant 105 can also be sharp. In addition, the tip of the applier device can be connected to an energy source ES, to allow energy to be delivered to the tip of the applier body to assist in creating the initial corneal stick, and in addition facilitating entry into the suprachoroidal space through or adjacent the scleral spur. In this embodiment shown schematically in FIG. 15B, only the distalmost tip is exposed to apply energy to the tissue, and the remaining shaft of the applier is insulated such as with a sleeve made of insulation material. Energy delivery wires are attaching to the applier shaft (such as via the handle) to energize the tip portion, and such wires are also connected to an energy delivery source ES and any required grounding pad. The energy that can be delivered to facilitate the procedure can be RF energy, laser energy, resistive heat energy or ultrasonic energy. An energy delivery system for medical use, such as those produced by Stellertech Research (Mountain View, Calif.) can be employed, for example, to apply RF energy to the tip of the applier.

Figure 16:
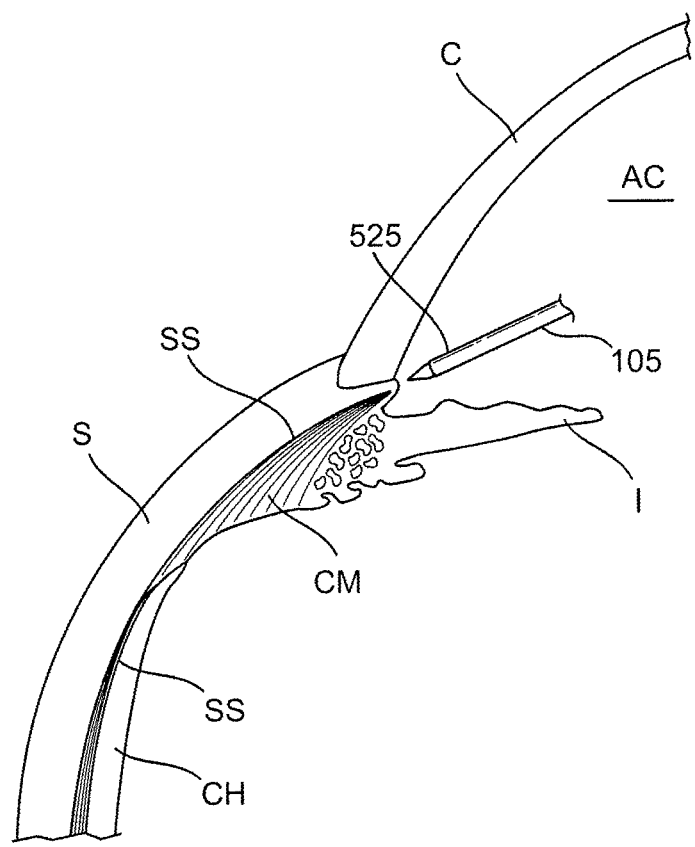
FIG. 16 shows an enlarged view of the anterior region of the eye with a portion of the delivery system positioned in the anterior chamber.

FIG. 16 shows an enlarged view of the anterior region of the eye showing the anterior chamber AC, the cornea C, the iris I, the sclera S, and the choroid CH. The suprachoroidal space is at the junction between the sclera and the choroid. The implant 105 which is mounted on the applier 525, is shown approaching the suprachoroidal space from the anterior chamber. The distal tip of the applier 525 moves along a pathway such that the distal tip is positioned at the scleral spur with the curve of the applier 525 aiming the distal tip toward the suprachoroidal space. In this regard, the applier 525 and/or the implant 105 can have a radius of curvature that conforms to the radius of curvature of the suprachoroidal space. The surgeon can rotate or reposition the handle of the delivery device in order to obtain a proper approach trajectory for the distal tip of the applier, as described in further detail below.

The scleral spur is an anatomic landmark on the wall of the angle of the eye. The scleral spur is above the level of the iris but below the level of the trabecular meshwork. In some eyes, the scleral spur can be masked by the lower band of the pigmented trabecular meshwork and be directly behind it. With the applier 525 positioned for approach, the applier 525 is then advanced further into the eye such that the distal tip of the applier and/or the implant penetrates the scleral spur or abuts the scleral spur and then passes just below the scleral spur. The scleral spur can be used as an anatomical landmark in that he distal tip of the delivery instrument is urged against the scleral spur without penetrating or dissecting the scleral spur. The shape of the scleral spur causes the distal tip of the delivery instrument (or the implant) to slide or otherwise move below the scleral spur toward the suprachoroidal space.

The penetration through the scleral spur (if scleral spur penetration occurs) can be accomplished in various manners. In one embodiment, a sharpened distal tip of the applier or the implant punctures, penetrates, dissects, pierces or otherwise passes through the scleral spur toward the suprachoroidal space. The crossing of the scleral spur or any other tissue can be aided such as by applying energy to the scleral spur or the tissue via the distal tip of the applier 525. The means of applying energy can vary and can include mechanical energy, such as by creating a frictional force to generate heat at the scleral spur. Other types of energy can be used, such as RF laser, electrical, etc.

Figure 17:
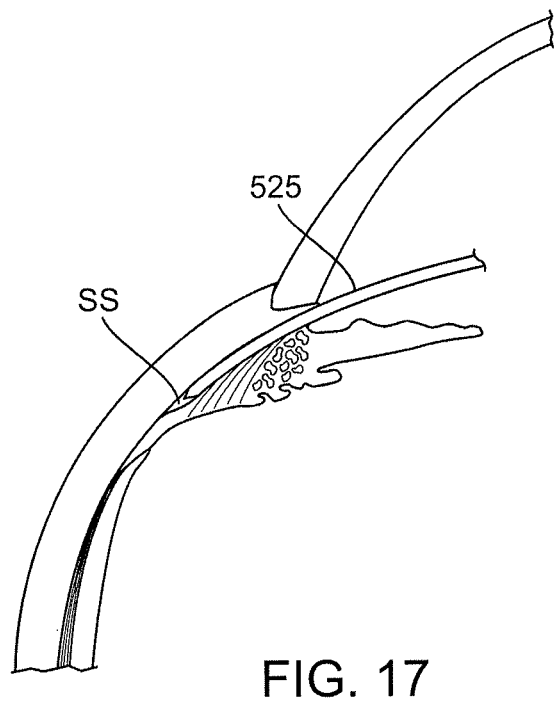
FIG. 17 shows the distal tip of the applier positioned within the suprachoroidal space.

The applier 525 is continuously advanced into the eye, via the trabecular meshwork and the ciliary body, until the distal tip is located at or near the suprachoroidal space such that a first portion of the implant 105 is positioned within the suprachoroidal space and a second portion is positioned within the anterior chamber. In one embodiment, at least 1 mm to 2 mm of the implant (along the length) remains in the anterior chamber. FIG. 17 shows the distal tip of the applier 525 positioned within the suprachoroidal space SS. For clarity of illustration, FIG. 17 does not show the implant mounted on the applier, although the implant 525 is mounted on the applier during delivery. As the applier 525 advances through tissue, the distal tip causes the sclera to peel away or otherwise separate from the choroid to expose the suprachoroidal space.

One method of approach is to advance the applier 525 through the ciliary body as it approaches the suprachoroidal space. The tissue of the sclera is structurally more tough than the ciliary body. As the distal tip of the applier 525 passes through the ciliary body and reaches the scleral tissue, the scleral tissue provides an increased resistance to passage of the applier 525 therethrough. Thus, the surgeon will detect an increase in resistance to passage when the distal tip of the applier passes through the ciliary body and reaches the sclera. This can serve as an indication that the distal tip of the applier has reached the suprachoroidal space. In this regard, the distal region of the applier 525 or the implant can have a shape, such as a spade shape or a blunt end, that is configured to facilitate creating a dissection plan between the choroid and the sclera and positioning of the distal region of the applier in the suprachoroidal space. This thickness of this dissection plane is approximately the same as the size of the device being placed. The distal region can be flexible or looped to allow for preferential movement into the space between the sclera and choroid.

As mentioned, the delivery device 510 and/or the implant 105 can be equipped with navigational aides, such as radiopaque markers, or means to enable ultrasonic visualization that assist in proper positioning of the applier and implant in the eye. Once the applier 525 has been properly positioned, the implant 105 is advanced off of the applier 525, such as by actuating the implant advancing actuator 535 to move the advancing structure 530 (FIG. 5) so as to push the implant 105 off of the applier into proper placement in the eye.

The implant 105 can be deployed off of the applier in various manners. For example, as discussed above, the implant can be pushed off the applier by moving the advancing structure 530 (shown in FIGS. 5-6G) in the distal direction. In an alternate method, the advancing structure 530 remains stationary and the applier 525 is withdrawn in the proximal direction as was described above with reference to FIGS. 6E-6G. This can method can be advantageous as the implant remains stationary during dismount from the applier 525 rather than being moved during dismount. Thus, the implant can be properly positioned while still on the applier 525. In another method, the applier is distally advanced into the suprachoroidal space while the implant remains stationary against the advancing structure 530. The advancing structure is then moved distally to push the implant along the applier. The applier is then withdrawn into the advancing structure to uncouple the implant from the applier.

Figure 18:
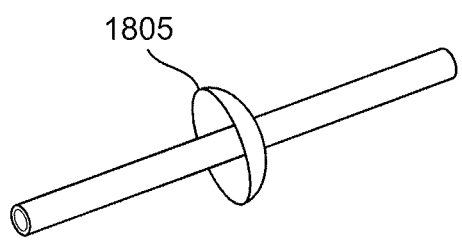
FIG. 18 shows an implant having a skirt.
Figure 19:
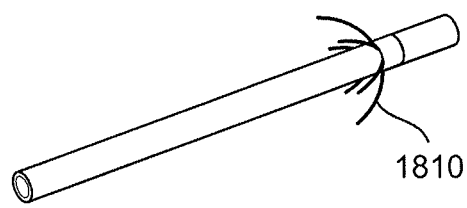
FIG. 19 shows an implant that is equipped with a pronged skirt.
Figure 20:
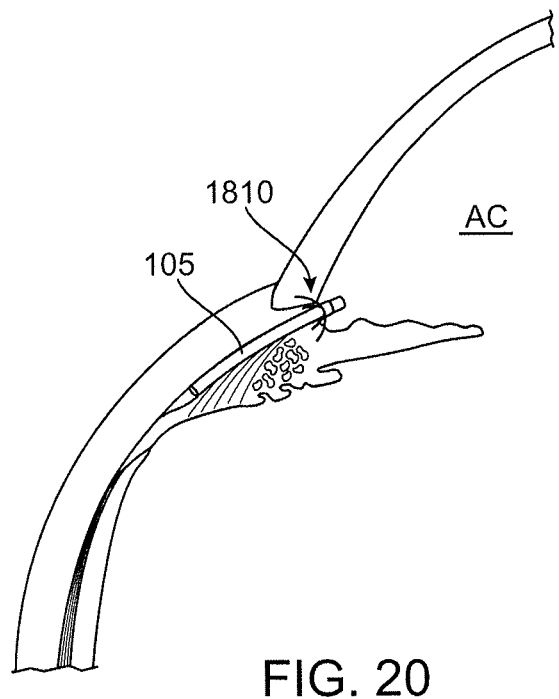
FIG. 20 shows the skirted implant positioned in the eye.

The implant can include structural features that assist in proper placement of the implant, such as to ensure that the implant 105 is not advanced any further than necessary into the eye. For example, the implant 105 can include a structure, such as the proximal retaining member 1005 (shown in FIG. 10), that abuts the scleral spur or another tissue structure to prevent further movement of the implant into the eye. FIG. 18 shows an implant 105 that is equipped with a skirt 1805 and FIG. 19 shows an implant that is equipped with a pronged skirt 1810. As shown in FIG. 20, the skirt 1810 or 1805 abuts and anchors into the ciliary body to prevent the implant 105 from being advanced any further into the eye. These features can further serve to prevent leakage of fluid around the outside of the implant. Previous efforts to increase the drainage of the anterior chamber by surgically creating a path between the anterior chamber and the suprachoroidal space, known as cyclodialysis procedures, often caused too much drainage and low pressure ("hypotonia") in the anterior chamber. Concern for excess flow and resultant hypotony can be a major reason why previous efforts have focused on placing implants through a scleral incision, so the sclera would surround at least a portion of the implant to prevent flow around the implant. Therefore, these means for preventing flow around the outside of the implant can prove essential in enabling placement of an implant directly from the anterior chamber to the suprachoroidal space without risk of hypotonia.

Figure 21:
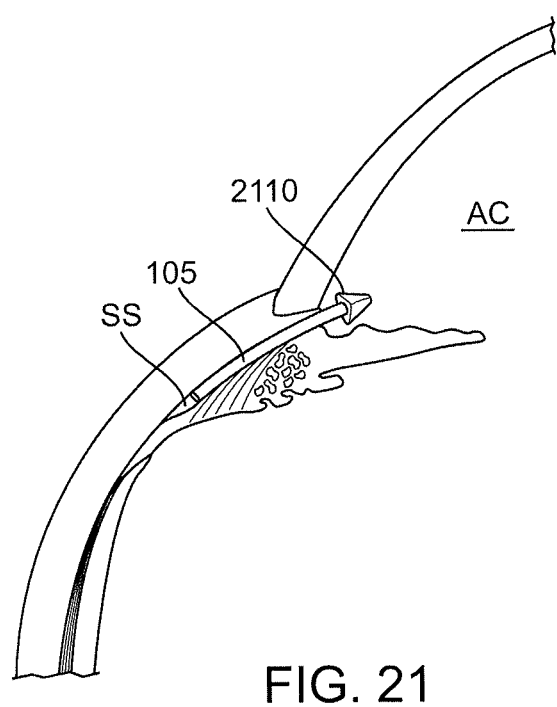
FIG. 21 shows an implant implanted in the eye so as to provide a fluid pathway between the anterior chamber and the suprachoroidal space.

FIG. 21 shows the implant 105 implanted in the eye so as to provide a fluid pathway between the anterior chamber AC and the suprachoroidal space SS. The implant 105 was implanted by "tunneling" the implant toward the suprachoroidal space. That is, as the implant is advanced toward the suprachoroidal space, the distal tip of the applier and/or the implant penetrates the tissue and forms a tunnel through the eye tissue, initially the ciliary body. This differs from a procedure where the implant is lowered into the eye via a scleral flap that is cut and folded back for access to the implant location. In such a procedure, the implanted implant is positioned within a cavity that was formed by the folded-back flap. However, in the procedure shown in FIG. 21, the implant 105 is substantially enclosed or surrounded by eye tissue in the region between the anterior chamber and the suprachoroidal space. It also differs from the procedure known as cyclodialysis, that in some cases entirely disinserts the ciliary body from the scleral spur to relieve the pressure in the anterior chamber, because essentially a puncture is made and the implant device that is placed, is left in the position of the puncture.

Although FIG. 21 shows only a single implant 105, it should be appreciated that multiple implants can be implanted in the eye. The implants can be implanted end-to-end to form a single, elongate fluid pathway or a plurality of implants can be positioned side-by side or spaced around the circumference of the anterior chamber to form multiple fluid pathways. In addition, a single implant can be implanted in an initial procedure and additional implants implanted in one or more subsequent procedures as needed to establish or maintain optimal anterior chamber pressure.

If multiple implants are used, it is not necessary that all of the implants (or all openings in an implant) be initially patent. This will allow the drainage of aqueous humour to be initiated in a controlled manner by selectively opening additional implants over a period of time. Over time, additional implants can be activated (i.e., opened), such as by the insertion of a stylet or other needle-type device, such as during an office visit. The implants can also be opened or re-opened (if an implant becomes blocked after implantation) in various manners, such as using a photochemical, laser, RF, ultrasound, or thermal procedure, or combinations thereof. For instance, the implant can have a single hole or multiple holes along its proximal end or distal end, one or more of which are initially covered by a second tube or other material. Applying light or other energy to the tube could cause the holes to open or could cause the tube to shrink longitudinally, exposing additional openings to increase flow.

In addition, the outer diameter of the implant or the diameter of the internal lumen can be varied by shrinking or enlarging the implant using thermal, light, or photochemical activation. For example, the implant can be initially relatively long and thin. Applying energy or other activation to the implant could cause it to become shorter and/or larger in diameter, increasing its flow rate.

It is possible that the dissection formed by the implant can cause a leak between the anterior chamber and the suprachoroidal space. In such a case, the leak can be filled or otherwise plugged with a material (such as a foam or adhesive) or a structure (such as a gasket) that prevents leaking.

With reference still to FIG. 21, a spacer structure 2110 can optionally be located on the proximal end of the implant 105. The spacer structure 2110 is a structure that extends outwardly from the implant 105 to prevent blockage of the proximal end of the implant 105. With further reference to FIG. 21, the structure 2110 can also facilitates grasping the implant in the event it is necessary to remove the implant.

In another embodiment, the implant 105 is not positioned on the applier 525 as the applier is advanced into the eye. In such a case, the handle component 515 of the delivery instrument can be detached from the proximal end of the applier after the applier has been properly positioned in the eye. The implant 105 is then threaded over the applier, from the proximal end to the distal end, toward the delivery site.

In one implementation, a guide passageway is formed in the eye prior to advancing the applier through the eye. The applier is then advanced through the previously formed passageway rather than using the applier to tunnel through the eye. The passageway can be formed in various manners, such as by using an energy source or phacoemulsification equipment to form the passageway.

Additional Implant and Delivery System Embodiments

Figure 22:
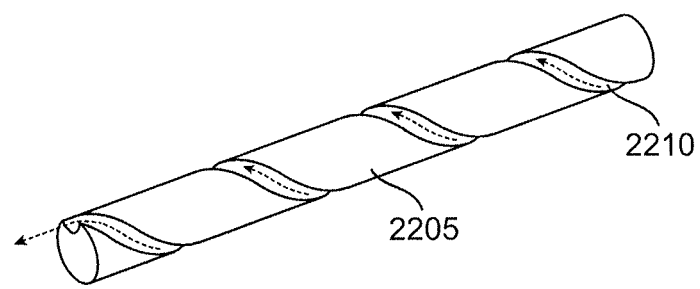
FIGS. 22 and 23 shows implant s that include external fluid flow features.
Figure 23:
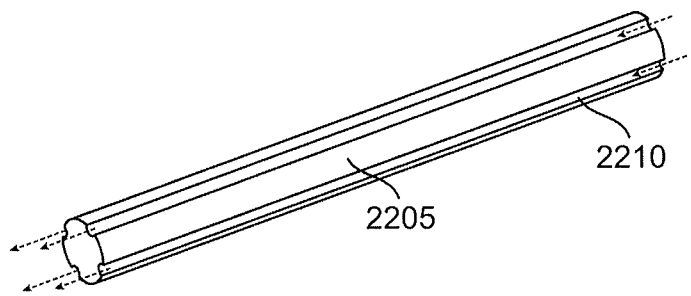

Additional embodiments of the implant 105 are now described. FIG. 22 shows an implant 105 that includes an elongate core member 2205 that has one or more external fluid flow features, such as flow channels 2210, located on its outer surface. The flow channel(s) 2210 define at least one passageway for the flow of aqueous humour along the length of the implant 105. The configuration of the flow channel(s) 2210 can vary. In the embodiment of FIG. 22, a single flow channel 2210 having a helical or spiral configuration is located on the outer surface of the core member 2205. The core 2205 can also include multiple spiral flow channels. FIG. 23 shows another embodiment, wherein a plurality of straight or substantially straight flow channels are located on the external surface of the core member 2205. The implant 105 can also include just a single straight flow channel or can include a combination of straight flow channels and flow channels of various curvilinear configurations.

The core 2205 can be a solid piece of material that does not have an internal lumen. A solid core 2205 can form a strong structure and can create a reliable flow path with a reduced risk of structural collapse or tissue ingrowth in the lumen. Alternately, the external flow channels can be combined with an internal lumen that extends through the core 2205. If the core 2205 is solid without an internal lumen, then it can be delivered into the eye through a delivery lumen of a delivery device, such as through an applier. If the core 2205 includes an internal lumen, then the core can be delivered into the eye mounted over a delivery device, such as over an elongate applier.

The core 2205 can be manufactured in various ways. For example, the core 2205 can be molded or can be extruded, such as from a biocompatible material or any of the materials described herein. The core 2205 can also be formed of a combination of different materials or can be co-extruded.

Figure 24:
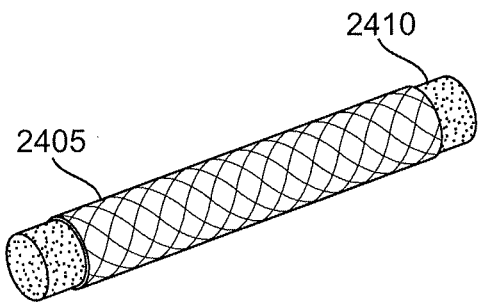
FIGS. 24, 25A, and 25B shows an implant that includes an elongate outer member mounted over a plug member.

FIG. 24 shows an implant 105 that includes an elongate outer member 2405, such as a stent, mounted over a plug member 2410. When this embodiment of the implant 105 is implanted between the anterior chamber and the suprachoroidal space, the plug member 2410 degrades over time, while the outer member 2405 does not degrade. The outer member 2405 remains in the eye to maintain a patent passageway between the anterior chamber and the suprachoroidal space. The outer member 2405 can be solid (such as an elongate tube) or it can be a mesh. The outer member 2405 can be integrally formed with the plug member 2410 or it can be embedded in varying degrees within the plug member to control the rate of degradation.

The degradation of the plug 2410 can be configured in various manners. For example, the rate of degradation of the plug can be based on the intraocular pressure such that the degradation rate increases as the intraocular pressure increases. Thus, a higher intraocular pressure results in a greater rate of plug degradation than a lower intraocular pressure. In this manner, the rate of degradation of the plug can slow as the intraocular pressure approaches a predetermined value.

Figure 25A:
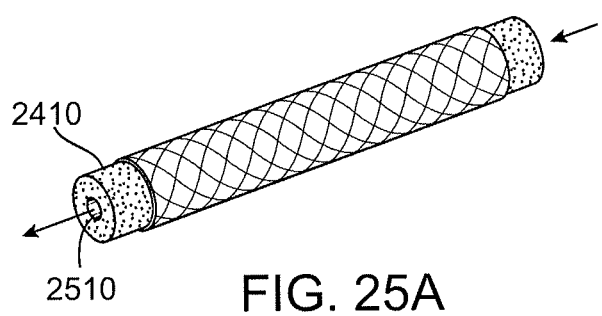
Figure 25B:
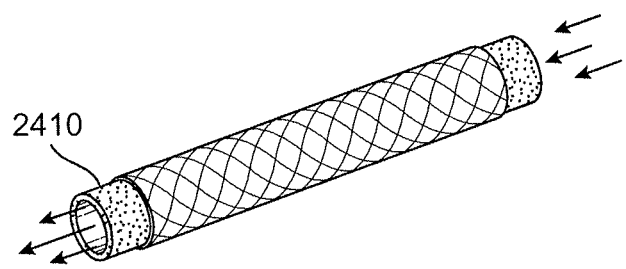

An exemplary way of implementing such a feature is to include an internal lumen 2510 in the plug 2410, as shown in FIG. 25A. In an initial state, the lumen 2510 has diameter of a reduced size such that a low level of aqueous humour flows through the lumen. The initial state can correspond to the plug being exposed to an initially-high intraocular pressure. The high intraocular pressure causes the plug 2410 to degrade such that the size of the lumen increases. As the size of the lumen increases (as shown in FIG. 25B), the level of aqueous humour flow through the lumen also increases, which results in a reduction in intraocular pressure and a reduction in the rate of degradation of the plug.

In an alternate embodiment of the device shown in FIG. 24, the stent 2405 does not include an internal member. Thus, a stent 2405 is implanted into the eye in a manner that maintains an opening between the suprachoroidal space and the anterior chamber. The stent 2405 can be a self-expanding or balloon expanding stent that is expanded after it is positioned within the eye. The stent 2405 can be for example a braided or laser cut stent made of stainless steel or Nitinol.

The implant can also be manufactured of a material that is absorbed into the eye tissue after placement in the eye. Once absorbed, a space remains where the implant was previously located. In this regard, the implant can be manufactured of a complex carbohydrate or a collagen that is non-inflammatory. In another embodiment, the implant is covered with or filled with a material that absorbed into the eye over time such as to prevent hypotony or to prevent a clot forming within the tube.

In the case of biodegradable or bioabsorbable devices, a variety of materials can be used, such as biodegradable polymers including: hydroxyaliphatic carboxylic acids, either homo- or copolymers, such as polylactic acid, polyglycolic acid, polylactic glycolic acid; polysaccharides such as cellulose or cellulose derivatives such as ethyl cellulose, cross-linked or uncross-linked sodium carboxymethyl cellulose, sodium carboxymethylcellulose starch, cellulose ethers, cellulose esters such as cellulose acetate, cellulose acetate phthallate, hydroxypropylmethyl cellulose phthallate and calcium alginate, polypropylene, polybutyrates, polycarbonate, acrylate polymers such as polymethacrylates, polyanhydrides, polyvalerates, polycaprolactones such as poly-ε-caprolactone, polydimethylsiloxane, polyamides, polyvinylpyrollidone, polyvinylalcohol phthallate, waxes such as paraffin wax and white beeswax, natural oils, shellac, zein, or a mixture thereof, as listed in U.S. Pat. No. 6,331,313 to Wong, which is expressly incorporated by reference in its entirety.

Figure 26:
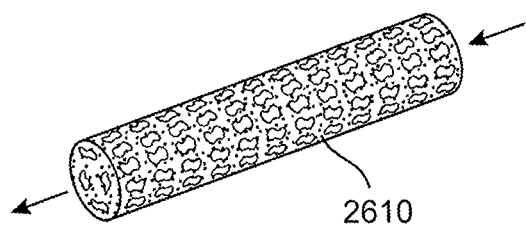
FIG. 26 shows an embodiment of the implant formed of a sponge-like flow member.
Figure 27:
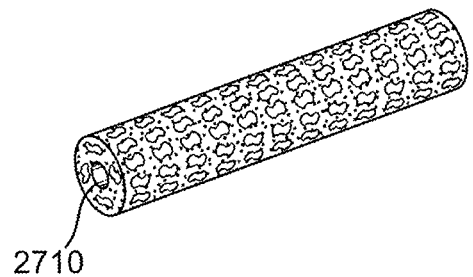
FIG. 27 shows an implant as in FIG. 26 having an internal lumen.

FIG. 26 shows another embodiment of the implant that is formed of a sponge-like flow member 2610 that is made of a porous material, such as polyester material. The porous nature of the flow member 2610 forms one or more fluid pathways for the flow of aqueous humour through the flow member. The flow member 2610 can be formed of a material that can be pierced along its length by a wire or other structure. The piercing forms an internal lumen 2710 (FIG. 27) through which aqueous humour can flow. The internal lumen 2710 can be formed in the situation where it is desired to increase the flow of aqueous humour through the flow member.

Figure 28:
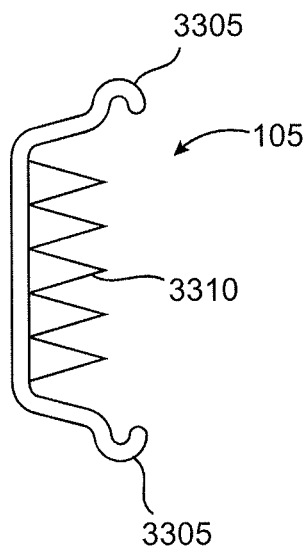
FIG. 28 shows an embodiment of the implant that includes a pair of anchor members located on opposite ends of the implant.

FIG. 28 shows another embodiment of the implant 105 that includes a pair of anchor members 3305 located on opposite ends of the implant. The anchor members 3305 are sized and shaped to engage the eye tissue to retain the implant 105 in a fixed or substantially fixed position within the eye. The implant 3305 includes an elongated central region on which are disposed one or more tines or teeth 3310 that are adapted to anchor with the eye. The anchor members 3305 and the teeth 3310 extend outwardly from the implant 105 to define a space 3315 disposed along at least one side of the implant 105 when the implant 105 is positioned in the eye. The teeth can be oriented to extend at least partially into the trabecular meshwork such that the teeth form flow pathways into Schlemm's canal. The teeth 3310 can be manufactured of various materials including silver or coated with silver. Silver is a material that prohibits growth of surrounding tissue such that a space is retained around the implant.

Figure 29:
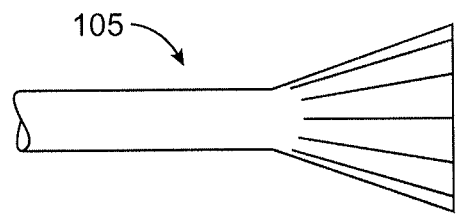
FIG. 29 shows an end region of the implant that includes slices.

As discussed above with reference to FIG. 7, a distal or proximal end of the implant 105 can be equipped with retaining structures. FIG. 29 shows an end region (distal and/or proximal) of the implant 105 that includes slices that extend generally along the longitudinal direction of the implant. The orientation of the slices can vary. For example, the slices can extend longitudinally such that the slices define a plurality of longitudinally-extending teeth that can interact with eye tissue to resist migration of the implant 105. The slices can also be oriented transverse to the longitudinal axis of the implant. The end region can be flared outward to provide further resistance to migration.

Figure 30:
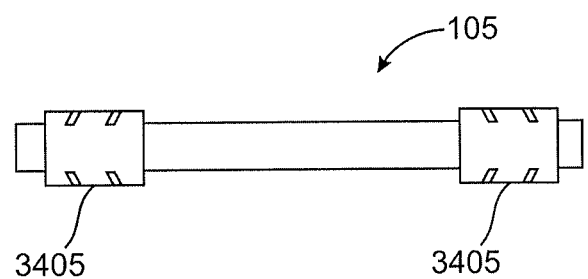
FIG. 30 shows an embodiment of the implant with outer sleeves.

In another embodiment, shown in FIG. 30, one or more sleeves 3405 are positioned over the outer surface of the implant 105. The sleeves 3405 can be interspersed at various locations along the length of the implant 105. In the embodiment of FIG. 30, a first sleeve 3405 is located on a distal region of the implant 105 and a second sleeve 3405 is located on a proximal region of the implant 105. More than two sleeves can be positioned on the implant. The sleeves 3405 have an inner diameter that permits the sleeves to be fixedly mounted over the implant. The outer diameter of the sleeve is larger than the outer diameter of the implant such that the sleeves form a raised surface on the implant. The sleeves 3405 can be annular such that the sleeves have an internal lumen that fits entirely around the circumference of the implant. Alternately, the sleeves 3405 are non-annular strips of material that are positioned on the implant such that they cover only a portion of the circumference of the implant.

As an alternative or in addition to sleeves that are positioned over the implant, the outer surface of the implant can include grooves that are machined or molded into the outer surface. The grooves can be a series of annular grooves or a single corkscrew groove that extends along the length of the implant. The grooves function to form alternating raised and lowered surfaces on the implant. The implant could also include pits or pockmarks on the outer surface.

The sleeves 3405 can have a smooth outer surface, an undulating outer surface, or can include one or more slices that can be oriented at various angles relative to the longitudinal axis of the implant 105. The slices form teeth in the sleeves 3405 to resist migration of the implant. The sliced teeth can be biased outward such that the teeth flare outward and engage adjacent tissue to prevent movement in either the proximal or distal direction.

Any of the sleeves can also act as a marker to show the physician the proper implant length to be inserted into the eye. Alternately, one or more printed markers can be formed on the implant outer wall or on the delivery device. The markers can be $BaSO_4$ markers embedded in the implant material wall wherein the markers are made from an extruded polymer compounded with this radiopaque substance in the region of the desired radiopacity. Further, the markers can be laser printed or etched on the implant device to show the amount of implant deployed in the suprachoroidal space, or the amount by which the implant device should be allowed to protrude into the anterior chamber. The sleeves can be manufactured of various materials. In one embodiment, at least one of the sleeves is made of an anti-microbial silver material.

Figure 31:
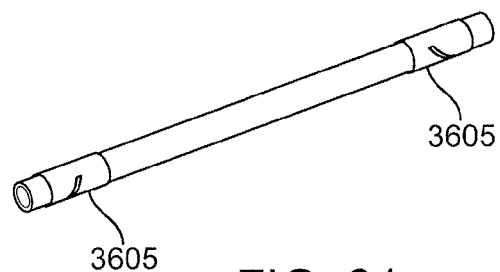
FIG. 31 shows another embodiment of the implant with sleeves.

FIG. 31 shows another embodiment of the implant 105 with sleeves 3605 disposed on proximal and distal ends of the implant. The sleeves 3605 have slices that form arcs. The slices can be straight or they can be curvilinear. When the slices are located on the sleeves 3605 rather than on the body of the implant itself, the slices will not interfere with fluid flow through the lumen of the implant. There is a risk that if the slices are on the implant itself, an ingrowth of tissue into the slices can result. Such an ingrowth can interfere with the flow of fluid through the implant's internal lumen. Advantageously, the sleeves permit the use of slices that do not interfere with the internal lumen of the implant. The slices on the sleeves create retention means on both ends of the implant. The slices are biased toward each other so that micromotion of the implant is prevented. As a force acts upon the implant to force the implant either further into the suprachoroidal space or into the anterior chamber, the slices begin to extend axially from the longitudinal axis of the inner lumen causing a restriction of movement of the implant in either direction.

Figure 32:
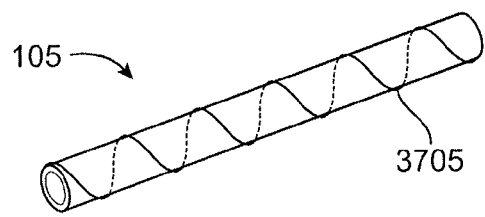
FIG. 32 shows another embodiment of the implant, which has a coiled structure.

FIG. 32 shows yet another embodiment of the implant 105. In this embodiment, a retention structure, such as a coil 3705, is located on the outside of the implant 105. The coil 3705 can be formed of a wire that is wrapped around the outer surface of the implant. The coil 3705 functions to retain the implant 105 within the eye. In some embodiments, the coil 3705 can also be sized and shaped such that it forms a conduit or flow path that directs fluid to flow along the outside of the implant. The retention structure need not be coil shaped but can rather have various shapes and sizes adapted to retain the implant in place. For example, the retention structure can be a straight wire that extends along the length of the implant and that is raised relative to the outer surface of the implant. The wire can have various dimensions. In one embodiment, the wire has a diameter of 0.0005 inch.

It can be desirable to position one or more structures on the implant that can be grasped, such as to reposition the implant or remove the implant from the eye. Some embodiments of the implant that include removal or repositioning structures are now described. The removal or repositioning structure can be any structure on the implant that can be grasped in order to move or remove the implant. For example, the removal structure can be an enlarged region, a raised region, or a region of reduced diameter that provides a location that can be grasped by a removal tool. The retention elements described above can also serve as a grasping element for removal or moving of the implant.

Figure 33A:
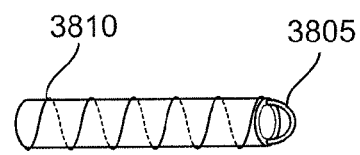
FIGS. 33A and 33B and 34 show embodiments of the implant that include a grasping loop.
Figure 33B:
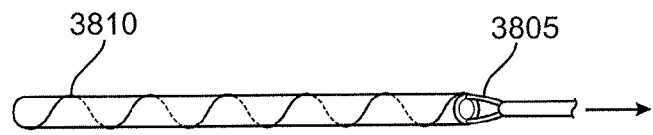
Figure 34:

FIG. 33A shows an embodiment of the implant 105 that includes a grasping loop 3805 on the proximal end of the implant. The grasping loop 3805 is shaped such that it can be grasped by a removal tool or a repositioning tool. The grasping loop 3805 can be connected to a coil member 3810 that extends entirely or partially along the length of the implant 105 such that when the grasping loop is pulled, the implant undergoes a radial reduction in size, as shown in FIG. 33B. The implant can also include outer thread structures that permit the implant to be screwed into the suprachoroidal space by rotating the implant in one direction and then screwed out by rotating in an opposite direction. The threads can grasp onto the surrounding tissue to provide counter traction when the grasping loop 3805 is pulled. The implant 105 can also be formed of a braided shaft with a distal grasping loop 3805, as shown in FIG. 34.

Figure 35:
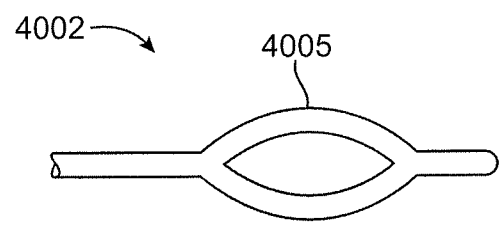
FIG. 35 shows an embodiment of an elongate device with a snare that can be positioned inside an implant.

FIG. 35 shows another embodiment of an elongate device 4002 with a snare 4005 located on a proximal end. The device 4002 can be positioned within a lumen of the implant such that the snare 4005 is compressed within the lumen. In use, the device 4002 is pulled partially out of the lumen such that the snare 4005 expands to form a loop that can be grasped by a removal or repositioning tool.

Figure 36:
FIG. 36 shows an embodiment of a spatula-shaped end region of an implant.

In another embodiment, shown in FIG. 36, the implant 105 includes a distal region 4105 that is flat and thin so as to have a spatula-like shape. The flat and thin configuration of the implant is adapted to facilitate penetration of the eye and to facilitate peeling of the choroid from the sclera and positioning of the distal region of the applier in the suprachoroidal space. The implant includes an internal lumen for the passage of a guidewire or through which fluid or visco-elastic substance(s) can be passed to assist dissection or visualization. In addition, a fiber optic can also be passed through the lumen to assist direct visualization of the treatment region as desired during placement or repositioning of the implants.

Figure 37:
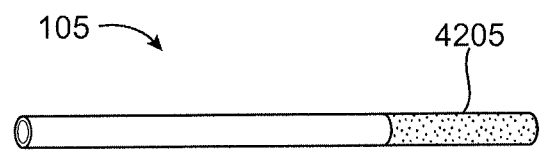
FIG. 37 shows an implant having an atraumatic tip.

As discussed, the implant 105 can be shaped or otherwise configured so as to minimize the risk of trauma to the eye during delivery or during micromotion of the implant after the implant has been delivered. For example, any region of the implant can have an atraumatic shape or can be manufactured of or coated with a soft material. In one embodiment, shown in FIG. 37, an atraumatic tip 4205 is located on the proximal region of the implant 105. The tip 4205 can be shaped in an atraumatic manner, such as by having a rounded end. The tip 4205 can be manufactured of a material that is softer than the remainder of the implant or can be manufactured of the same material. The atraumatic tip 4205 is adapted to protect against damage to the cornea in the event of corneal contact or micromotion of the implant. In one embodiment, at least a portion of the implant includes a silicone sleeve that at least partially covers the outer surface of the implant. The silicone sleeve can be formed by dipping the implant into a silicone solution.

Figure 38:
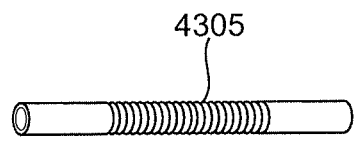
FIG. 38 shows an embodiment wherein the implant that includes a resilient region.

FIG. 38 shows another embodiment wherein the implant 105 includes a resilient region 4305. The resilient region can be formed in various manners. For example, in one embodiment, the resilient region is formed by either a reinforced region of silicone tube or by a separate resilient element such as a spring. In another embodiment, the resilient region 4305 is corrugated to provide flexibility. The spring can be formed of various materials, including polyimide and stainless steel. Any of the embodiments of the implant described herein can include a resilient region along a portion of its length or can be resilient along its entire length. In addition, the implant can be flexible along its entire length, can have a predetermined stiffness along its entire length or can have a stiffness that varies along its length.

Figure 39:
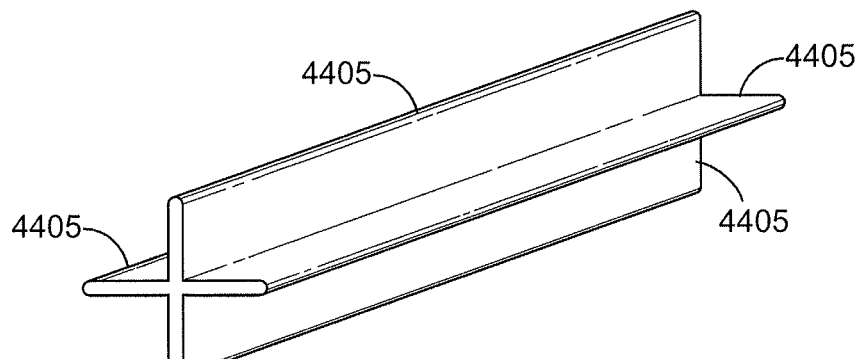
FIGS. 39, 40A, and 40B show alternate embodiments of the implant.

As discussed above with reference to FIGS. 22 and 23, the implant can be formed without an internal lumen and configured such that the flow occurs along the outer surface of the implant. FIG. 39 shows another embodiment of an implant 105 that does not have an internal lumen. The implant 105 has a plurality of extensions 4405 that extend radially outward from a central core. The extensions 4405 define elongated grooves that extend along the length of the implant. The elongated grooves serve as flow pathways to guide fluid flow along the length of the implant. The embodiment of FIG. 39 has four extensions although the quantity of extensions can vary. A material, such as silver, can be positioned or coated within the grooves to keep the channels open and to provide increased distribution area for fluid flow. As mentioned, silver serves to inhibit or prevent tissue growth.

Figure 40A:
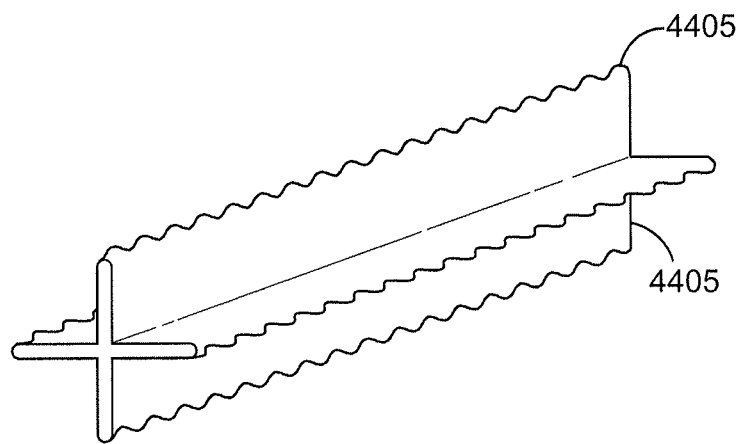
Figure 40B:
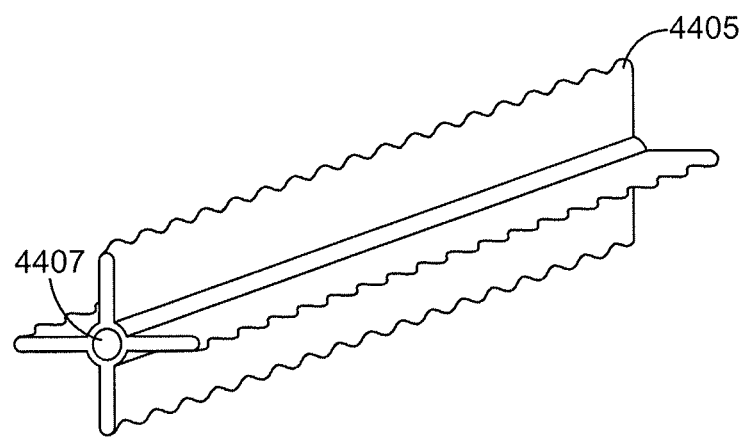

As shown in FIG. 40A, the peripheral edges of the extensions 4405 can have grooves or other structures that are adapted to retain or anchor the implant within the eye. In the embodiment shown in FIG. 40B, the implant 105 has extensions 4405 and a central core with an internal lumen 4407 that can be used to mount the implant on a delivery device. The central lumen 4407 can also be used for the flow of fluid through the implant.

Figure 41:
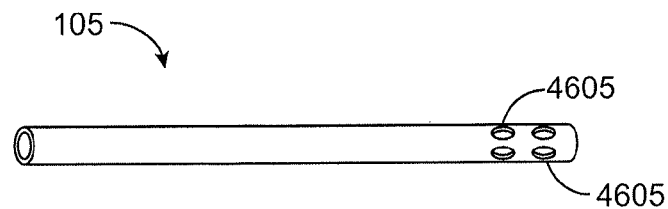
FIG. 41 shows an embodiment of the implant with holes that communicate with an internal lumen.

The implant can include features that are adapted to modify or enhance the flow of fluid through or along the implant, such as after the implant has been placed in the eye. In one embodiment, shown in FIG. 41, the implant 105 has one or more holes that 4605 that communicate with the internal lumen. The holes are initially plugged with a material such that flow cannot occur through the holes. After placement of the implant in the eye, the holes can be unplugged, such as by inserting an instrument through the holes or applying energy to the location where the holes are to be formed. The holes can also unplug automatically by plugging the holes with a material that degrades upon placement in the eye or that degrades after a period of time.

Figure 42A:
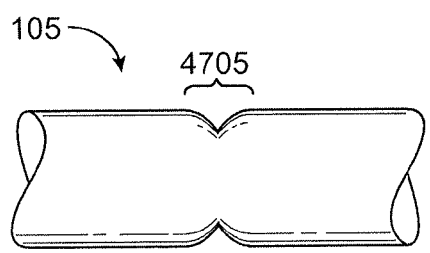
FIGS. 42A, 42B, and 43 show embodiments of the implant that include valved regions.
Figure 42B:
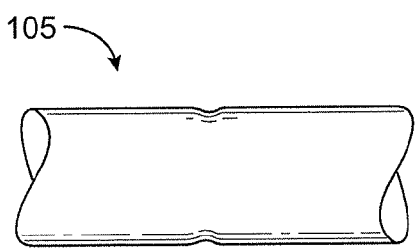

FIG. 42A shows a cross-sectional view of a portion of another embodiment of the implant 105. In this embodiment, the implant 105 includes a narrowed region 4705 such that the internal lumen 4710 is at least partially blocked in the narrowed region 4705. As shown in FIG. 42B, the narrowed region 4705 can be opened or expanded at a desired time, such as through applying heat to the narrowed region 4705 to cause the narrowed region to expand such that the internal lumen is no longer blocked. The region can then be narrowed again by further application of heat if desired. The narrowed region can also be opened and closed by tying a biodegradable band or suture around the narrowed region. The sutures can erode over a time period so that the narrowed region gradually opens over time.

Figure 43:
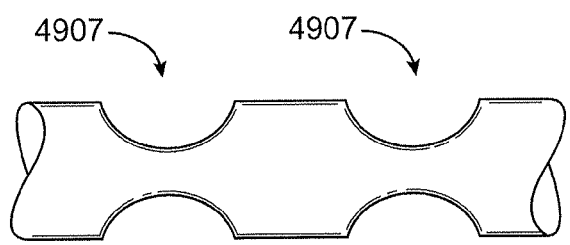

FIG. 43 shows another embodiment of the implant 105 that includes one or more valved regions 4907 along the length of the implant. The valved regions 4907 serve to regulate the flow of fluid through the internal lumen. Each of the valve regions 4907 can include a separate valve structure or can be shaped to regulate fluid flow. For example, the valved regions can have an expanded size that permits more fluid flow or can have a reduced size that limits fluid flow. The valved regions can be colored so as to respond to different colors of laser light depending on a desired result.

Figure 44:
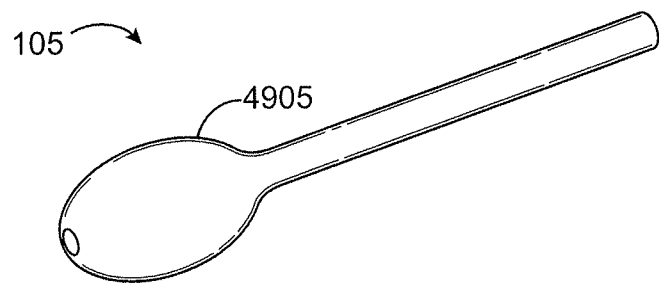
FIGS. 44 and 45 show embodiments of the implant that include one or more bulbous elements.

FIG. 44 shows an embodiment of the implant 105 that includes a bulbous element 4905 that is radially larger than the remainder of the implant. The bulbous element 4905 can be fixed in the enlarged state or it can be adapted to transition from a reduced-size state to the enlarged-size state. For example, the bulbous element 4905 can be an expandable balloon or it can be an expansion members 910 such as was described above in FIG. 9A. The bulbous element 4905 can include holes that communicate with the internal lumen of the implant 105 to permit ingress and egress of fluid.

Figure 45:
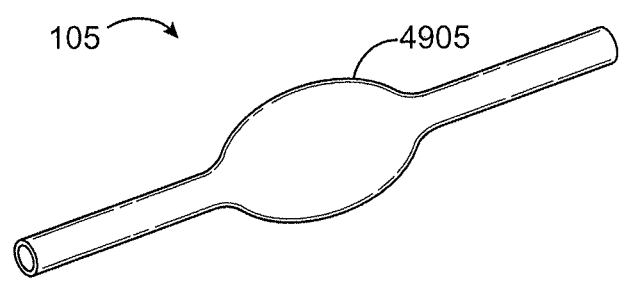

FIG. 45 shows another embodiment of the implant 105 wherein the bulbous element 4905 is located between the proximal and distal ends of the implant 105. Thus, the implant 105 includes a central bulbous element 4905 with proximal and distal regions of reduced radial size relative to the bulbous element. The implant 105 can also include a plurality of bulbous elements that are interspersed along the length of the implant.

Figure 46:
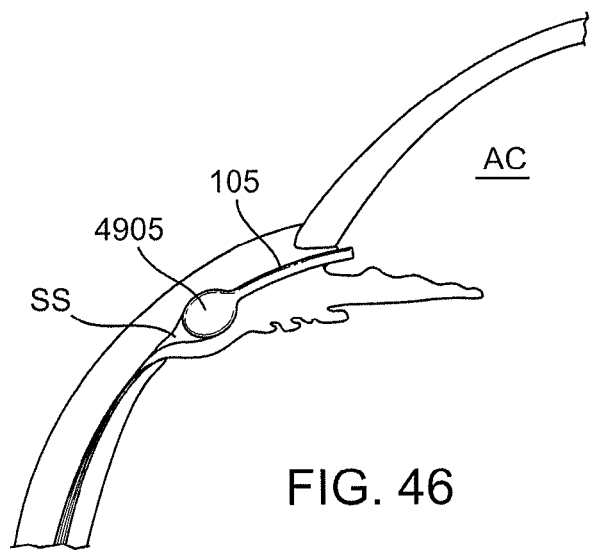
FIGS. 46 and 47 show embodiments of the bulbous element implant positioned in the suprachoroidal space.
Figure 47:
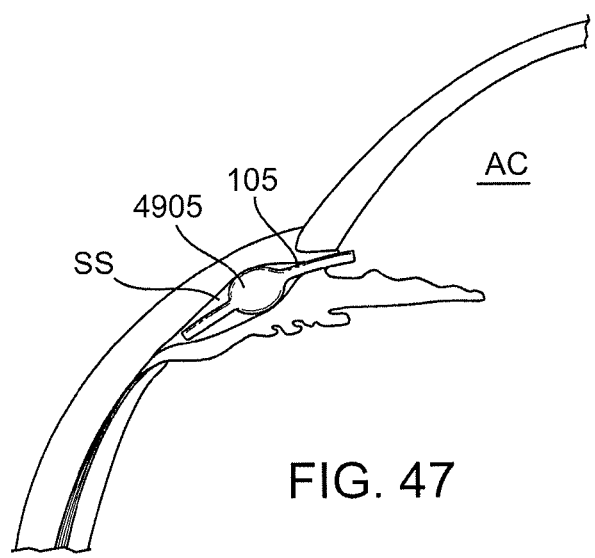

The use of the implant 105 with the bulbous element 4905 is now described with reference to FIGS. 46 and 47, which show two embodiments of the bulbous element implant positioned in the suprachoroidal space SS. As shown in FIGS. 46 and 47, the implant 105 is positioned such that a proximal end communicates with the anterior chamber AC and the bulbous element 4905 is positioned in the suprachoroidal space. The enlarged bulbous region 4905 forms a space or "lake" for accumulation of fluid within the suprachoroidal space. Because the lake is contained entirely within the suprachoroidal space and enclosed by tissue, the lake is not prone to infection and other complications. The lake can also be formed using an embodiment of the implant that does not have a bulbous element. A fluid can be flowed into the suprachoroidal space through the internal lumen of the implant. The fluid fills accumulates within the suprachoroidal space to form the lake.

In another embodiment, the lake is formed via hydrodissection. A delivery cannula can be positioned in the eye such that fluid can be flowed into the suprachoroidal space via the cannula. The fluid is flowed into the eye with a pressure sufficient to form a dissection plane within the suprachoroidal space. The fluid can then accumulate within the suprachoroidal space so as to form a lake.

Figure 48:
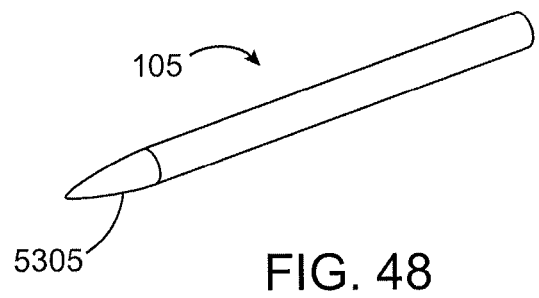
FIG. 48 shows an embodiment of the implant that includes a bullet-shaped tip member.

FIG. 48 shows an embodiment of the implant 105 that includes a distal tip member 5305 that is integrally formed with the implant. The tip member 5305 has a shape that is adapted to facilitate dissection into the suprachoroidal space. For example, the tip member 5305 can be "bullet" shaped in that the diameter of the tip member 5305 gradually reduces moving along the distal direction. The tip member 5305 can include one or more holes that communicate with the internal lumen of the implant. Alternately, the tip member 5305 can be without holes and holes can be placed on the side of the implant 105. The tip member 5305 can be manufactured of various materials, including stainless steel.

Figure 49:
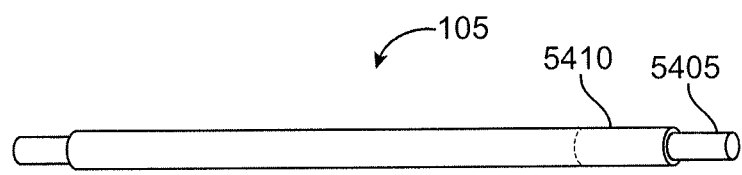
FIG. 49 shows an embodiment of an implant that mounts over a mandrel.

FIG. 49 shows an embodiment of an implant 105 that mounts over a mandrel 5405, which can be a portion of the applier 525 such that the mandrel 5405 can be incorporated into the delivery system. The implant 105 is adapted to conform to the shape of the mandrel 5405 when it is mounted on the mandrel, such as during delivery of the implant 105. When the mandrel 5405 is removed, the implant 105 transitions to a different shape. The implant 105 can be at least partially manufactured of a shape-memory material to accomplish the change in shape. In one embodiment, one or more Nitinol rings are disposed on the implant wherein the rings undergo a shape change to induce the implant to transition in shape. A Nitinol wire can also be threaded along the length of the implant to induce the shape change.

Figure 50:
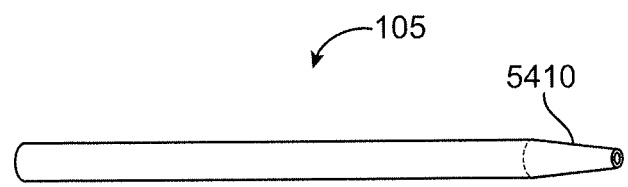
FIGS. 50 and 51A show embodiments of implant s that change shape after removal from a mandrel.

Different regions of the implant 105 can transition to different shapes. For example, the implant 105 can include a proximal region 5410 that is substantially round when the mandrel 5405 is positioned within the implant. When the mandrel 5405 is removed from the implant, the proximal region 5410 radially reduces in size while the remainder of the implant remains the same shape, as shown in FIG. 50. The proximal region 5410 can taper in size when the mandrel is removed such as to limit or meter flow through the implant. In addition, the proximal tip of the implant can flatten to an oval shape while the remainder of the implant remains round. Alternately, the proximal tip can remain round but of a reduce diameter relative to the remainder of the implant.

Figure 51A:
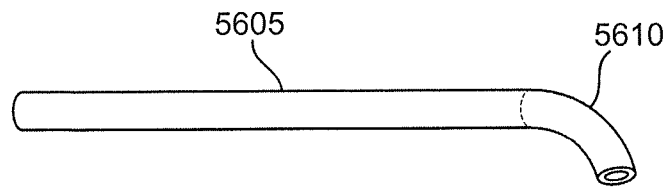

When the mandrel is removed, the implant 105 can transition to a shape that is particularly suited for placement and delivery into the suprachoroidal space. For example, with reference to FIG. 51A, the implant 105 can include a first region 5605 that transitions to a first contour or first radius of curvature and a second region that transitions to a second contour or second radius of curvature.

Figure 51B:
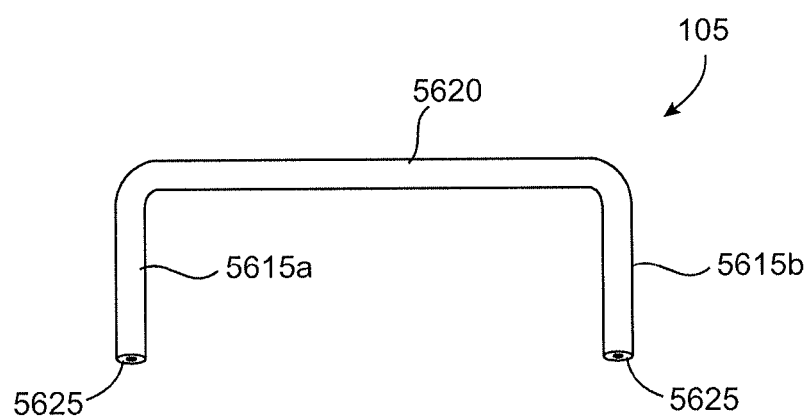
FIG. 51B shows another embodiment of an implant.
Figure 51C:
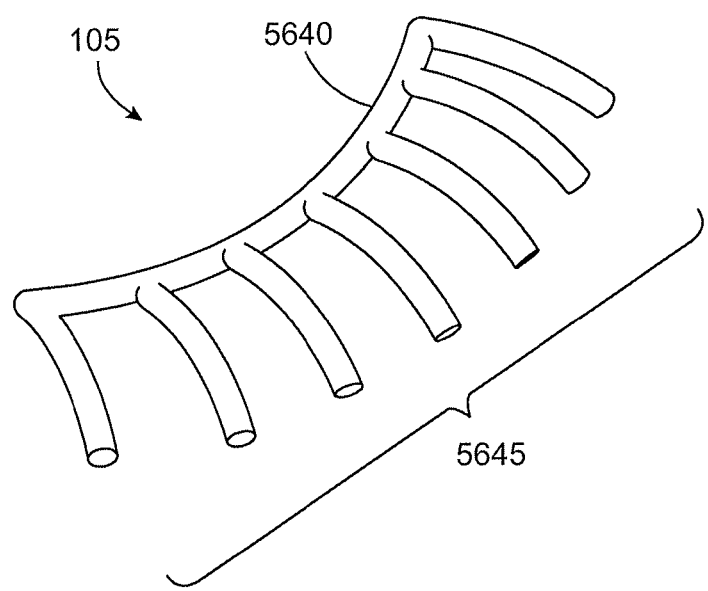
FIG. 51C shows another embodiment of an implant.
Figure 52:
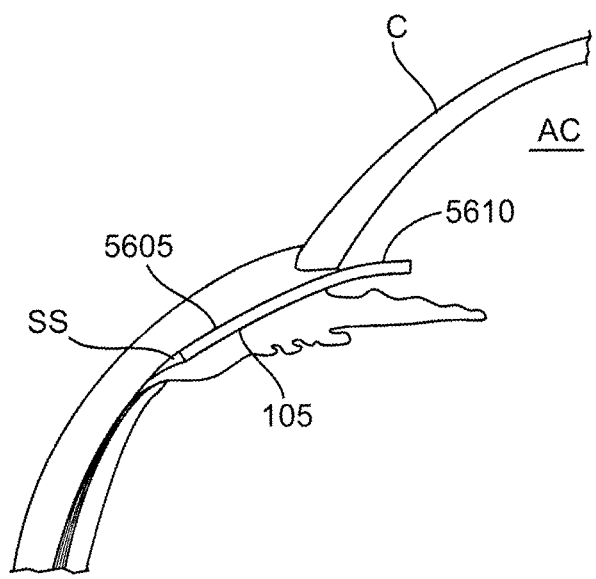
FIG. 52 shows an implant with a curved proximal region positioned in the eye.

FIG. 52 shows the implant of FIG. 51 positioned in the eye. The first region 5605 has a first radius curvature that complements the radius of curvature of the suprachoroidal space. The second region 5610 has a second radius of curvature that is tighter than the first radius such that the proximal tip of the implant is directed away from the cornea C and toward the anterior chamber AC. This reduces the likelihood that the proximal tip of the implant 105 will contact the cornea after placement of the implant.

FIG. 51B shows another embodiment of an implant 105 that has a staple shape. The implant 105 includes a pair of legs 5615a and 5615b that are connected by a connecting member 5620. In an embodiment, both of the legs 5610 have an internal lumen with a distal opening 5625 for inflow or outflow of fluid. The legs 5615 also have one or more proximal openings. The proximal openings can be located at the location where the legs connect to the connecting member 5620. Alternately, the connecting member 5620 can also have an internal lumen that communicates with the internal lumens of the legs 5615. The connecting member 5620 can include one or more openings that communicate with the internal lumens for inflow or outflow of fluid. In another embodiment, only one of the legs 5615 has an internal lumen while the other leg is solid and serves as an anchoring member.

In use, the implant 105 of FIG. 51B is positioned in the eye such that the distal opening 5625 of each leg 5615 communicates with the suprachoroidal space and the connecting member is positioned is located in the angle between the iris and the cornea. One or both of the legs 5615 provides a fluid passageway between the suprachoroidal space and the anterior chamber. If one of the legs 5615 does not include an internal lumen, then the non-lumen leg can serve as an anchor that secures the implant 105 in a fixed position in the eye.

FIG. 51C shows another embodiment of an implant 105. This embodiment includes a partially-annular connecting member 5640 and a plurality of legs 5645. The connecting member 5640 is partially annular in that it extends over a range of less than 360 degrees. For example, the connecting member 5640 can extend from about twenty degrees to greater than 180 degrees. The connecting member 5640 and the legs 5645 collectively reside within a curved plane that conforms to the curvature of a dissection plane that includes the suprachoroidal space. One or more of the legs 5645 can include an internal lumen that communicates with an inflow and outflow openings. In use, the implant 105 of FIG. 51C is positioned in the eye such that the connecting member 5640 sits within the angle between the iris and the cornea, while the legs 5645 extend into the suprachoroidal space. The legs 5645 can serve as fluid conduits and/or as anchors for securing the device in the eye.

Further Description of Methods

Figure 53:
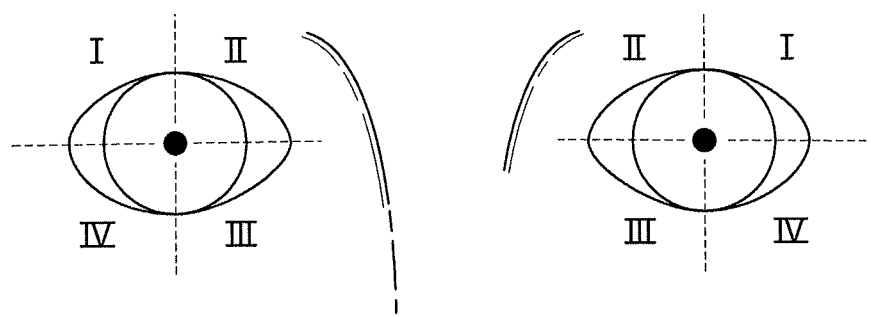
FIG. 53 shows a schematic, front view of the upper region of a patient's face including the two eyes.

There are various pathways of approach for delivering the implant into the eye using the delivery system such as the system shown in FIG. 6B. FIG. 53 shows a schematic, front view of the upper region of a patient's face including the two eyes. For reference purposes, the eyes are shown divided into four quadrants I, II, III, and IV when viewed from the front of the eye. For each eye, the quadrants I and III are located on the lateral side of the eye and the quadrants II and IV are located on the medial side of the eye. In one embodiment, the approach pathway passes through only a single quadrant. In other embodiments, the pathway passes through at least two quadrants, at least three quadrants, or through all four quadrants. In an exemplary implant delivery embodiment, the surgeon delivers the implant with the implant initially approaching the eye from quadrant I or IV such that the corneal incision is within quadrant I or IV. In another implant delivery embodiment, the implant approaches the eye from quadrant II or III. As described below, the location where the implant is implanted in the suprachoroidal space can be at various locations relative to the location of the incision. In an embodiment, the location where the implant is implanted in the suprachoroidal space is from 0 degrees to 180 degrees from the incision location. For example, the incision can be in quadrant I and the implant location is 180 degrees away in quadrant III. In another embodiment, the incision location and implant location are separated by at least 90 degrees or up to 90 degrees. The actual placement of the implant can be in any quadrant depending on the shape of the tip of the applier.

Figure 54A:
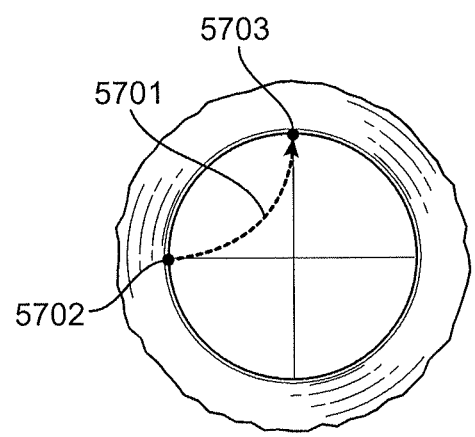
FIGS. 54A and 54B show perspective and plan views of an exemplary delivery pathway of the applier and implant during implantation of the implant into the eye.
Figure 54B:
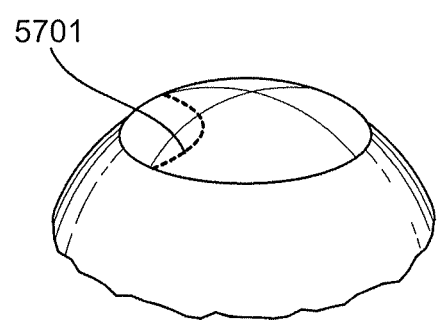

FIGS. 54A and 54B shows perspective and plan views, respectively, of an exemplary delivery pathway 5701 of the applier and implant during implantation of the implant into the eye. The delivery pathway 5701 begins at an incision location 5702 and moves toward dissection location 5703 where the implant dissects the scleral spur and approaches the suprachoroidal space. As mentioned, in another embodiment, the scleral spur is not dissected but is rather used as an anatomical landmark that guides the implant or delivery instrument toward the suprachoroidal space.

Figure 55A:
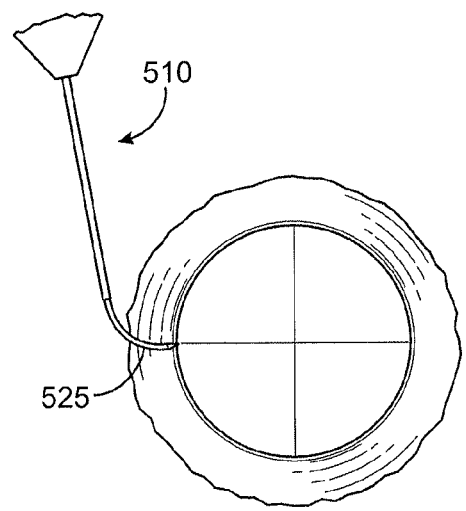
FIGS. 55A-55D show plan and perspective views of a delivery system being inserted into the eye.

In one embodiment, the incision location 5702 is along the axis that separates quadrants I and IV (i.e., at the "9 o'clock" or "3 o'clock" position of the eye) and the dissection location 5703 is approximately 90 degrees from the incision location (i.e., at the "12 o'clock" position of the eye). Such a delivery pathway is transcorneal in that it traverses over the cornea. However, the delivery pathway need not be transcorneal. FIGS. 55A-55D show the delivery system and attached implant traveling along the previously described delivery pathway. In FIG. 55A (front plan view) and FIG. 55B (perspective view), the delivery system 515 is in an initial approach position relative to the eye such that the distal end of the applier 525 is at the incision and about to penetrate into the eye. If the applier 525 is curved, the line of curvature of the applier 525 can be in various orientations. In one embodiment, the applier's line of curvature is initially oriented such that the curvature moves away from the interior of the eye.

Figure 55B:
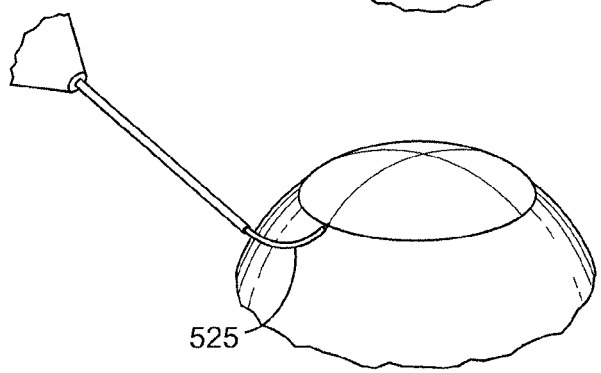
Figure 55C:
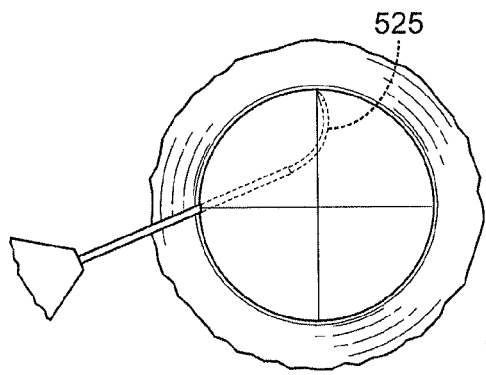
Figure 55D:
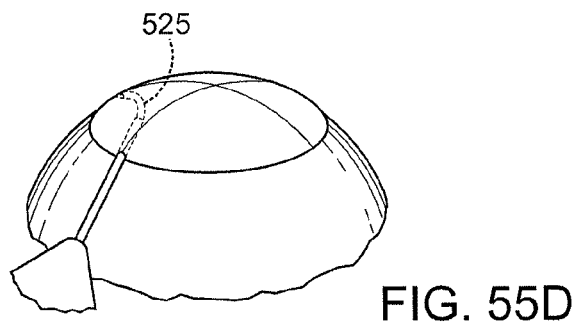

With reference now to FIG. 55C (front plant view) and FIG. 55D (perspective view), the applier and implant have passed over the cornea such that the distal tip of the applier has passed through the anterior chamber and is at or near the scleral spur. During such passage, the handle of the delivery system is rotated and translated to align the applier's curvature with the curvature of the suprachoroidal space. The tip of the applier 525 is then advanced and passed through the scleral spur or below the scleral spur to position the implant 105 within the suprachoroidal space.

Figure 56:
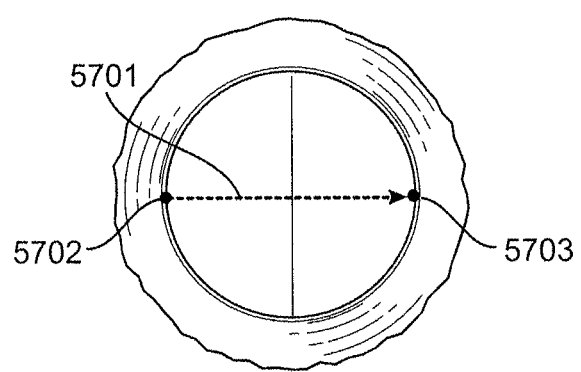
FIG. 56 shows a plan view of an exemplary delivery pathway.
Figure 57:
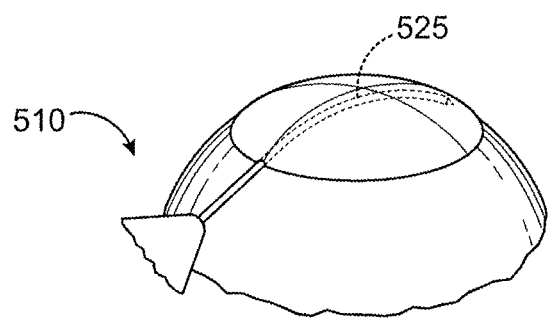
FIG. 57 shows a perspective view of an alternate delivery pathway into the eye.

FIG. 56 shows an alternative transcorneal delivery pathway 5701 wherein the incision location 5702 and the dissection location 5703 are approximately 180 degrees from one another. FIGS. 55A, 55B, and 57 show the delivery system and attached implant traveling along such a delivery pathway. In the initial approach orientation, the delivery system 510 is positioned such that the tip of the applier 525 is at the incision location (such as shown above in FIGS. 55A and 55B). The handle component 515 is translated and/or also rotated such as approximately ninety degrees so that the distal tip of the applier 525 resides within a plane that intersects the scleral spur or is just below the scleral spur. The line of curvature of the applier 525 is not yet necessarily aligned with the curvature of the eye in quadrant I. In addition, the applier is still positioned at or near quadrant I.

With reference now to FIG. 57, the delivery system 510 is translated such that the distal tip of the applier 525 moves near or into quadrant IV. The translation can occur either by translating the handle component 510 or by causing the advancing member 530 and applier 525 to elongate. In conjunction with the translation, the handle component 510 is rotated to re-orient the applier 525 such that the line of curvature substantially aligns with the curvature of the eye, specifically the curvature of the dissection plane, which extends through the suprachoroidal space. At this stage, the tip of the applier is directed toward the scleral spur and the line of curvature extends toward the suprachoroidal space. The applier 525 can then be distally advanced into the suprachoroidal space and the implant dismounted from the applier so as to place the implant in or near quadrant IV.

Figure 58A:
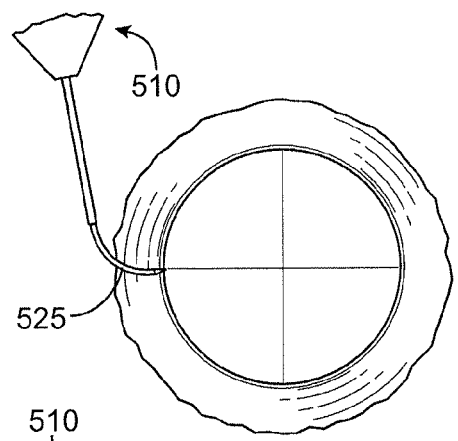
FIGS. 58A-58D show yet another delivery pathway into the eye.
Figure 58B:
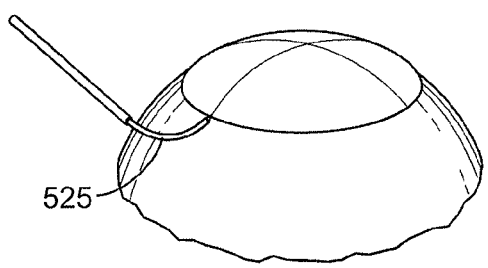
Figure 58C:
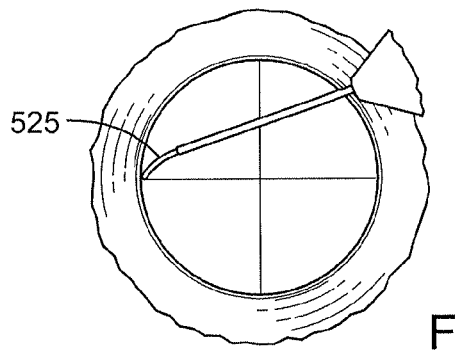
Figure 58D:
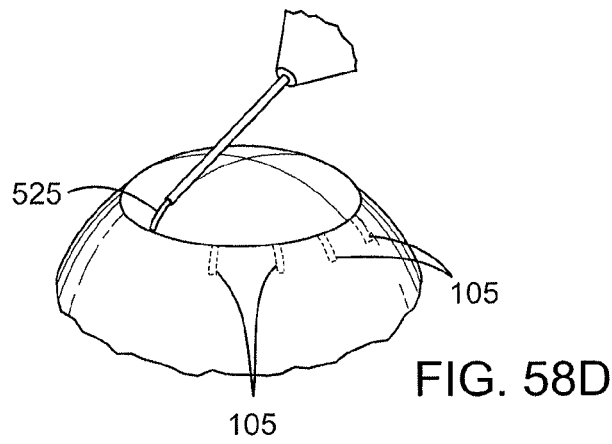

As mentioned, the delivery system 510 can approach the eye in other manners than described above. In another embodiment, the incision location and the dissection location are within the same quadrant. In such an embodiment, the distal tip of the applier passes through an incision in the cornea that is closer to the scleral spur, rather than from across the eye as in the previously-described embodiments. FIGS. 58A-58D show an example of such a delivery pathway. In FIG. 58A (plan view) and FIG. 58B (perspective view), the delivery system 510 in an initial approach position (such as in quadrant I). The line of curvature of the applier 525 is not yet aligned with the curvature of the eye. The delivery system is translated so that the applier 525 penetrates the eye. The handle component 510 is then rotated such that the applier is directed toward the scleral spur and the line of curvature extends toward the suprachoroidal space, as shown in FIG. 58C (plan view) and FIG. 58D (perspective view). The applier 525 can then be distally advanced through or adjacent the scleral spur and into the suprachoroidal space. The whole procedure occurred with the applier being positioned in a single quadrant. The delivery system 510 can be used to approach the eye from various approach angles so as to position multiple implants 105 around the circumference of the eye, as shown in FIG. 58D. The implants 105 can be interspersed or grouped in clusters around the entire circumference or a portion of the circumference of the eye.

A further embodiment is one where multiple implants are loaded into a delivery system and able to be delivered into various locations around the anterior chamber to the suprachoroidal space in a fashion such that the delivery device is not removed from the anterior chamber. The device is moved throughout the anterior chamber and has a multi-fire chamber such that as one implant is delivered from the applier 525, another implant is loaded onto the applier 525 and so on. This allows multiple implant placements without reloading or using another device.

Infusion

During the procedure, fluid can be infused into the eye in order to stabilize the pressure in the anterior chamber, such as prior to, during, or after installation of an implant. Infusion can also be used to maintain a clear field of view along the delivery pathway during delivery of the implant. There is a risk that the pressure within the anterior chamber can adversely drop due to loss of fluid, which can possibly result in collapse of the anterior chamber. In order to counter a drop in pressure, fluid can be infused into the anterior chamber in order to maintain the pressure within a desired range. The fluid can be infused through a dedicated internal lumen in the applier or infused through the lumen in the implant. The fluid can also be infused through a separate system that interfaces with the eye. For example, a cannulized member can be inserted into the anterior chamber and coupled to a source of fluid, such as a bag or saline or other biocompatible fluid source. If the pressure within the anterior chamber drops below a threshold value, the resulting pressure differential can cause fluid to automatically flow into the anterior chamber through the cannulized member.

A dye can be infused into the eye in order to provide visualization. The dye can be viewable through a visualization instrument. As the dye flows into the suprachoroidal space, it provides a visualization of flow. The dye can be photoactivated such that it shows aqueous humor dispersion when a certain type of light is applied to the dye. In addition, an ultrasound or Doppler can be used (such as by integrating a Doppler tip on the delivery device) to visualize or sense flow, or the rate of flow, through the suprachoroidal space.

Implants in Use with Closed Angle Glaucoma

Figure 59:
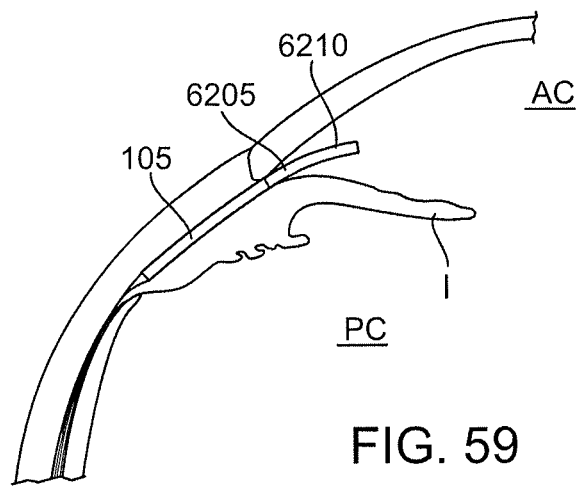
FIG. 59 shows an implant having an extension sized and positioned such that a proximal end is positioned over a crest of the iris.
Figure 60:
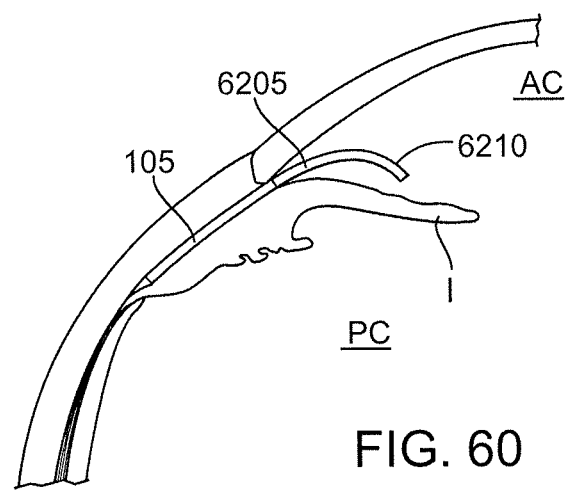
FIG. 60 shows an implant with a curved extension positioned in the eye.

With reference to FIG. 59, it is possible for aqueous humor to accumulate within the posterior chamber PC such that at least a portion of the iris I is forced upward into the anterior chamber. Due to the pressure in the posterior chamber, the iris can angle toward the cornea so as to form a crest and then fall back toward the posterior chamber. In such a case, the base of the iris might interfere with or block the opening on the proximal end of the implant. An implant 105 can be used having an elongated length or extension 6205 that repositions the proximal end of the implant 105 to a location that is not blocked or interfered with by the iris. For example, as shown in FIG. 59, the extension 6205 is sized and positioned such that a proximal end 6210 is positioned over the crest of the iris. The extension 6210 can be made of a soft or flexible material so as to minimize or eliminate the risk of damage to the cornea should the proximal end 6210 contact the cornea. In another embodiment, shown in FIG. 60, the extension 6205 has a curved shape such that the distal end 6210 is angled away from the cornea.

Figure 61:
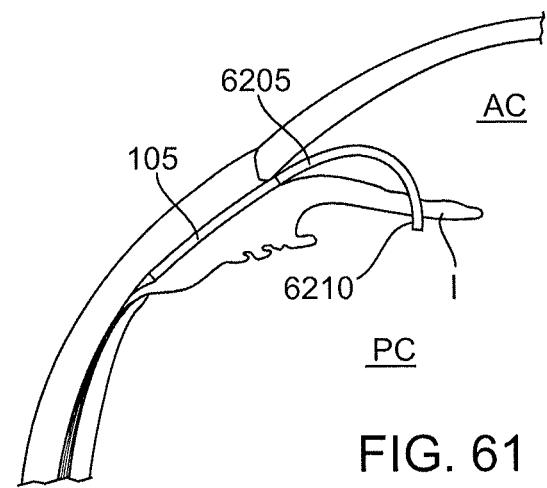
FIG. 61 shows another embodiment wherein the implant extends through the iris such that the proximal end and the internal lumen of the implant communicate with the posterior chamber.

FIG. 61 shows another embodiment wherein the implant extends through the iris I such that the proximal end 6210 and the internal lumen of the implant communicate with the posterior chamber. The implant permits aqueous humor to flow out of the posterior chamber to release pressure in the posterior chamber. The implant 6205 can extend through various locations of the iris and can be manufactured of a material that is compliant, such as silicone. The embodiment shown in FIG. 61 can be used in place of or to conjunction with an iris iridoplasty procedure. In addition, the delivery system can be adapted such that a distal end of the applier has a tip, such as an RF tip as described in more detail above, that is adapted to perform an iridoplasty without the use of the implant.

Trans-Scleral Delivery of Implant

In the previously-described embodiments, the implant 105 is delivered by passing the implant through a corneal incision or puncture. The surgeon then passes the implant through the anterior chamber, across the scleral spur, and into the suprachoroidal space. In another embodiment, the surgeon makes an incision in the sclera to provide a trans-scleral delivery of the implant into the eye. After making the scleral incision, the surgeon passes the proximal end of the implant through the scleral incision sclera into suprachoroidal space. The surgeon then pushes the implant toward the anterior chamber, such as via the scleral spur, until the proximal region of the implant is positioned in the anterior chamber and the distal region of the implant is positioned in the suprachoroidal space.

Figure 62:
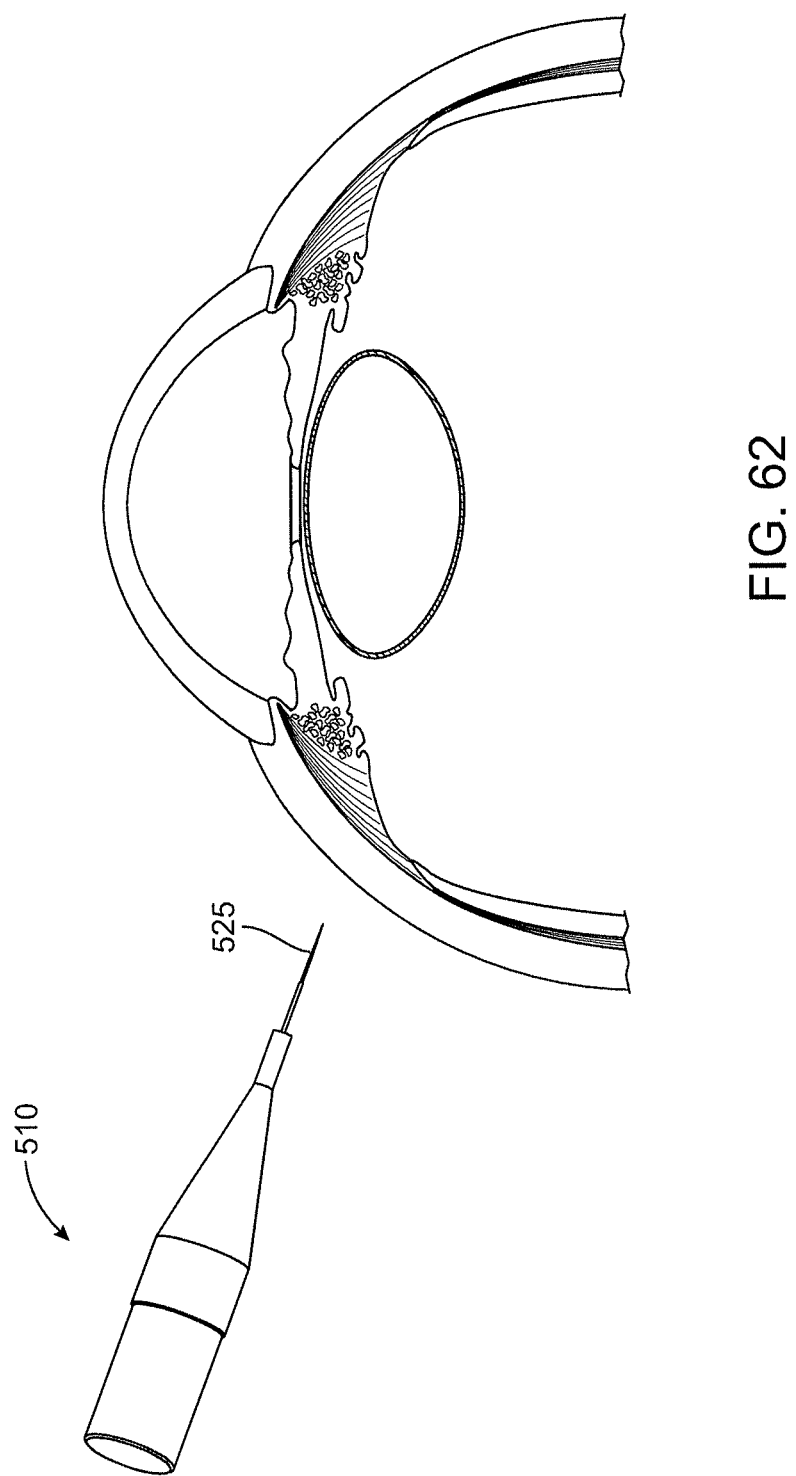
FIGS. 62 and 63 show a trans-scleral delivery approach for the implant.
Figure 63:
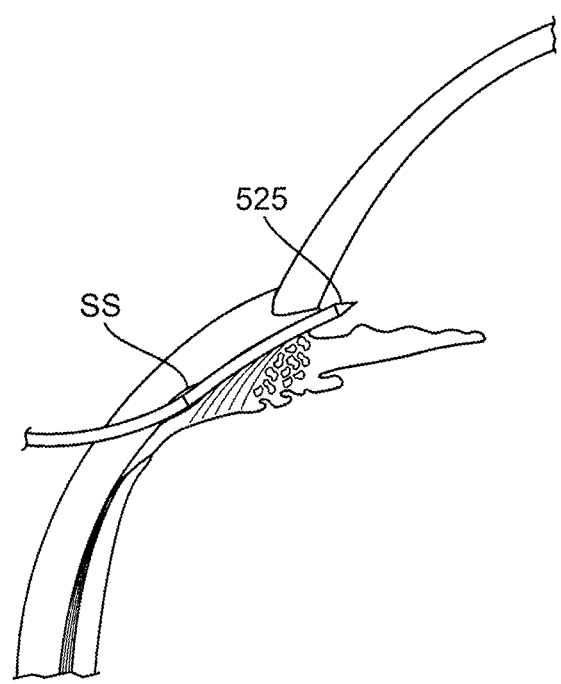

The trans-scleral approach is described in more detail with reference to FIGS. 62 and 63. FIG. 62 shows the delivery device 510 positioned such that the distal tip of the applier 525 or the implant 105 itself can penetrate through an incision in the sclera. The applier 525 or implant 105 can be used to make the incision or a separate cutting device can be used.

After the incision is formed, the applier 525 and attached implant advances through the sclera and into the suprachoroidal space. The surgeon advances the applier 525 until a proximal region of implant 105 is positioned within the anterior chamber and a distal region is within the suprachoroidal space, as shown in FIG. 63. The surgeon then releases the implant 105 off of the applier 5252 so that the implant provides a fluid passageway between the anterior chamber and the suprachoroidal space. In one embodiment, the applier 525 travels along a pathway from the suprachoroidal space toward the scleral spur such that the applier crosses through the or past the scleral spur on the way to the anterior chamber. The applier 525 can be pre-shaped, steerable, articulating, or shapeable in a manner that facilitates the applier passing through the suprachoroidal space along a proper angle or pathway.

As discussed above, various devices can be used to assist in guiding the delivery device and implant into a proper position in the eye. For example, a guidewire can be used to guide the applier or the implant over the guidewire to the proper location in the eye. The guidewire or the delivery can be equipped with a fiber optic that provides direct visualization of the eye during delivery of the implant. In another embodiment, one or more imaging systems can be used during deliver of the device. Such imaging systems can include, for example, ultrasound (UBM), optical coherence tomography (OCT), and endoscopic viewing. OCT performs cross-sectional imaging of internal tissue microstructure by measuring the echo time delay of backscattered infrared light using an interferometer and a low coherence light source. For example, the Visante® OCT system from Zeiss Medical (Germany) can be used to non-invasively image during placement of the implants, or to confirm placement once the implant has been place, post procedure and also at follow up. In addition, certain ultrasonic systems and those providing enhanced tactile feedback or ultrasonic guidance can be used, for example devices shown in U.S. Pat. Nos. 6,969,384 and 6,676,607, incorporated by reference herein in their entirety, Endoscopes, such as the i-Scope™, and UBM devices (high frequency ultrasound) can be used such as those made by Ophthalmic Technologies, Inc. (Ontario, Canada).

In another embodiment, the implant is deployed into the eye in combination with a cataract treatment procedure. In a cataract treatment procedure, the surgeon makes an incision in the cornea and inserts a viscoelastic material into the eye through the incision. The surgeon then removes the cataract through the incision. In combination with such a procedure, the surgeon implants an implant 105 into the eye in the manner described above. A new lens can be implanted into the eye pursuant to this procedure. The implant can be implanted either before or after removal of the lens.

Expansion Members and Materials

As mentioned, the implant can be manufactured of, coated or layered with a material that expands outward. The material can expand either before or after the implant is placed in the eye. Several exemplary embodiments are described below wherein the expansion material comprises hydrogel. Hydrogel is a three-dimensional network of polymer chains that are cross-linked through either chemical or physical bonding. The polymer chains are hydrophilic in nature and can absorb water. Thus, when hydrogel is in the presence of abundant fluid it swells. Although the exemplary embodiments below are described as incorporating a hydrogel, various types of expansion material can be used including, for example, foam, lyophilized collagen, or any material that gels, swells, or otherwise expands, such as upon contact with body fluids.

Figure 64:
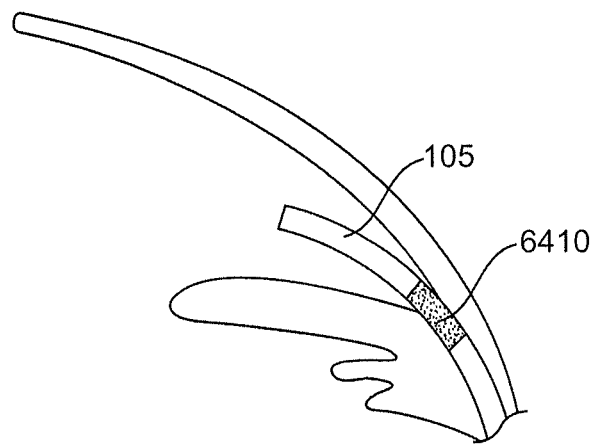
FIG. 64 shows an implant positioned in the eye with a first end of the implant in the anterior chamber and a second end of the implant in the suprachoroidal space.
Figure 65:
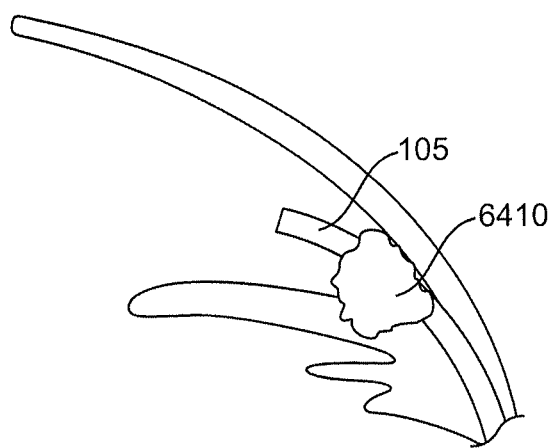
FIG. 65 shows the implant of FIG. 64 with a hydrogel sheath in an expanded or swelled state.

In an embodiment, hydrogel is used with the implant to seal openings in the implant or in adjacent anatomical structures such as to prevent fluid from flowing through the opening. For example, hydrogel can be utilized seal one or more openings to prevent aqueous humor from passing through the opening. The implant can include a layer or coating of hydrogel, such as in the form of a hydrogel sheath, that expands to seal an opening. FIG. 64 shows an implant 105 positioned in the eye with a first end of the implant in the anterior chamber and a second end of the implant in the suprachoroidal space. A gap or opening may be located adjacent the implant 105 in the region of the scleral spur for example. The implant 105 has a hydrogel structure, such as a hydrogel sheath 6410 that is positioned adjacent the opening. In FIG. 64, the hydrogel sheath 6410 is in a pre-expanded state. FIG. 65 shows the implant 105 with the hydrogel sheath 6410 in an expanded or swelled state. The hydrogel has expanded to a volume that fills or otherwise seals the volume around the implant 105 such that fluid is prevented from flowing from the anterior chamber into the suprachoroidal space except through the implant. Hydrogel can be used to fill or seal any opening on the implant or in adjacent anatomy.

In another embodiment, hydrogel is used with the implant to provide swelling to enlarge the geometry or any other feature of the implant, such as to aid in retention of the implant in the eye. In such an embodiment, the implant can be coated with or at least partially manufactured of a hydrogel wherein the hydrogel is initially in a state of reduced size, such as prior to implantation in the eye. During or after the implant is implanted in the eye, the hydrogel is expanded to a size that anchors the implant in place. In another embodiment, the internal lumen of the implant can be partially filled with a hydrogel. During or after implantation of the implant, the hydrogel is then expanded to maintain the lumen in an open state.

The manner in which the hydrogel expands to anchor the implant can vary. In an embodiment, hydrogel is positioned on the implant such that the hydrogel causes an anchoring member on the implant to move from a retracted state to an expanded state wherein the anchoring member anchors against an anatomical structure in the expanded state. FIGS. 66A-67 show an embodiment of an implant having anchoring members 6610 comprised of a plurality of prongs or arms that are adapted to expand outward.

FIG. 66A shows a side view of the implant and FIG. 66B shows a front view of the implant prior to expansion. Although FIG. 66B shows the implant as having a rectangular-like cross-sectional shape, it should be appreciated the cross-sectional shape can vary and can include circular, oval, irregular, and other shapes. FIG. 67 shows a side view of the implant with the anchoring members 6610 in the expanded state. In an initial state, shown in FIGS. 66A and 66B, the anchoring members 6610 are retracted or constrained to a position of reduced dimension D. A hydrogel H is located between the anchoring members 6610. The hydrogel H can be installed on the implant by a dipping or molding process or using another process. During or after implantation of the implant into the eye, the hydrogel H is caused to expand outward as represented by the arrows E in FIG. 67. The expansion of the hydrogel H causes the anchoring members 6610 to separate from one another and also expand outward to increase the dimension D of the implant at the outer tips of the anchoring members 6610. In the expanded state, the anchoring members 6610 lodge against or provide an interfering engagement with the eye anatomy to anchor the implant in place.

Figure 68:
FIGS. 68 and 69 each show an implant having an anchoring member comprised of an expandable sheath positioned along the length of the implant.
Figure 69:
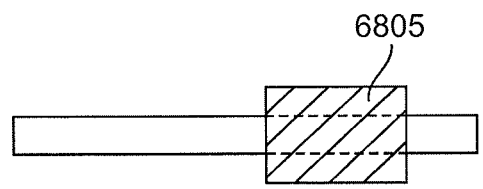
Figure 70:
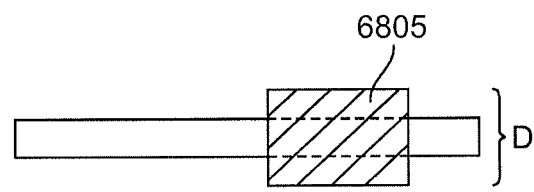
FIGS. 70 and 71 show the implants of FIGS. 68 and 69, respectively, with the anchoring members in expanded states.
Figure 71:
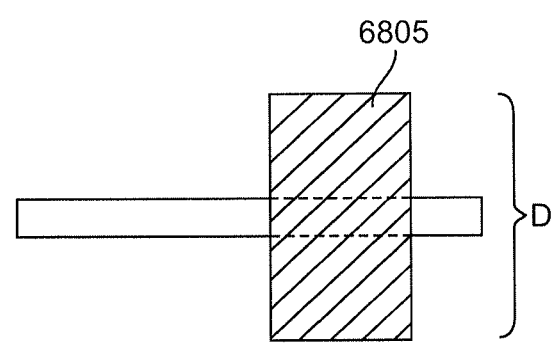

In another embodiment, the anchoring member can be entirely or partially manufactured of hydrogel. FIGS. 68 and 69 each show an implant having an anchoring member 6805 comprised of an expandable sheath positioned along the length of the implant. In FIGS. 68 and 69, the anchoring members 6805 are in a state of reduced size. During or after implantation of the implant 105 into the eye, the hydrogel anchoring member 6805 is caused to expand outwardly. FIGS. 70 and 71 show the implants with the anchoring members 6805 in expanded states relative to the states shown in FIGS. 68 and 69. The anchoring members 6805 have expanded to a size of increased dimension D. The increase in dimension can be in three dimensions or in two dimensions. The relative change in size from the reduced-size state to the expanded-size state can vary. For example, the anchoring member 6805 in FIGS. 69 and 71 has undergone a greater percentage expansion in size than the anchoring member in FIGS. 68 and 70.

Figure 72A:
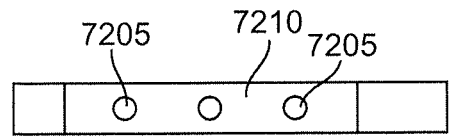
FIGS. 72A and 72B show side and top views of a tubular implant having expandable anchoring members comprising finger-like projections.
Figure 72B:
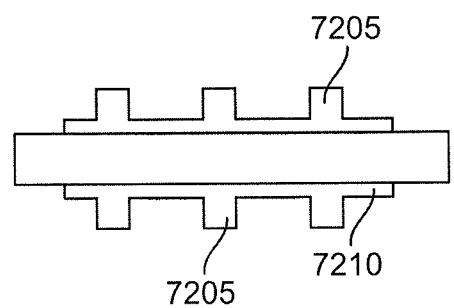

FIGS. 72A and 72B show side and top views of a tubular implant having expandable anchoring members 7205 comprising finger-like projections that extend radially outward from the tubular body of the implant. The anchoring members 7205 can be individually connected to the tubular body or they can be interconnected by a sheath region 7210 that mounts over the tubular body, such as what is shown in the figures.

Figure 73A:
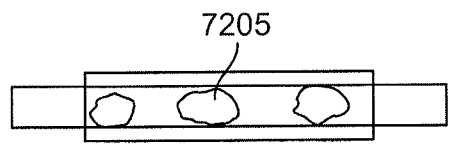
FIGS. 73A and 73B show side and top views of the implant of FIGS. 72A and 72B with the anchoring members in expanded states.
Figure 73B:
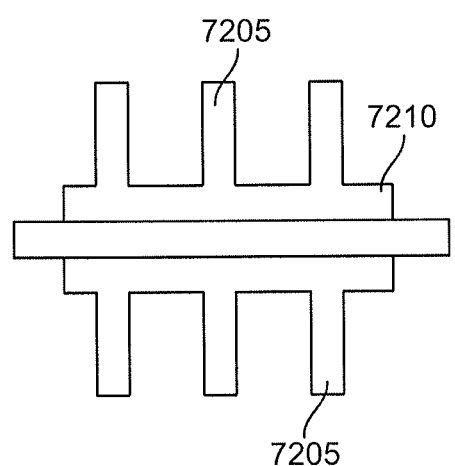

The anchoring members 7205 and sheath region 7210 can be partially or entirely comprised of a hydrogel material. FIGS. 72A and 72B show the anchoring members 7205 and the sheath region 7210 in a state of reduced size. During or after implantation of the implant in the eye, the hydrogel of the anchoring members 7205 and the sheath region 7210 is caused to transition to a state of expanded size, as shown in the side and top views of FIGS. 73A and 73B, respectively. The finger-like anchoring members 7205 and the sheath region 7210 to which they connect have expanded radially-outward such that they can anchor against adjacent tissue to secure the implant in a fixed position in the eye.

Any of the anchoring members described herein can be formed entirely or partially of hydrogel, silicone hydrogel, or any other expandable material. The anchoring members can be a powdered hydrogel or can be dipped in solvent-based hydrogel during manufacture. Alternately, the anchoring members can be formed of internally-positioned "sticks" or rods of hydrogel over which silicone is molded.

In another embodiment, hydrogel is at least partially used as an actuation member to cause the implant or a movable portion of the implant to move from a first state to a second state such as to increase retention capabilities of the implant. The hydrogel can also serve as an actuation member with respect to adjacent tissue when the implant is implanted in the eye. For example, the hydrogel can expand to push, move, or otherwise manipulate the tissue, such as to bluntly dissect the tissue or to push or "tent" the tissue outward to form a space or a "lake" for accumulation of fluid within the suprachoroidal space.

Figure 74:
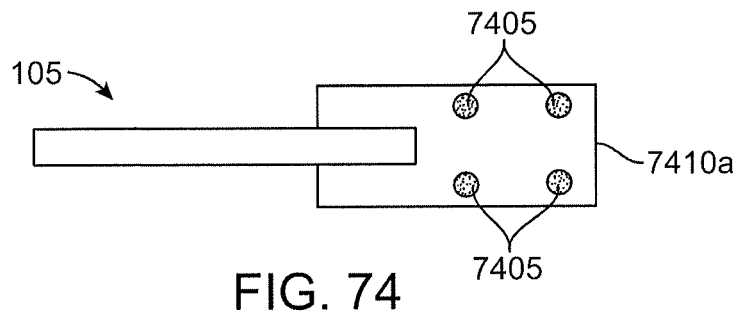
FIGS. 74 and 75 show top and side views, respectively, of a tubular implant having actuation members at least partially formed of hydrogel.
Figure 75:
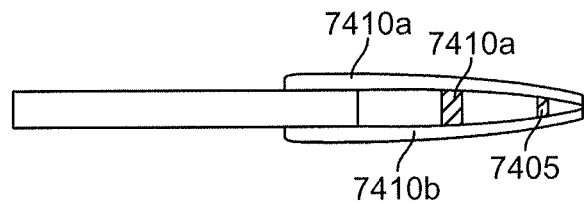
Figure 76:
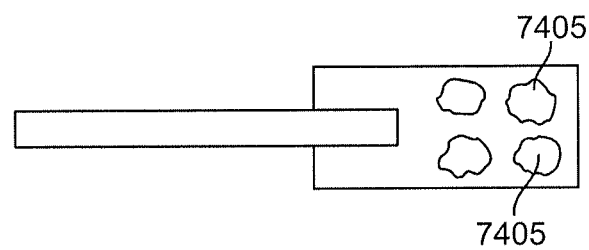
FIGS. 76 and 77 show top and side views, respectively, of a tubular implant having actuation members in an expanded state.
Figure 77:
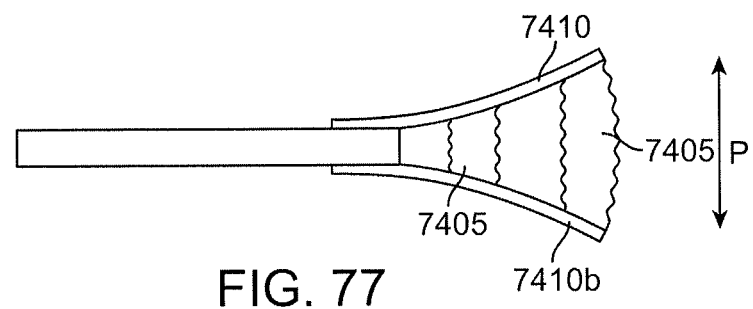

FIGS. 74 and 75 show top and side views, respectively, of a tubular implant having actuation members 7405 at least partially formed of hydrogel. The implant 105 has a pair of anchor members such as plates 7410a and 7410b that are positioned in a cantilevered relationship with the tubular body. The actuation members 7405 are in the form of pellets or pillars that are positioned between the plates 7410a and 7410b, as shown in FIG. 75. If the actuation members 7405 are hydrogel, then they can be attached to the plates in a manner described below. In an initial state, the plates 7410a and 7410b are coated toward one another. During or after implantation of the implant into the eye, the actuation members 7405 are caused to expand to a state of increased size, such as shown in FIGS. 76 and 77. As the actuation members expand, they push the outer tips of the plates 7410a and 7410b away from one another as represented by the arrow P in FIG. 77. The separated plates 7410a and 7410b can serve as anchoring members and/or a space forming feature that creates a lake for accumulation of fluid within a region of the eye when the implant is implanted in the eye.

Figure 78:
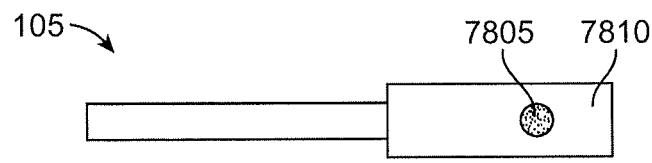
FIGS. 78 and 79 show top and side views, respectively, of another embodiment of a tubular implant that utilizes hydrogel as an actuation member.
Figure 79:
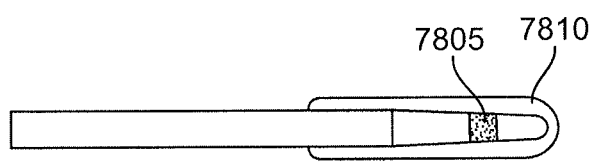
Figure 80:
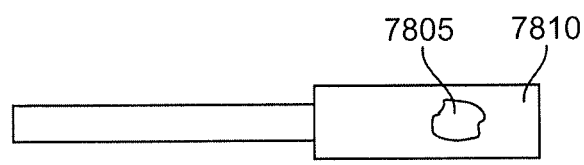
FIGS. 80 and 81 show top and side views, respectively, of a tubular implant having actuation members in an expanded state.
Figure 81:
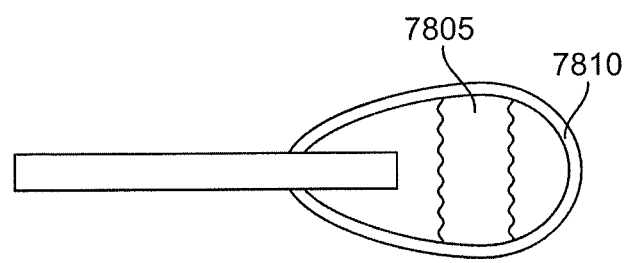

FIGS. 78 and 79 show top and side views, respectively, of another embodiment of a tubular implant 105 that utilizes hydrogel as an actuation member. The implant 105 includes one or more actuation members 7805 at least partially formed of hydrogel. The actuation member 7805 is positioned within an expandable, tubular ring member 7810 mounted on the tubular body of the implant. The actuation member 7805 is in the form of a pellet. In an initial state, the ring member 7810 has a first radial dimension. During or after implantation of the implant into the eye, the actuation member 7805 expands to a state of increased size, such as shown in FIGS. 80 and 81. As the actuation member 7805 expands, it causes at least a portion of the ring member 7810 to expand to an increased radial dimension, as shown in FIG. 81. The expanded ring member 7810 can serve as an anchoring member and/or a space-forming feature that creates a lake for accumulation of fluid within a region of the eye.

Figure 82:
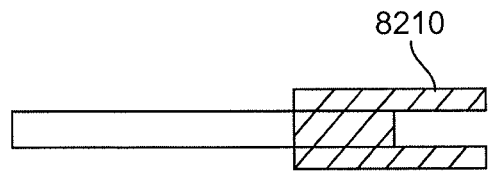
FIGS. 82-85 show an embodiment of an implant that includes an expandable member formed at least partially of hydrogel.
Figure 83:
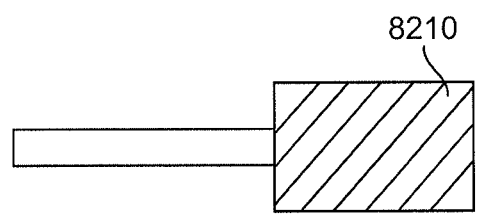
Figure 84:
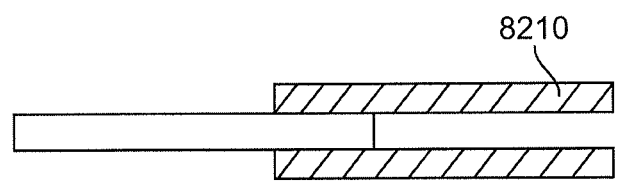
Figure 85:
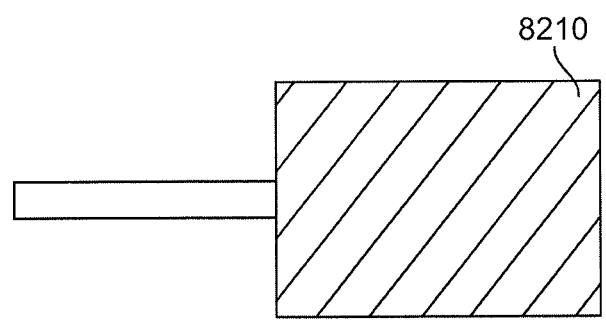

In another embodiment, the implant includes an expandable member that expands outward to create a space, lake or region to provide a path for fluid, such as aqueous humor, to drain or to dwell in. FIGS. 82-85 show an embodiment of an implant that includes an expandable member 8210 formed at least partially of hydrogel. The expandable member 8210 comprises a pair of plates that are cantilevered from the tubular body of the implant in a manner similar to the embodiment of FIGS. 74-77. The plates can be perforated for permitting fluid flow therethrough. FIGS. 82 and 83 show side and top views, respectively, of the expandable member 8210 in a state of reduced size. During or after implantation into the eye, the expandable member 8210 expands in size in one or more dimensions as shown in FIGS. 84 and 85. The expanded member 8210 can serve as an anchoring member and/or a space-forming feature that creates a lake for accumulation of fluid within a region of the eye.

In any of the embodiments that use hydrogel, the type and characteristics of hydrogel can vary. The hydrogel can be obtained from any of a variety of sources, such as Cardiotech Hydroslip C, Akina hydrogel, Estane Tecophilic TG-2000-V and HP-60D-20. The composition of the hydrogel can vary and can include urethanes, acrylamides, silicones, acrylics, polysaccharides, poly(N-vinylpyrrolidones), poly(hydroxyethylmethacrylate), other polymers, and other molecules. Moreover, various formations and manufacturing methods can be used, including solvent dipping, casting, injection molding, compression molding, insert molding, etc.

The hydrogel can swell to various increased sizes relative to an initial reduced size. In an embodiment, the hydrogel swells to about 200% to about 400% of the original sizes after implantation in the eye.

Hydrogel "loading" or "load" as used herein refers to the percentage of hydrogel in the solution or how much hydrogel is dissolved in the solvent, such as when dip-coating a device or a part of the device. After dipping the device in a hydrogel solution, the solvent is driven off leaving a layer of hydrogel on the device. The hydrogel load affects the viscosity of the solution. The viscosity of the solution affects the thickness of the hydrogel coating. The percent hydrogel in the solution (aka "load") can vary as can the number of times the device is dipped into the hydrogel solution. In an exemplary and non-limiting embodiment, the hydrogel is loaded between 5% and 40% in solvent by weight. Lower hydrogel loads can be offset by increasing the number of dips into the solution. In other words, a "thinner" hydrogel solution can be used to build up a thicker coating by increasing the number of times the part is dipped in the solution.

The hydrogel can be attached or secured to the implant in various manners. In this regard, an attachment mechanism attaches the hydrogel to the remainder of the implant. In an embodiment, hydrogel is attached to the implant by polymerizing a thin layer of acrylic onto the contact surface of the implant and then covalently bonding or cross linking the hydrogel to the acrylic, or by polymerizing the hydrogel to the acrylic. There are several chemical techniques that could be used to chemically bond the hydrogel. Various techniques can be used to prevent the hydrogel from detaching from the implant as the hydrogel is hydrated and expands. The part that expands may be held or trapped mechanically with the implant so that during expansion there are no bonds to break. For example, the hydrogel can be entirely or partially positioned inside a cage attached to the implant. During expansion, the hydrogel expands out of or through slots in the cage. Alternately, the cage itself can expand with the hydrogel. In another embodiment, a semi-permiable membrane is coated over the hydrogel and the implant. In an embodiment, the membrane is configured to stretch with the hydrogel to retain the hydrogel to the implant. The membrane can be water-permeable to permit hydration of the hydrogel through the membrane. In another embodiment, the membrane bursts upon expansion of the hydrogel to release the hydrogel from containment within the membrane.

In an embodiment, the attachment mechanism between the hydrogel and the implant comprises a plurality of pores in which the hydrogel is at least partially positioned. For example, the implant may be a tubular member formed of a porous material. A hydrogel material is reaction cast onto the tube such that the hydrogel is polymerized into the pores of the tube. Upon implant into the eye, the hydrogel is hydrated so that at least a portion of the hydrogel expands outward from the pores while a portion of the hydrogel remains attached to the implant within the pores.

The rate of expansion of the hydrogel expansion can be controlled by coating the hydrogel with a resorbable coating that acts as a temporary barrier that regulates the rate at which water contacts the hydrogel and thereby regulates the rate of expansion of the hydrogel. In another embodiment, the hydrogel is filled with a substance or material must be displaced by water. The substance or material displaces more slowly than pure hydration. This can be achieved using an unreactive polar or semi polar diluent added to the polymerization of the hydrogel so it is trapped inside the unhydrated hydrogel before hydration. It would have a sufficiently low molecular weight to get out by displacement with water during hydration.

In an exemplary manufacturing process, an implant or part of the implant formed of silicone and/or polyimide is dipped directly into a hydrogel to form the hydrogel members. In another manufacturing process, a glue such as cyanoacrylate glue is used as an intermediate layer to bind the hydrogels to the polyimide or silicone implant.

The implant can use expansion material other than hydrogel. For example, the expansion material can be an elastic or superelastic material such as Nitinol. The implant can include an anchoring member and/or lake-forming member that is formed of an elastic or superelastic material. In an embodiment, the implant has an expanding member at least partially formed of superelastic Nitinol wire. The size of the wire can vary and in one embodiment the size is in the range of 0.001"-0.010" in diameter. The wire can be round or flat. An elastic expanding member can be formed of silicone, such as silicone of 30-80 durometer in thicknesses of 0.003"-0.020". Other materials, such as a swelling acrylic can be used to manufacture expanding members for retention and/or lake forming purposes. The acrylic can be, for example, machinable or injection moldable acrylic such as PERSPEX from ICI, Benz R&D acrylic etc. that absorb about 24% of its weight in water and softens as it swells.

Figure 86:
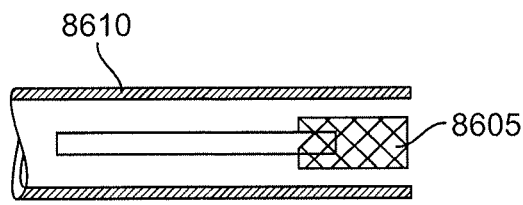
FIGS. 86 and 87 show an exemplary embodiment of an implant having an expanding member formed of an elastic or superelastic material.
Figure 87:
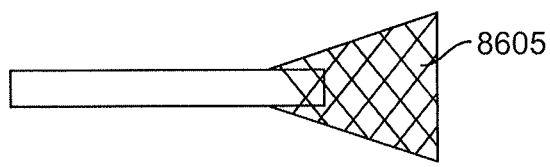

FIGS. 86 and 87 show an exemplary embodiment of an implant having an expanding member 8605 formed of an elastic or superelastic material. The expanding member 8605 comprises a mesh or braided structure that is biased toward an expanded state as shown in FIG. 87. During implantation, the implant is positioned within an outer sheath 8610 or other structure that constrains the expanding member 8605 in a state of reduced size. When the implant is positioned in the desired location for implantation in the eye, the implant is released from the sheath 8610 so that the expanding member 8605 is free to expand outward as shown in FIG. 87.

Figure 88A:
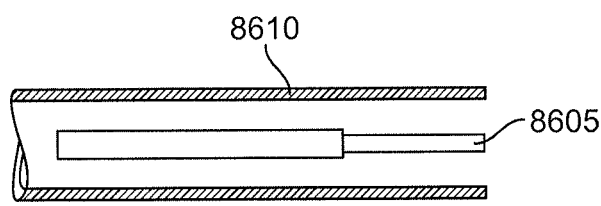
FIGS. 88A and 88B show side and front views, respectively, of another embodiment of an implant wherein the expanding members are elastic or superelastic fingers.
Figure 88B:
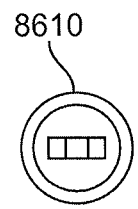
Figure 89:
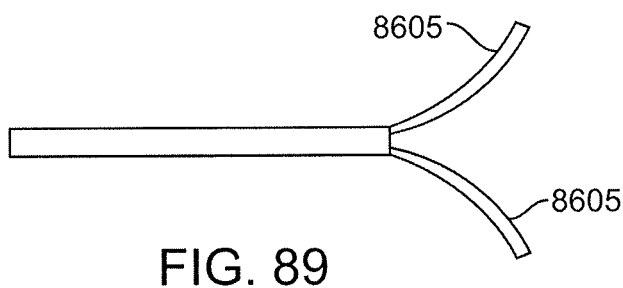
FIG. 89 shows the implant of FIGS. 88A and 88B with the expanding members in an expanded state.
Figure 90:
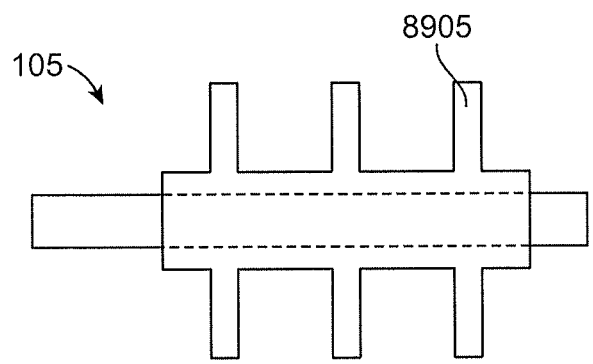
FIGS. 90 and 91 show an embodiment of an implant having finger-like expanding members.
Figure 91:
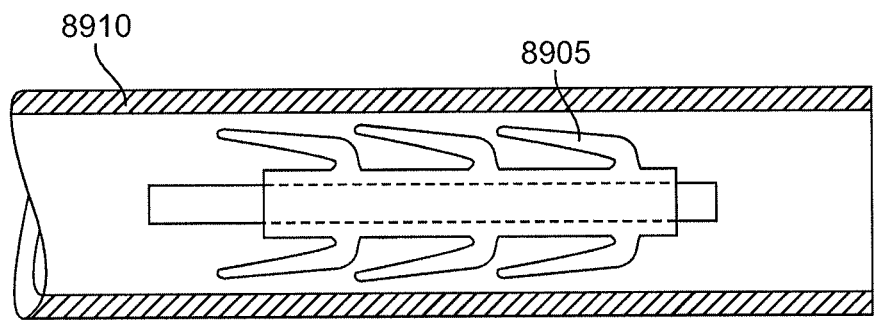

FIGS. 88A and 88B show side and front views, respectively, of another embodiment wherein the expanding members 8605 are elastic or superelastic fingers. When released from a sheath 8610 as shown in FIG. 89, the expanding members 8605 expand outward from the tubular body of the implant. In yet another embodiment shown in FIGS. 90 and 91, the implant has expanding members 8905 that are finger-like and formed of elastic or superelastic material. The implant 105 is positioned in a sheath 8910 that constrains the expanding members 8905 as shown in FIG. 91. Removal of the sheath 8910 permits the expanding members 8905 to transition to the expanded state as shown in FIG. 90.

In yet another embodiment, shown in FIGS. 92A-93B, the implant has an expansion member 9205 comprised of a wire (such as a Nitinol wire) having first and second ends attached to a distal tip of the implant. FIGS. 92A and 92B show side and front views, respectively of the implant 105 with the expansion member 9205 unconstrained. The expansion member 9205 forms a ring of increased radial dimension with respect to the implant. Prior to implantation, the implant 105 is positioned in a sheath 9310 that constrains the expansion member 9205 in a state of reduced size, as shown in FIGS. 93A and 93B. FIGS. 93A and 93B are schematic and show spaces between the implant and the internal wall of the sheath for clarity of illustration. In the actual embodiment, the implant or portions of the implant may abut the internal walls of the sheath.

Additional Implant Embodiments

Figure 94:
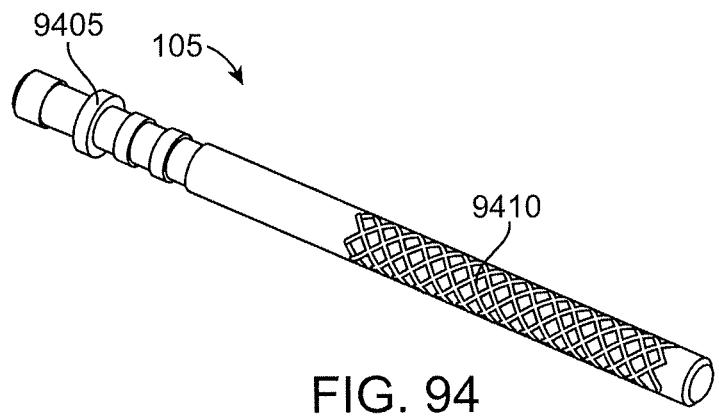
FIGS. 94-98 show additional embodiments of implants.
Figure 95:
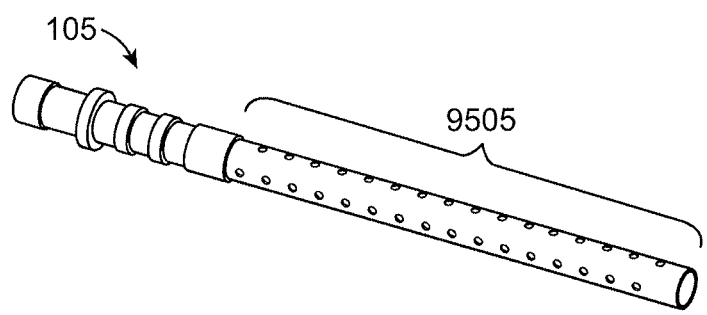
Figure 96:
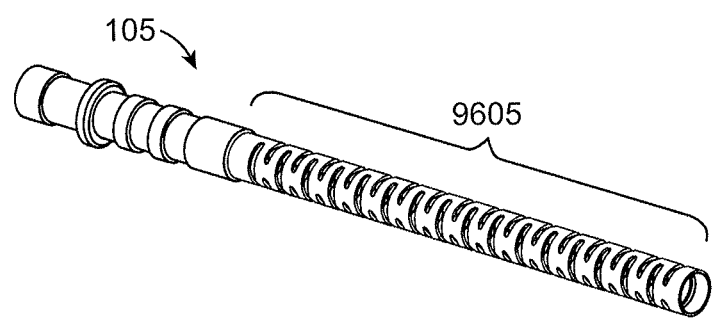

FIGS. 94-98 show additional embodiments of an implant 105. FIG. 94 shows an implant 105 comprised of an elongated, tubular member having a collar 9405 on a proximal end. At least a portion of the implant 105 has a knurled surface 9410 that can promote anchoring of the implant 105 with tissue. In an embodiment, the implant in FIG. 94 is manufactured of polyimide. FIG. 95 shows another embodiment of an implant 105 that is substantially similar to the implant shown in FIG. 94. In this embodiment, the implant 105 includes a region 9505 having fenestrations. In an embodiment, the implant in FIG. 95 is manufactured of polyimide. FIG. 96 shows yet another embodiment of an implant 105 that includes a fenestrated region 9605. The implant 105 in FIG. 95 is manufactured of flexible polyimide.

Figure 97:
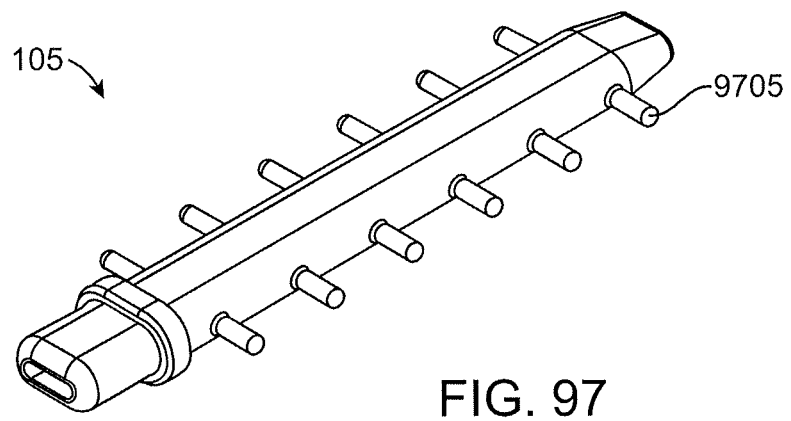

FIG. 97 shows another embodiment of an implant 105. In this embodiment, the implant 105 comprises a tubular member that is substantially more flat and less rounded than the tubular members shown in FIGS. 94-96. This provides the implant with a low profile when viewed along the longitudinal axis of the implant. The implant 105 in FIG. 97 has a plurality of anchoring members comprised of fingers 9705 that extend radially outward from the body of the implant. The fingers 9705 can be evenly spaced or non-evenly spaced along the length of the implant. In an embodiment, the implant of FIG. 97 is manufactured of silicone.

Figure 98:
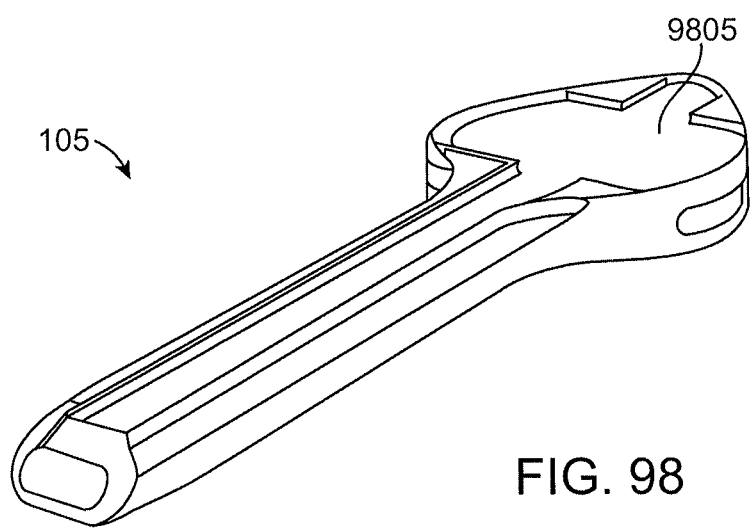

FIG. 98 shows another embodiment of the implant 105 comprised of a tubular member with an enlarged, bulbous region 9805 on one end of the implant. The region 9805 is sized and shaped such that the region 9805 can form a space or volume within tissue of the eye for collection of fluid. In an embodiment, the implant of FIG. 98 is formed of silicone.

Although embodiments of various methods and devices are described herein in detail with reference to certain versions, it should be appreciated that other versions, embodiments, methods of use, and combinations thereof are also possible. Therefore the spirit and scope of the appended claims should not be limited to the description of the embodiments contained herein.

What is claimed is:

1. An ocular implant, comprising:
a series of struts forming a series of fenestrations, wherein each of the series of struts comprises an outer convex surface and an inner concave surface that collectively form a generally cylindrical elongate body at least partially surrounding a longitudinal internal volume and wherein the struts form an outermost periphery of the ocular implant and also define the longitudinal internal volume, and wherein the series of fenestrations comprise adjacent, elongated openings located between each of the series of struts spaced along the major portion of the elongate body, wherein the elongated openings wrap around at least a portion of an outer circumference of the implant; and
a fluid ingress region communicating with the internal volume and located near an end portion of the elongate body, wherein the fluid ingress region is adapted to be positioned within an anterior chamber of an eye;
wherein fluid from the anterior chamber flows into the ingress region and out of the internal volume through one or more of the series of fenestrations when the elongate body is positioned in the eye;
and wherein the ocular implant has a uniform outermost diameter along the entire length of the region of the ocular implant that includes the fenestrations.

2. The implant of claim 1, wherein fluid from the anterior chamber flows out of the internal volume through one or more of the series of fenestrations toward the suprachoroidal space when the elongate body is positioned in the eye.

3. The implant of claim 1, wherein the fluid from the anterior chamber comprises aqueous fluid.

4. The implant of claim 1, wherein the series of fenestrations contributes a degree of flexibility to the elongate body.

5. The implant of claim 1, wherein the elongate body extends generally along a curved longitudinal central axis when implanted in the eye.

6. The implant of claim 1, wherein the series of struts are spaced along a majority of a length of the elongate body.

7. The implant of claim 1, wherein the series of struts are interconnected.

8. The implant of claim 1, wherein the series of struts are configured to maintain a space within the eye.

9. The implant of claim 1, wherein the elongate body is comprised of a shape-memory material.

10. The implant of claim 9, wherein the shape-memory material is Nitinol.

11. The implant of claim 1, wherein the internal volume is configured to allow fluid to flow laterally across the longitudinal internal volume through one or more of the series of fenestrations.

* * * * *